United States Patent
Turnbull et al.

(10) Patent No.: US 7,723,385 B2
(45) Date of Patent: May 25, 2010

(54) ANILINE DERIVATIVES AS SELECTIVE ANDROGEN RECEPTOR MODULATORS

(75) Inventors: Philip Stewart Turnbull, Durham, NC (US); Rodolfo Cadilla, Durham, NC (US); David John Cowan, Durham, NC (US); Andrew Lamont Larkin, Durham, NC (US); Istvan Kaldor, Durham, NC (US); Eugene Lee Stewart, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/392,687

(22) Filed: Feb. 25, 2009

(65) Prior Publication Data
US 2009/0163588 A1    Jun. 25, 2009

Related U.S. Application Data

(63) Continuation of application No. 10/598,508, filed as application No. PCT/US2005/007245 on Mar. 3, 2005, now Pat. No. 7,514,470.

(60) Provisional application No. 60/549,794, filed on Mar. 3, 2004.

(51) Int. Cl.
| | |
|---|---|
| A01N 37/34 | (2006.01) |
| A01N 33/02 | (2006.01) |
| A01N 33/18 | (2006.01) |
| A01N 33/24 | (2006.01) |
| A01N 27/00 | (2006.01) |
| A61K 31/275 | (2006.01) |
| A61K 31/135 | (2006.01) |
| A61K 31/04 | (2006.01) |
| A61K 31/015 | (2006.01) |
| C07C 255/00 | (2006.01) |
| C07C 321/00 | (2006.01) |
| C07C 323/00 | (2006.01) |
| C07C 381/00 | (2006.01) |
| C07C 221/00 | (2006.01) |
| C07C 223/00 | (2006.01) |
| C07C 225/00 | (2006.01) |

(52) U.S. Cl. ............... 514/524; 514/649; 514/741; 514/764; 558/419; 564/336; 564/340; 564/342; 564/345

(58) Field of Classification Search ............... 514/524, 514/649, 741, 764; 558/419; 564/336, 340, 564/342, 345
See application file for complete search history.

(56) References Cited

U.S. PATENT DOCUMENTS

2002/0990096    7/2002    Dalton et al.

FOREIGN PATENT DOCUMENTS

| WO | 9822441 A2 | 5/1998 |
| WO | 9822493 A2 | 5/1998 |
| WO | 2005000795 A2 | 1/2005 |
| WO | WO 2005/000795 | * 1/2005 |

OTHER PUBLICATIONS

Holla et al.; "Studies on Some N-Bridged Heterocycles Derived from bis-[4-amino-5-mercapto-1,2,4-triazol-3-yl] alkanes"; Il Farmaco; 1998; vol. 53, Nos. 8-9; pp. 574-578.
Waga et al.; "Synthesis of Plant Growth Substances"; Noguku Kenkyu; 1959; vol. 47; pp. 111-113.
Galin et al.; "Synthesis of N-phenylvaline Derivatives under Phase Transfer Catalysis"; Russian Journal of Organic Chemistry; 1998; vol. 34, No. 6; p. 899.
Saravanan et al.; "RN-244070-45-5"; Indian Drugs; 1999; vol. 36, No. 3; pp. 192-195.
Tortolani et al.; "A Convenient Synthesis to N-aryl-substituted 4-piperidones"; Organic Letters; 1999; vol. 1, No. 8; pp. 1261-1262.
Dovey et al.; "Functional Gamma-Secretase Inhibitors Reduce Beta-Amyloid Peptide Levels in Brain"; Journal of Neurochemistry; 2001; vol. 76, No. 1; pp. 173-181.
Das et al.; "Polyaniline Supported Cobalt(II)-Salen Catalyst: One Pot Synthesis of Beta-Phenylisoserine Derivatives from Cinnamoyl Amide"; Tetrahedron Letters; 1997; vol. 38, No. 16; pp. 2903-2906.
Dunkley et al.; "Synthesis and Biological Evaluation of a Novel Phenyl-Substituted Sydnone Series as Potential Antitumor Agents"; Bioorganic & Medicinal Chemistry Letters; 2003; vol. 13, No. 17; pp. 2899-2901.

* cited by examiner

*Primary Examiner*—San-ming Hui
*Assistant Examiner*—Paul Zarek
(74) *Attorney, Agent, or Firm*—Kathryn L. Coulter; Jennifer L. Fox

(57) ABSTRACT

This invention relates to non-steroidal compounds that are modulators of androgen, glucocorticoid, mineralocorticoid, and progesterone receptors, and also to the methods for the making and use of such compounds.

5 Claims, No Drawings

ANILINE DERIVATIVES AS SELECTIVE ANDROGEN RECEPTOR MODULATORS

CROSS-REFERENCE TO RELATED APPLICATIONS

This application is a continuation of U.S. patent application Ser. No. 10/598,508 filed Sep. 1, 2006, now allowed, which was filed pursuant to 35 U.S.C. §371 as a U.S. National Phase Application of International Application No. PCT/US2005/007245 filed Mar. 3, 2005, which claims priority from U.S. Provisional Application No. 60/549,794 filed Mar. 3, 2004.

FIELD OF THE INVENTION

This invention relates to non-steroidal compounds that are modulators of androgen, glucocorticoid, mineralocorticoid, and progesterone receptors, and also to the methods for the making and use of such compounds.

BACKGROUND OF THE INVENTION

Nuclear receptors are a class of structurally related gene expression modulators that act as ligand-dependent transcription factors (R. M. Evans, *Science* 240, 889 (1988)). The steroid receptors, namely the androgen receptor, the estrogen receptor, the glucocorticoid receptor, the mineralocorticoid receptor, and the progesterone receptor represent a subclass of the nuclear receptor superfamily. Nuclear receptor ligands in this subclass exert their effects by binding to an intracellular steroid hormone receptor. After the receptor-ligand complex is translocated to the nucleus of the cell, the complex binds to recognition sites on DNA, which allows for the modulation of certain genes.

Certain substances have demonstrated the ability to exhibit their activity in a tissue selective manner. In other words, tissue selectivity allows a nuclear receptor ligand to function as an agonist in some tissues, while having no effect or even an antagonist effect in other tissues. The term "selective receptor modulator" (SRM) has been given to these molecules. A synthetic compound that binds to an intracellular receptor and mimics the effects of the native hormone is referred to as an agonist. A compound that inhibits the effect of the native hormone is called an antagonist. The term "modulators" refers to compounds that have a spectrum of activities ranging from full agonism to partial agonism to full antagonism. The molecular basis for this tissue selective activity is not completely understood. Without being limited to any particular explanation, particular ligands put nuclear receptors in different conformational states. These states dictate the ability of coactivators, corepressors, and other proteins to be recruited by the nuclear receptor ("NR"). The unique cofactor-NR ensembles are the gene transcription factors that are thought to modulate tissue selective effects.

Ligand-mediated effects through the action of nuclear receptors are not limited to the classical genotropic mechanism outlined above. It is thought that some, if not all, of the separation of anabolic and general homeostatic effects from the stimulation of sexual tissues can be explained by a particular ligand's ability to potentiate non-genotropic pathways. One example of liganded nuclear receptor induction of non-genotropic pathways is found in the work of S. C. Manolagas et al., *Cell,* 104, 719-730. The action of a sex steroid NR on osteoblasts and other cell types is shown to involve the Src/Shc/ERK signaling pathway. This activity is mediated through the ligand binding domain of the sex steroid nuclear receptor alone. The NR DNA-binding domain is not required to attenuate etoposide-induced apoptosis in HeLa cells. An NR lacking the DNA binding domain cannot function in the classical mode, acting as a transcription factor.

Nuclear receptor steroid ligands are known to play important roles in the health of both men and women. In regard to men's health, testosterone (T) and dihydrotestosterone (DHT), for example, are endogenous steroidal ligands for the androgen receptor that likely play a role in every tissue type found in the mammalian body. During the development of the fetus, androgens play a role in sexual differentiation and development of male sexual organs. Further sexual development is mediated by androgens during puberty. Androgens play diverse roles in the adult including stimulation and maintenance of male sexual accessory organs and maintenance of the musculoskeletal system. Cognitive function, sexuality, aggression, and mood are some of the behavioral aspects mediated by androgens. Androgens affect the skin, bone, and skeletal muscle, as well as blood lipids and blood cells.

The study of androgen action and male reproductive dysfunction continues to expand significantly. In fact, only recently has the definition of a disease state been associated with hormonal changes that occur in aging men. This syndrome, previously referred to as Andropause, has more recently been described as Androgen Deficiency in the Aging Male, or "ADAM" (A. Morales and J. L. Tenover, *Urologic Clinics of North America* (2002 Nov.) 29(4) 975). The onset of ADAM is unpredictable and its manifestations are subtle and variable. Clinical manifestations of ADAM include fatigue, depression, decreased libido, erectile dysfunction as well as changes in cognition and mood.

Published information indicates that androgen replacement therapy (ART) in men may have benefits in terms of improving body composition parameters (e.g. bone mineral density, increasing muscle mass, and strength) as well as improving libido and mood in some men. Therefore, andrologists and other specialists are increasingly using ART for the treatment of the symptoms of ADAM—though there is due caution given androgen's, like testosterone, potential side effects. Nonetheless, there is increasing scientific rational of and evidence for androgen deficiency and treatment in the aging male. Current testosterone-based ART therapies include injections, skin patches, gel-based formulations, and oral preparations. All of these therapies are somewhat efficacious in the treatment of ADAM, but, due to the dramatic fluctuations in plasma T-levels following treatment, success with these therapies has been variable.

Testosterone replacement products, such as AndroGel® (1% testosterone gel CIII, marketed by Solvay Pharmaceuticals) are emerging as a treatment of choice among physicians. Such products, however, fail to correctly mimic physiological testosterone levels and have potential side effects including exacerbation of pre-existing sleep apnoea, polycythemia, and/or gynaecomastia. Furthermore, the longer-term side effects on target organs such as the prostate or the cardiovascular system are yet to be fully elucidated. Importantly, the potential carcinogenic effects of testosterone on the prostate prevent many physicians from prescribing it to older men (i.e. age >60 years) who, ironically, stand to benefit most from treatment. Also, all of the existing treatment options have fundamental problems with their delivery mechanism. The need for a novel selective androgen receptor modulator (SARM) is obviated by the potential side effect profile manifested in conventional treatments. A SARM would ideally have all the beneficial effects of endogenous androgens, while sparing sexual accessory organs, specifically the prostate.

In regard to female health, progesterone, the endogenous ligand for the progesterone receptor ("PR"), plays an important role in female reproduction during the various stages of the ovarian cycle and during pregnancy. Among other things, progesterone prepares the endometrium for implantation, regulates the implantation process, and helps maintain pregnancy. The therapeutic use of synthetic versions of progesterone (progestins) stems from progesterone's ability to regulate endometrial proliferation. In fact, progestins are included as part of hormone replacement therapy ("HRT") in women to reduce the incidence of endometriosis. Unfortunately, the effectiveness of therapy is tempered by undesired side-effect profiles. Chronic progestin therapy or continuous estrogen replacement regimens are often associated with increased bleeding. Excessive stimulatory effects on the endometrial vasculature may result in proliferation and fragility.

Compounds that modulate the effects of progesterone binding to PR are believed useful in the treatment and/or prophylaxis of endometriosis and uterine fibroid processes. Progesterone receptor antagonists such as mifepristone, also known as RU-486, and other PR modulators can inhibit endometrial proliferation at high estradiol concentrations in primates. Human clinical data with mifepristone supports the efficacy of a PR antagonist in endometriosis (D. R. Grow et al., *J. Clin. Endocrin. Metab.*, 1996, 81). Despite enthusiasm for its use, RU-486 also acts as a potent ligand for the glucocorticoid receptor ("GR"). This cross-reactivity with the GR is associated with homeostatic imbalances.

Thus, modulators of nuclear steroid hormones that are highly specific for one receptor could offer greater benefit with less side effects in the treatment of both female and male related hormone responsive diseases.

SUMMARY OF INVENTION

The present invention includes compounds of formula (I)

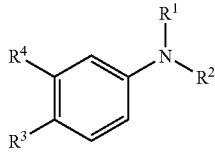

(I)

including salts, solvates, and physiologically functional derivatives thereof, wherein
$R^1$ is $-(Q^1)_x-R^5$;
$Q^1$ is alkylene;
x is 0 or 1;
$R^5$ is H, alkyl, alkenyl, alkynyl, haloalkyl, or cycloalkyl;
$R^2$ is $-(Q^3)-(Q^4)-R^6$, or $-(Q^3)-CN$;
$Q^3$ is alkylene;
$Q^4$ is -C(O)-, -C(S)-, or $-C(NR^7)-$;
$R^7$ is H or alkyl;
$R^6$ is alkyl, alkenyl, alkynyl, hydroxy, alkoxy, aryloxy, or $-N(R^8)(R^9)$
$R^8$ and $R^9$ each independently are H, hydroxy, alkyl, alkenyl, alkynyl, $-(Q^5)_y$-cycloalkyl, $-N(R^{10})(R^{11})$, or $R^8$ and $R^9$ combine with the nitrogen atom to which they are attached to form an optionally substituted 4 to 8 membered ring that may contain additional heteroatoms and may contain one or more degrees of unsaturation;
$Q^5$ is alkylene;
y is 0 or 1;
$R^{10}$ and $R^{11}$ each independently are H or alkyl;
$R^3$ is -CN, $-NO_2$, or halogen; and
$R^4$ is -CN, $-NO_2$, halogen, haloalkyl, alkyl, alkenyl, alkynyl, hydroxyl, alkoxy, aryl, aryloxy.

Preferably alkyl is $C_1-C_6$ alkyl, alkenyl is $C_1-C_6$ alkenyl, alkynyl is $C_1-C_6$ alkynyl, haloalkyl is $C_1-C_6$ haloalkyl, cycloalkyl is $C_3-C_6$ cycloalkyl, alkylene is $C_1-C_6$ alkylene, aryl is phenyl or naphthyl, alkoxy is $C_1-C_6$ alkoxy, and aryloxy is phenoxy or benzyloxy. In particular embodiments, alkylene is $C_1-C_2$ alkylene, haloalkyl is $-CF_3$, and cycloalkyl is cyclopropyl.

In one embodiment, preferably alkylene is a branched alkylene. For example, a preferred embodiment includes where alkylene is $-CH(CH_3)-$ or $-CH(CH_2CH_3)-$.

Preferably $R^3$ is -CN.
Preferably $R^4$ is halogen, haloalkyl, -CN or alkyl. Preferably $R^4$ is haloalkyl. More preferably $R^4$ is $-CF_3$.
Preferably $Q^1$ is methylene.
Preferably $R^5$ is $-CF_3$ or cyclopropyl.
Preferably $Q^3$ is methylene.
Preferably $Q^4$ is -C(O)-.
Preferably $R^6$ is $-N(R^8)(R^9)$, where $R^8$ and $R^9$ each independently are H or $C_1-C_6$ alkyl.
Preferably $R^3$ is -CN, $R^4$ is $-CF_3$, $Q^1$ is methylene, $R^5$ is $-CF_3$, $Q^3$ is methylene, $Q^4$ is -C(O)-, $R^6$ is $-N(R^8)(R^9)$, and $R^8$ and $R^9$ each are H.

Another aspect of the present invention includes a compound selected from:
1,1-dimethylethyl N-[4-cyano-3-(trifluoromethyl)phenyl]-N-(cyclopropylmethyl)glycinate;
N-[4-cyano-3-(trifluoromethyl)phenyl]-N-(cyclopropylmethyl)glycine;
$N^2$-[4-cyano-3-(trifluoromethyl)phenyl]-$N^2$-(cyclopropylmethyl)-$N^1$-methylglycinamide;
$N^2$-[4-cyano-3-(trifluoromethyl)phenyl]-$N^2$-(cyclopropylmethyl)glycinamide;
1,1-dimethylethyl N-[4-cyano-3-(trifluoromethyl)phenyl]-N-methylglycinate;
1,1-dimethylethyl N-[4-cyano-3-(trifluoromethyl)phenyl]-N-ethylglycinate;
N-[4-cyano-3-(trifluoromethyl)phenyl]-N-ethylglycine;
$N^2$-[4-cyano-3-(trifluoromethyl)phenyl]-$N^2$-ethylglycinamide;
$N^2$-[4-cyano-3-(trifluoromethyl)phenyl]-$N^2$-ethyl-$N^1$-propylglycinamide;
$N^2$-[4-cyano-3-(trifluoromethyl)phenyl]-$N^1$-(cyclopropylmethyl)-$N^2$-ethylglycinamide;
$N^2$-[4-cyano-3-(trifluoromethyl)phenyl]-$N^2$-ethyl-$N^1$, $N^1$-dipropylglycinamide;
1,1-dimethylethyl N-[4-Cyano-3-(trifluoromethyl)phenyl]-N-(2,2,2-trifluoroethyl)glycinate;
N-[4-cyano-3-(trifluoromethyl)phenyl]-N-(2,2,2-trifluoroethyl)glycine;
$N^2$-[4-cyano-3-(trifluoromethyl)phenyl]-$N^2$-(2,2,2-trifluoroethyl)glycinamide;
methyl N-[4-cyano-3-(trifluoromethyl)phenyl]-N-(2,2,2-trifluoroethyl)glycinate;
1-methylethyl N-[4-cyano-3-(trifluoromethyl)phenyl]-N-(2,2,2-trifluoroethyl)glycinate;
$N^2$-[4-cyano-3-(trifluoromethyl)phenyl]-$N^1$-methyl-$N^2$-(2,2,2-trifluoroethyl)glycinamide;
$N^2$-[4-cyano-3-(trifluoromethyl)phenyl]-$N^1$-ethyl-$N^2$-(2,2,2-trifluoroethyl)glycinamide;
$N^2$-[4-cyano-3-(trifluoromethyl)phenyl]-$N^1$-cyclohexyl-$N^2$-(2,2,2-trifluoroethyl)glycinamide;
$N^2$-[4-cyano-3-(trifluoromethyl)phenyl]-$N^1$,$N^1$-dimethyl-$N^2$-(2,2,2-trifluoroethyl)glycinamide;

2-[4-cyano(2,2,2-trifluoroethyl)-3-(trifluoromethyl)
    anilino]-N-methylacetohydrazide;
2-[4-cyano(2,2,2-trifluoroethyl)-3-(trifluoromethyl)
    anilino]-N',N'-dimethylacetohydrazide;
methyl N-[4-cyano-3-(trifluoromethyl)phenyl]-N-(2,2,2-trifluoroethyl)alaninate;
N-[4-cyano-3-(trifluoromethyl)phenyl]-N-(2,2,2-trifluoroethyl)alanine;
$N^2$-[4-cyano-3-(trifluoromethyl)phenyl]-$N^2$-(2,2,2-trifluoroethyl)alaninamide;
$N^2$-[4-cyano-3-(trifluoromethyl)phenyl]-$N^1$-methyl-$N^2$-(2,2,2-trifluoroethyl)alaninamide;
$N^2$-[4-cyano-3-(trifluoromethyl)phenyl]-$N^1$-ethyl-$N^2$-(2,2,2-trifluoroethyl)alaninamide;
$N^2$-[4-cyano-3-(trifluoromethyl)phenyl]-$N^1$,$N^1$-dimethyl-$N^2$-(2,2,2-trifluoroethyl)alaninamide;
1,1-dimethylethyl 2-[[4-cyano-3-(trifluoromethyl)phenyl](2,2,2-trifluoroethyl)amino]butanoate;
2-[[4-cyano-3-(trifluoromethyl)phenyl](2,2,2-trifluoroethyl)amino]butanoic acid;
2-[[4-cyano-3-(trifluoromethyl)phenyl](2,2,2-trifluoroethyl)amino]butanamide;
2-[[4-cyano-3-(trifluoromethyl)phenyl](2,2,2-trifluoroethyl)amino]-N-methylbutanamide;
2-[[4-cyano-3-(trifluoromethyl)phenyl](2,2,2-trifluoroethyl)amino]-N-ethylbutanamide;
2-[[4-cyano-3-(trifluoromethyl)phenyl](2,2,2-trifluoroethyl)amino]-N,N-dimethylbutanamide;
1,1-dimethylethyl N-[4-cyano-3-(trifluoromethyl)phenyl]-N-propylglycinate;
N-[4-cyano-3-(trifluoromethyl)phenyl]-N-propylglycine;
$N^2$-[4-cyano-3-(trifluoromethyl)phenyl]-$N^2$-propylglycinamide;
$N^2$-[4-cyano-3-(trifluoromethyl)phenyl]-$N^1$,$N^2$-dipropylglycinamide;
$N^2$-[4-cyano-3-(trifluoromethyl)phenyl]-$N^1$-(cyclopropylmethyl)-$N^2$-propylglycinamide;
1,1-dimethylethyl N-[4-cyano-3-(trifluoromethyl)phenyl]-$N^2$-propen-1-ylglycinate;
methyl N-[4-cyano-3-(trifluoromethyl)phenyl]-N-(2-fluoroethyl)glycinate;
$N^2$-[4-cyano-3-(trifluoromethyl)phenyl]-$N^2$-(2-fluoroethyl)glycinamide;
1,1-dimethylethyl N-[4-cyano-3-(trifluoromethyl)phenyl]-N-(2-methylpropyl)glycinate;
N-[4-cyano-3-(trifluoromethyl)phenyl]-N-isobutylglycine;
$N^2$-[4-cyano-3-(trifluoromethyl)phenyl]-$N^2$-isobutylglycinamide;
$N^2$-[4-cyano-3-(trifluoromethyl)phenyl]-$N^2$-isobutyl-$N^1$-methylglycinamide;
$N^2$-[4-cyano-3-(trifluoromethyl)phenyl]-$N^2$-(cyclopropylmethyl)-$N^1$-ethylglycinamide;
$N^2$-[4-cyano-3-(trifluoromethyl)phenyl]-$N^1$,$N^2$-bis(cyclopropylmethyl)glycinamide;
1,1-dimethylethyl N-[4-cyano-3-(trifluoromethyl)phenyl]-N-(cyclopropylmethyl)alaninate;
N-[4-cyano-3-(trifluoromethyl)phenyl]-N-(cyclopropylmethyl)alanine;
$N^2$-[4-cyano-3-(trifluoromethyl)phenyl]-$N^2$-(cyclopropylmethyl)alaninamide;
$N^2$-[4-cyano-3-(trifluoromethyl)phenyl]-$N^2$-(cyclopropylmethyl)-$N^1$-methylalaninamide;
$N^2$-[4-cyano-3-(trifluoromethyl)phenyl]-$N^2$-(cyclopropylmethyl)-$N^1$-ethylalaninamide;
$N^2$-[4-cyano-3-(trifluoromethyl)phenyl]-$N^2$-(cyclopropylmethyl)-$N^1$,$N^1$-dimethylalaninamide;
4-[(cyanomethyl)(2,2,2-trifluoroethyl)amino]-2-(trifluoromethyl)benzonitrile;
4-[(1-cyanoethyl)(2,2,2-trifluoroethyl)amino]-2-(trifluoromethyl)benzonitrile;
methyl 3-[[4-cyano-3-(trifluoromethyl)phenyl](2,2,2-trifluoroethyl)amino]-2-methylpropanoate;
4-[(2-cyanopropyl)(2,2,2-trifluoroethyl)amino]-2-(trifluoromethyl)benzonitrile;
N-[4-cyano-3-(trifluoromethyl)phenyl]-N-(2,2-dimethylpropyl)glycine;
$N^2$-[4-cyano-3-(trifluoromethyl)phenyl]-$N^2$-(2,2-dimethylpropyl)glycinamide;
$N^2$-[4-cyano-3-(trifluoromethyl)phenyl]-$N^2$-(2,2,2-trifluoro-1-methylethyl)glycinamide;
$N^2$-[4-cyano-3-(trifluoromethyl)phenyl]-$N^2$-[1-(trifluoromethyl)propyl]glycinamide;
1,1-dimethylethyl N-[4-cyano-3-(trifluoromethyl)phenyl]-N-(3,3,3-trifluoropropyl)glycinate;
$N^2$-[4-cyano-3-(trifluoromethyl)phenyl]-$N^2$-(3,3,3-trifluoropropyl)glycinamide;
4-[(cyanomethyl)(3,3,3-trifluoropropyl)amino]-2-(trifluoromethyl)benzonitrile;
$N^2$-[4-cyano-3-(trifluoromethyl)phenyl]-$N^2$-(3,3,3-trifluoropropyl)alaninamide;
$N^2$-[4-cyano-3-(trifluoromethyl)phenyl]-$N^1$-methyl-$N^2$-(3,3,3-trifluoropropyl)alaninamide;
$N^2$-[4-cyano-3-(trifluoromethyl)phenyl]-$N^2$-(1,1-dimethylethyl)glycinamide;
$N^2$-[4-cyano-3-(trifluoromethyl)phenyl]-$N^2$-(1-methylethyl)glycinamide;
$N^2$-[4-cyano-3-(trifluoromethyl)phenyl]-$N^1$-methyl-$N^2$-(1-methylethyl)glycinamide;
4-[(cyanomethyl)(methyl)amino]-2-(trifluoromethyl)benzonitrile;
4-[(2-cyanoethyl)(methyl)amino]-2-(trifluoromethyl)benzonitrile;
1,1-dimethylethyl N-(3-chloro-4-cyanophenyl)-N-(2,2,2-trifluoroethyl)glycinate;
N-(3-chloro-4-cyanophenyl)-N-(2,2,2-trifluoroethyl)glycine;
$N^2$-(3-chloro-4-cyanophenyl)-$N^2$-(2,2,2-trifluoroethyl)glycinamide;
$N^2$-(3-chloro-4-cyanophenyl)-$N^1$-methyl-N2-(2,2,2-trifluoroethyl)glycinamide;
$N^2$-(3-chloro-4-cyanophenyl)-$N^1$-ethyl-$N^2$-(2,2,2-trifluoroethyl)glycinamide;
1,1-dimethylethyl N-(3-chloro-4-cyanophenyl)-N-(2,2,2-trifluoroethyl)alaninate;
N-(3-chloro-4-cyanophenyl)-N-(2,2,2-trifluoroethyl)alanine;
$N^2$-(3-chloro-4-cyanophenyl)-$N^2$-(2,2,2-trifluoroethyl)alaninamide;
$N^2$-(3-chloro-4-cyanophenyl)-$N^1$-methyl-N2-(2,2,2-trifluoroethyl)alaninamide;
$N^2$-(3-chloro-4-cyanophenyl)-$N^1$-ethyl-$N^2$-(2,2,2-trifluoroethyl)alaninamide;
1,1-dimethylethyl 2-[(3-chloro-4-cyanophenyl)(2,2,2-trifluoroethyl)amino]butanoate;
2-[(3-chloro-4-cyanophenyl)(2,2,2-trifluoroethyl)amino]butanamide;
2-[(3-chloro-4-cyanophenyl)(2,2,2-trifluoroethyl)amino]-N-methylbutanamide;
2-[(3-chloro-4-cyanophenyl)(2,2,2-trifluoroethyl)amino]-N-ethylbutanamide;
1,1-dimethylethyl N-(3-chloro-4-cyanophenyl)-N-(cyclopropylmethyl)glycinate;

N-(3-chloro-4-cyanophenyl)-N-(cyclopropylmethyl)glycine;

$N^2$-(3-chloro-4-cyanophenyl)-$N^2$-(cyclopropylmethyl)glycinamide;

$N^2$-(3-chloro-4-cyanophenyl)-$N^2$-(cyclopropylmethyl)-$N^1$-methylglycinamide;

$N^2$-(3-chloro-4-cyanophenyl)-$N^2$-(cyclopropylmethyl)-$N^1$-ethylglycinamide;

2-chloro-4-[(cyanomethyl)(cyclopropylmethyl)amino]benzonitrile;

1,1-dimethylethyl N-(3-chloro-4-cyanophenyl)-N-(cyclopropylmethyl)alaninate;

N-(3-chloro-4-cyanophenyl)-N-(cyclopropylmethyl)alanine;

$N^2$-(3-chloro-4-cyanophenyl)-$N^2$-(cyclopropylmethyl)alaninamide;

$N^2$-(3-chloro-4-cyanophenyl)-$N^2$-(cyclopropylmethyl)-$N^1$-methylalaninamide;

$N^2$-(3-chloro-4-cyanophenyl)-$N^2$-(cyclopropylmethyl)-$N^1$-ethylalaninamide;

1,1-dimethylethyl 2-[(3-chloro-4-cyanophenyl)(cyclopropylmethyl)amino]butanoate;

2-[(3-chloro-4-cyanophenyl)(cyclopropylmethyl)amino]butanoic acid;

2-[(3-chloro-4-cyanophenyl)(cyclopropylmethyl)amino]butanamide;

2-[(3-chloro-4-cyanophenyl)(cyclopropylmethyl)amino]-N-methylbutanamide;

2-[(3-chloro-4-cyanophenyl)(cyclopropylmethyl)amino]-N-ethyl butanamide;

methyl N-(3,4-dicyanophenyl)-N-(2,2,2-trifluoroethyl)glycinate;

1,1-dimethylethyl N-(3,4-dicyanophenyl)-N-(2,2,2-trifluoroethyl)glycinate;

$N^2$-(3,4-dicyanophenyl)-$N^2$-(2,2,2-trifluoroethyl)glycinamide;

$N^2$-(3,4-dicyanophenyl)-$N^1$-methyl-$N^2$-(2,2,2-trifluoroethyl)glycinamide;

$N^2$-(3,4-dicyanophenyl)-$N^1$-ethyl-$N^2$-(2,2,2-trifluoroethyl)glycinamide;

1,1-dimethylethyl N-(3,4-dicyanophenyl)-N-(2,2,2-trifluoroethyl)alaninate;

N-(3,4-dicyanophenyl)-N-(2,2,2-trifluoroethyl)alanine;

$N^2$-(3,4-dicyanophenyl)-$N^2$-(2,2,2-trifluoroethyl)alaninamide;

$N^2$-(3,4-dicyanophenyl)-$N^1$-methyl-$N^2$-(2,2,2-trifluoroethyl)alaninamide;

$N^2$-(3,4-dicyanophenyl)-$N^1$-ethyl-$N^2$-(2,2,2-trifluoroethyl)alaninamide;

1,1-dimethylethyl 2-[(3,4-dicyanophenyl)(2,2,2-trifluoroethyl)amino]butanoate;

2-[(3,4-dicyanophenyl)(2,2,2-trifluoroethyl)amino]butanoic acid;

2-[(3,4-dicyanophenyl)(2,2,2-trifluoroethyl)amino]butanamide;

2-[(3,4-dicyanophenyl)(2,2,2-trifluoroethyl)amino]-N-methylbutanamide;

2-[(3,4-dicyanophenyl)(2,2,2-trifluoroethyl)amino]-N-ethylbutanamide;

1,1-dimethylethyl N-(cyclopropylmethyl)-N-(3,4-dicyanophenyl)glycinate;

N-(cyclopropylmethyl)-N-(3,4-dicyanophenyl)glycine;

$N^2$-(cyclopropylmethyl)-$N^2$-(3,4-dicyanophenyl)glycinamide;

$N^2$-(cyclopropylmethyl)-$N^2$-(3,4-dicyanophenyl)-$N^1$-methylglycinamide;

$N^2$-(cyclopropylmethyl)-$N^2$-(3,4-dicyanophenyl)-$N^1$-ethylglycinamide;

4-[(cyanomethyl)(cyclopropylmethyl)amino]-1,2-benzenedicarbonitrile;

1,1-dimethylethyl N-(cyclopropylmethyl)-N-(3,4-dicyanophenyl)alaninate;

N-(cyclopropylmethyl)-N-(3,4-dicyanophenyl)alanine;

$N^2$-(cyclopropylmethyl)-$N^2$-(3,4-dicyanophenyl)-$N^1$-methylalaninamide;

$N^2$-(cyclopropylmethyl)-$N^2$-(3,4-dicyanophenyl)-$N^1$-ethylalaninamide;

1,1-dimethylethyl 2-[(cyclopropylmethyl)(3,4-dicyanophenyl)amino]butanoate;

2-[(cyclopropylmethyl)(3,4-dicyanophenyl)amino]butanoic acid;

2-[(cyclopropylmethyl)(3,4-dicyanophenyl)amino]butanamide;

2-[(cyclopropylmethyl)(3,4-dicyanophenyl)amino]-N-methylbutanamide;

and 2-[(cyclopropylmethyl)(3,4-dicyanophenyl)amino]-N-ethylbutanamide.

Another aspect of the present invention includes a compound substantially as hereinbefore defined with reference to any one of the Examples.

Another aspect of the present invention includes a pharmaceutical composition comprising a compound of the present invention and a pharmaceutically acceptable carrier.

Another aspect of the present invention includes a compound of the present invention for use as an active therapeutic substance.

Another aspect of the present invention includes a compound of the present invention for use in the treatment or prophylaxis of conditions or disorders that respond to selective androgen receptor modulation.

Another aspect of the present invention includes a compound of the present invention for use in the treatment or prophylaxis of osteoporosis, muscle wasting, frailty, cardiovascular disease, breast cancer, uterine cancer, prostate hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM.

Another aspect of the present invention includes the use of a compound of the present invention in the manufacture of a medicament for use in the treatment or prophylaxis of conditions or disorders that respond to selective androgen receptor modulation.

Another aspect of the present invention includes using a compound according to the present invention in the manufacture of a medicament for use in the treatment or prophylaxis of osteoporosis, muscle wasting, frailty, cardiovascular disease, breast cancer, uterine cancer, prostatic hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM.

Another aspect of the present invention includes a method for the treatment or prophylaxis of conditions or disorders that respond to selective androgen receptor modulation comprising the administration of a compound according to the present invention.

Another aspect of the present invention includes a method for the treatment or prophylaxis of osteoporosis, muscle wasting, frailty, cardiovascular disease, breast cancer, uterine cancer, prostatic hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM comprising the administration of a compound according to the present invention.

The compounds of the present invention modulate the androgen receptor ("AR"). Certain compounds of the present invention also modulate the function of other nuclear hormone receptors.

More particularly, the present invention includes compounds that are selective agonists, partial agonists, antagonists, or partial antagonists of the AR. Compounds of the present invention are useful in the treatment of AR-associated diseases and conditions, for example, a disease or condition that is prevented, alleviated, or cured through the modulation of the function or activity of AR. Such modulation may be isolated within certain tissues or widespread throughout the body of the subject being treated.

An aspect of the present invention is the use of the compounds of the present invention for the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM.

DETAILED DESCRIPTION OF THE PREFERRED EMBODIMENT

Terms are used within their accepted meanings. The following definitions are meant to clarify, but not limit, the terms defined.

As used herein the term "alkyl" refers to a straight or branched chain hydrocarbon, preferably having from one to twelve carbon atoms, which may be optionally substituted, with multiple degrees of substitution included within the present invention. Examples of "alkyl" as used herein include, but are not limited to, methyl, ethyl, propyl, isopropyl, isobutyl, n-butyl, tert-butyl, isopentyl, n-pentyl, and substituted versions thereof.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl and the like and substituted versions thereof.

As used herein the term "alkynyl" refers to a straight or branched chain aliphatic hydrocarbon containing one or more carbon-to-carbon triple bonds that may be optionally substituted, with multiple degrees of substitution included within the present invention. Examples include, but are not limited to, ethynyl and the like and substituted versions thereof.

As used herein, the term "alkylene" refers to a straight or branched chain divalent hydrocarbon radical, preferably having from one to ten carbon atoms. Alkylene groups as defined herein may optionally be substituted, with multiple degrees of substitution included within the present invention. Examples of "alkylene" as used herein include, but are not limited to, methylene (-$CH_2$-), ethylene (-$CH_2$—$CH_2$-), and substituted versions thereof.

As used herein, the term "cycloalkyl" refers to an optionally substituted non-aromatic cyclic hydrocarbon ring, which optionally includes an alkylene linker through which the cycloalkyl may be attached, with multiple degrees of substitution included within the present invention. Exemplary "cycloalkyl" groups include, but are not limited to, cyclopropyl, cyclobutyl, cyclopentyl, cyclohexyl, cycloheptyl, and substituted versions thereof.

As used herein, the term "aryl" refers to an optionally substituted benzene ring or to an optionally substituted fused benzene ring system, for example anthracene, phenanthrene, or naphthalene ring systems. Multiple degrees of substitution are included within the present definition. Examples of "aryl" groups include, but are not limited to, phenyl, 2-naphthyl, 1-naphthyl, biphenyl, and substituted derivatives thereof.

As used herein, the term "heteroaryl" refers to an optionally substituted monocyclic five to seven membered aromatic ring, or to an optionally substituted fused bicyclic aromatic ring system comprising two of such aromatic rings, which contain one or more nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein the term "halogen" refers to fluorine, chlorine, bromine, or iodine.

As used herein the term "haloalkyl" refers to an alkyl group, as defined herein that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such groups such as -$CF_3$, -$CH_2$—$CH_2$—F, and the like.

As used herein the term "hydroxy" refers to the group -OH.

As used herein the term "mercapto" refers to the group -SH.

As used herein the term "alkoxy" refers to the group -OR$_a$, where R$_a$ is alkyl as defined above.

As used herein the term "aryloxy" refers to the group -OR$_b$, where R$_b$ is aryl as defined above.

As used herein the term "nitro" refers to the group -NO$_2$.

As used herein the term "cyano" refers to the group -CN.

As used herein the term "amino" refers to the group -NH$_2$, and "substituted amino" refers to a group -N(R$_a$)(R$_b$), where one or both R$_a$ and R$_b$ are other than H. For example, "substituted amino" includes the groups -N(CH$_3$)(CH$_3$), —N(CH$_3$)(CH$_2$—CH$_3$), and the like.

As used herein throughout the present specification, the phrase "optionally substituted" or variations thereof denote an optional substitution, including multiple degrees of substitution, with one or more substituent group. As noted above, terms used throughout this specification should be considered as optionally substituted unless otherwise noted. The phrase should not be interpreted as duplicative of substitution patterns herein described or depicted.

Exemplary optional substituent groups include acyl; alkyl; alkenyl; alkynyl; alkylsulfonyl; alkoxy; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; or -N(R*)$_2$; where for each occurrence R* is independently selected from H, alkyl, alkenyl, alkynyl, cycloalkyl, heterocyclyl, aryl, aralkyl, heteroaryl, heteroaralkyl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or the two R*s may combine to form a ring, optionally having additional heteroatoms, optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry and Drug Discovery*, 5$^{th}$ Edition, Vol. 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The biological or medical response may be considered a prophylactic response or a treatment response. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

In one embodiment of the present invention is a compound of formula (IA)

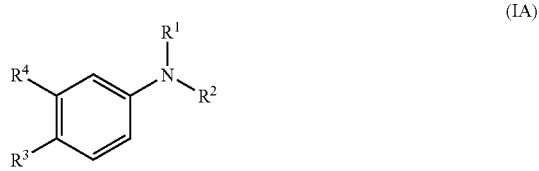

including salts, solvates, and physiologically functional derivatives thereof, wherein $R^1$ is -$(Q^1)_x$-$R^5$;
$Q^1$ is alkylene;
x is 0 or 1;
$R^5$ is H, alkyl, alkenyl, alkynyl, haloalkyl, or cycloalkyl;
$R^2$ is -$(Q^3)$-$(Q^4)$-$R^6$;
$Q^3$ is alkylene;
$Q^4$ is -C(O)-, -C(S)-, or -C($NR^7$)-;
$R^7$ is H or alkyl;
$R^6$ is alkyl, alkenyl, alkynyl, hydroxy, alkoxy, aryloxy, or -N($R^8$)($R^9$)
$R^8$ and $R^9$ each independently are H, hydroxy, alkyl, alkenyl, alkynyl, -$(Q^5)_y$-cycloalkyl, -N($R^{10}$)($R^{11}$), or $R^8$ and $R^9$ combine with the nitrogen atom to which they are attached to form an optionally substituted 4 to 8 membered ring that may contain additional heteroatoms and may contain one or more degrees of unsaturation;
$Q^5$ is alkylene;
y is 0 or 1;
$R^{10}$ and $R^{11}$ each independently are H or alkyl;
$R^3$ is -CN, or -$NO_2$; and
$R^4$ is -CN, -$NO_2$, halogen, haloalkyl, alkyl, alkenyl, alkynyl, hydroxyl, alkoxy, aryl, aryloxy.

While the preferred groups for each variable have generally been listed above separately for each variable, preferred compounds of this invention include those in which several of each variable in Formula (I) is selected from the preferred, more preferred, or most preferred groups for each variable. Therefore, this invention is intended to include all combinations of preferred, more preferred, and most preferred groups.

Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment or prophylaxis of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules can be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets can be formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents for the treatment of the above-mentioned conditions. For example, in frailty therapy, combination may be had with other anabolic or osteoporosis therapeutic agents. As one example, osteoporosis combination therapies according to the present invention would thus comprise the administration of at least one compound of formula (I) or a salt, solvate, or physiologically functional derivative thereof, and the use of at least one other osteoporosis therapy. As a further example, combination therapies according to the present invention include the administration of at least one compound of formula (I) or a salt, solvate, or physiologically functional derivative thereof, and at least one other osteoporosis treatment agent, for example, an anti-bone resorption agent. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Another potential osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-ardenergic agonists, serotonin 5-$HT_D$ agonists, agents that inhibit somatostatin or its release, 5-α-reductase inhibitors, aromatase inhibitors, GnRH agonists or antagonists, parathyroid hormone, bisphosphonates, estrogen, testosterone, SERMs, progesterone receptor agonists or antagonists, and/or with other modulators of nuclear hormone receptors.

One skilled in the art will acknowledge that although the compounds embodied herein will be used as selective agonists, partial agonists, and antagonists, compounds with mixed steroid activities may also be employed.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM.

In particular, the compounds of the present invention are believed useful, either alone or in combination with other agents, in the treatment of and use as male and female hormone replacement therapy, hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents.

Another aspect of the present invention thus also provides compounds of formula (I) and salts, solvates, or physiologically functional derivatives thereof, for use in medical therapy. Particularly, the present invention provides for the treatment or prophylaxis of disorders mediated by androgenic activity. More particularly, the present invention provides through the treatment or prophylaxis of disorders responsive to tissue-selective anabolic and or androgenic activity. A further aspect of the invention provides a method of treatment or prophylaxis of a mammal suffering from a disorder mediated by androgenic activity, which includes administering to said subject an effective amount of a compound of formula (I) or a salt, solvate, or physiologically functional derivative thereof.

A further aspect of the invention provides a method of treatment or prophylaxis of a mammal requiring the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM. Preferably the compounds of the present invention are used as male and female hormone replacement therapy or for the treatment or prevention of hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents, which use includes administering to a subject an effective amount of a compound of formula (I) or a salt, solvate, or physiologically functional derivative thereof. The mammal requiring treatment with a compound of the present invention is typically a human being.

The compounds of this invention may be made by a variety of methods, including well-known standard synthetic methods. Illustrative general synthetic methods are set out below and then specific compounds of the invention are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

Representative AR modulator compounds, agonists, partial agonists, and antagonists according to the current invention include:

1,1-dimethylethyl N-[4-cyano-3-(trifluoromethyl)phenyl]-N-(cyclopropylmethyl)glycinate;

N-[4-cyano-3-(trifluoromethyl)phenyl]-N-(cyclopropylmethyl)glycine;

$N^2$-[4-cyano-3-(trifluoromethyl)phenyl]-$N^2$-(cyclopropylmethyl)-$N^1$-methylglycinamide;

$N^2$-[4-cyano-3-(trifluoromethyl)phenyl]-$N^2$-(cyclopropylmethyl)glycinamide;

1,1-dimethylethyl N-[4-cyano-3-(trifluoromethyl)phenyl]-N-methylglycinate;

1,1-dimethylethyl N-[4-cyano-3-(trifluoromethyl)phenyl]-N-ethylglycinate;

N-[4-cyano-3-(trifluoromethyl)phenyl]-N-ethylglycine;

$N^2$-[4-cyano-3-(trifluoromethyl)phenyl]-$N^2$-ethylglycinamide;

$N^2$-[4-cyano-3-(trifluoromethyl)phenyl]-$N^2$-ethyl-$N^1$-propylglycinamide;

$N^2$-[4-cyano-3-(trifluoromethyl)phenyl]-$N^1$-(cyclopropylmethyl)-$N^2$-ethylglycinamide;

$N^2$-[4-cyano-3-(trifluoromethyl)phenyl]-$N^2$-ethyl-$N^1$,$N^1$-dipropylglycinamide;

1,1-dimethylethyl N-[4-cyano-3-(trifluoromethyl)phenyl]-N-(2,2,2-trifluoroethyl)glycinate;

N-[4-cyano-3-(trifluoromethyl)phenyl]-N-(2,2,2-trifluoroethyl)glycine;

$N^2$-[4-cyano-3-(trifluoromethyl)phenyl]-$N^2$-(2,2,2-trifluoroethyl)glycinamide;

methyl N-[4-cyano-3-(trifluoromethyl)phenyl]-N-(2,2,2-trifluoroethyl)glycinate;

1-methylethyl N-[4-cyano-3-(trifluoromethyl)phenyl]-N-(2,2,2-trifluoroethyl)glycinate;

$N^2$-[4-cyano-3-(trifluoromethyl)phenyl]-$N^1$-methyl-$N^2$-(2,2,2-trifluoroethyl)glycinamide;

$N^2$-[4-cyano-3-(trifluoromethyl)phenyl]-$N^1$-ethyl-$N^2$-(2,2,2-trifluoroethyl)glycinamide;

$N^2$-[4-cyano-3-(trifluoromethyl)phenyl]-$N^1$-cyclohexyl-$N^2$-(2,2,2-trifluoroethyl)glycinamide;

$N^2$-[4-cyano-3-(trifluoromethyl)phenyl]-$N^1$, $N^1$-dimethyl-$N^2$-(2,2,2-trifluoroethyl)glycinamide;

2-[4-cyano(2,2,2-trifluoroethyl)-3-(trifluoromethyl)anilino]-N-methylacetohydrazide;

2-[4-cyano(2,2,2-trifluoroethyl)-3-(trifluoromethyl)anilino]-N',N'-dimethylacetohydrazide;

methyl N-[4-cyano-3-(trifluoromethyl)phenyl]-N-(2,2,2-trifluoroethyl)alaninate;

N-[4-cyano-3-(trifluoromethyl)phenyl]-N-(2,2,2-trifluoroethyl)alanine;
$N^2$-[4-cyano-3-(trifluoromethyl)phenyl]-$N^2$-(2,2,2-trifluoroethyl)alaninamide;
$N^2$-[4-cyano-3-(trifluoromethyl)phenyl]-$N^1$-methyl-$N^2$-(2,2,2-trifluoroethyl)alaninamide;
$N^2$-[4-cyano-3-(trifluoromethyl)phenyl]-$N^1$-ethyl-$N^2$-(2,2,2-trifluoroethyl)alaninamide;
$N^2$-[4-cyano-3-(trifluoromethyl)phenyl]-$N^1$,$N^1$-dimethyl-$N^2$-(2,2,2-trifluoroethyl)alaninamide;
1,1-dimethylethyl 2-[[4-cyano-3-(trifluoromethyl)phenyl](2,2,2-trifluoroethyl)amino]butanoate;
2-[[4-cyano-3-(trifluoromethyl)phenyl](2,2,2-trifluoroethyl)amino]butanoic acid;
2-[[4-cyano-3-(trifluoromethyl)phenyl](2,2,2-trifluoroethyl)amino]butanamide;
2-[[4-cyano-3-(trifluoromethyl)phenyl](2,2,2-trifluoroethyl)amino]-N-methylbutanamide;
2-[[4-cyano-3-(trifluoromethyl)phenyl](2,2,2-trifluoroethyl)amino]-N-ethylbutanamide;
2-[[4-cyano-3-(trifluoromethyl)phenyl](2,2,2-trifluoroethyl)amino]-N,N-dimethylbutanamide;
1,1-dimethylethyl N-[4-cyano-3-(trifluoromethyl)phenyl]-N-propylglycinate;
N-[4-cyano-3-(trifluoromethyl)phenyl]-N-propylglycine;
$N^2$-[4-cyano-3-(trifluoromethyl)phenyl]-$N^2$-propylglycinamide;
$N^2$-[4-cyano-3-(trifluoromethyl)phenyl]-$N^1$,$N^2$-dipropylglycinamide;
$N^2$-[4-cyano-3-(trifluoromethyl)phenyl]-$N^1$-(cyclopropylmethyl)-$N^2$-propylglycinamide;
1,1-dimethylethyl N-[4-cyano-3-(trifluoromethyl)phenyl]-$N^2$-propen-1-ylglycinate;
methyl N-[4-cyano-3-(trifluoromethyl)phenyl]-N-(2-fluoroethyl)glycinate;
$N^2$-[4-cyano-3-(trifluoromethyl)phenyl]-$N^2$-(2-fluoroethyl)glycinamide;
1,1-dimethylethyl N-[4-cyano-3-(trifluoromethyl)phenyl]-N-(2-methylpropyl)glycinate;
N-[4-cyano-3-(trifluoromethyl)phenyl]-N-isobutylglycine;
$N^2$-[4-cyano-3-(trifluoromethyl)phenyl]-$N^2$-isobutylglycinamide;
$N^2$-[4-cyano-3-(trifluoromethyl)phenyl]-$N^2$-isobutyl-$N^1$-methylglycinamide;
$N^2$-[4-cyano-3-(trifluoromethyl)phenyl]-$N^2$-(cyclopropylmethyl)-$N^1$-ethylglycinamide;
$N^2$-[4-cyano-3-(trifluoromethyl)phenyl]-$N^1$,$N^2$-bis(cyclopropylmethyl)glycinamide;
1,1-dimethylethyl N-[4-cyano-3-(trifluoromethyl)phenyl]-N-(cyclopropylmethyl)alaninate;
N-[4-cyano-3-(trifluoromethyl)phenyl]-N-(cyclopropylmethyl)alanine;
$N^2$-[4-cyano-3-(trifluoromethyl)phenyl]-$N^2$-(cyclopropylmethyl)alaninamide;
$N^2$-[4-cyano-3-(trifluoromethyl)phenyl]-$N^2$-(cyclopropylmethyl)-$N^1$-methylalaninamide;
$N^2$-[4-cyano-3-(trifluoromethyl)phenyl]-$N^2$-(cyclopropylmethyl)-$N^1$-ethylalaninamide;
$N^2$-[4-cyano-3-(trifluoromethyl)phenyl]-$N^2$-(cyclopropylmethyl)-$N^1$,$N^1$-dimethylalaninamide;
4-[(cyanomethyl)(2,2,2-trifluoroethyl)amino]-2-(trifluoromethyl)benzonitrile;
4-[(1-cyanoethyl)(2,2,2-trifluoroethyl)amino]-2-(trifluoromethyl)benzonitrile;
methyl 3-[[4-cyano-3-(trifluoromethyl)phenyl](2,2,2-trifluoroethyl)amino]-2-methylpropanoate;
4-[(2-cyanopropyl)(2,2,2-trifluoroethyl)amino]-2-(trifluoromethyl)benzonitrile;
N-[4-cyano-3-(trifluoromethyl)phenyl]-N-(2,2-dimethylpropyl)glycine;
$N^2$-[4-cyano-3-(trifluoromethyl)phenyl]-$N^2$-(2,2-dimethylpropyl)glycinamide;
$N^2$-[4-cyano-3-(trifluoromethyl)phenyl]-$N^2$-(2,2,2-trifluoro-1-methylethyl)glycinamide;
$N^2$-[4-cyano-3-(trifluoromethyl)phenyl]-$N^2$-[1-(trifluoromethyl)propyl]glycinamide;
1,1-dimethylethyl N-[4-cyano-3-(trifluoromethyl)phenyl]-N-(3,3,3-trifluoropropyl)glycinate;
$N^2$-[4-cyano-3-(trifluoromethyl)phenyl]-$N^2$-(3,3,3-trifluoropropyl)glycinamide;
4-[(cyanomethyl)(3,3,3-trifluoropropyl)amino]-2-(trifluoromethyl)benzonitrile;
$N^2$-[4-cyano-3-(trifluoromethyl)phenyl]-$N^2$-(3,3,3-trifluoropropyl)alaninamide;
$N^2$-[4-cyano-3-(trifluoromethyl)phenyl]-$N^1$-methyl-$N^2$-(3,3,3-trifluoropropyl)alaninamide;
$N^2$-[4-cyano-3-(trifluoromethyl)phenyl]-$N^2$-(1,1-dimethylethyl)glycinamide;
$N^2$-[4-cyano-3-(trifluoromethyl)phenyl]-$N^2$-(1-methylethyl)glycinamide;
$N^2$-[4-cyano-3-(trifluoromethyl)phenyl]-$N^1$-methyl-$N^2$-(1-methylethyl)glycinamide;
4-[(cyanomethyl)(methyl)amino]-2-(trifluoromethyl)benzonitrile;
4-[(2-cyanoethyl)(methyl)amino]-2-(trifluoromethyl)benzonitrile;
1,1-dimethylethyl N-(3-chloro-4-cyanophenyl)-N-(2,2,2-trifluoroethyl)glycinate;
N-(3-chloro-4-cyanophenyl)-N-(2,2,2-trifluoroethyl)glycine;
$N^2$-(3-chloro-4-cyanophenyl)-$N^2$-(2,2,2-trifluoroethyl)glycinamide;
$N^2$-(3-chloro-4-cyanophenyl)-$N^1$-methyl-$N^2$-(2,2,2-trifluoroethyl)glycinamide;
$N^2$-(3-chloro-4-cyanophenyl)-$N^1$-ethyl-$N^2$-(2,2,2-trifluoroethyl)glycinamide;
1,1-dimethylethyl N-(3-chloro-4-cyanophenyl)-N-(2,2,2-trifluoroethyl)alaninate;
N-(3-chloro-4-cyanophenyl)-N-(2,2,2-trifluoroethyl)alanine;
$N^2$-(3-chloro-4-cyanophenyl)-$N^2$-(2,2,2-trifluoroethyl)alaninamide;
$N^2$-(3-chloro-4-cyanophenyl)-$N^1$-methyl-$N^2$-(2,2,2-trifluoroethyl)alaninamide;
$N^2$-(3-chloro-4-cyanophenyl)-$N^1$-ethyl-$N^2$-(2,2,2-trifluoroethyl)alaninamide;
1,1-dimethylethyl 2-[(3-chloro-4-cyanophenyl)(2,2,2-trifluoroethyl)amino]butanoate;
2-[(3-chloro-4-cyanophenyl)(2,2,2-trifluoroethyl)amino]butanamide;
2-[(3-chloro-4-cyanophenyl)(2,2,2-trifluoroethyl)amino]-N-methylbutanamide;
2-[(3-chloro-4-cyanophenyl)(2,2,2-trifluoroethyl)amino]-N-ethylbutanamide;
1,1-dimethylethyl N-(3-chloro-4-cyanophenyl)-N-(cyclopropylmethyl)glycinate;
N-(3-chloro-4-cyanophenyl)-N-(cyclopropylmethyl)glycine;
$N^2$-(3-chloro-4-cyanophenyl)-$N^2$-(cyclopropylmethyl)glycinamide;
$N^2$-(3-chloro-4-cyanophenyl)-$N^2$-(cyclopropylmethyl)-$N^1$-methylglycinamide;

N²-(3-chloro-4-cyanophenyl)-N²-(cyclopropylmethyl)-N¹-ethylglycinamide;
2-chloro-4-[(cyanomethyl)(cyclopropylmethyl)amino]benzonitrile;
1,1-dimethylethyl N-(3-chloro-4-cyanophenyl)-N-(cyclopropylmethyl)alaninate;
N-(3-chloro-4-cyanophenyl)-N-(cyclopropylmethyl)alanine;
N²-(3-chloro-4-cyanophenyl)-N²-(cyclopropylmethyl)alaninamide;
N²-(3-chloro-4-cyanophenyl)-N²-(cyclopropylmethyl)-N¹-methylalaninamide;
N²-(3-chloro-4-cyanophenyl)-N²-(cyclopropylmethyl)-N¹-ethylalaninamide;
1,1-dimethylethyl 2-[(3-chloro-4-cyanophenyl)(cyclopropylmethyl)amino]butanoate;
2-[(3-chloro-4-cyanophenyl)(cyclopropylmethyl)amino]butanoic acid;
2-[(3-chloro-4-cyanophenyl)(cyclopropylmethyl)amino]butanamide;
2-[(3-chloro-4-cyanophenyl)(cyclopropylmethyl)amino]-N-methylbutanamide;
2-[(3-chloro-4-cyanophenyl)(cyclopropylmethyl)amino]-N-ethyl butanamide;
methyl N-(3,4-dicyanophenyl)-N-(2,2,2-trifluoroethyl)glycinate;
1,1-dimethylethyl N-(3,4-dicyanophenyl)-N-(2,2,2-trifluoroethyl)glycinate;
N²-(3,4-dicyanophenyl)-N²-(2,2,2-trifluoroethyl)glycinamide;
N²-(3,4-dicyanophenyl)-N¹-methyl-N²-(2,2,2-trifluoroethyl)glycinamide;
N²-(3,4-dicyanophenyl)-N¹-ethyl-N²-(2,2,2-trifluoroethyl)glycinamide;
1,1-dimethylethyl N-(3,4-dicyanophenyl)-N-(2,2,2-trifluoroethyl)alaninate;
N-(3,4-dicyanophenyl)-N-(2,2,2-trifluoroethyl)alanine;
N²-(3,4-dicyanophenyl)-N²-(2,2,2-trifluoroethyl)alaninamide;
N²-(3,4-dicyanophenyl)-N¹-methyl-N²-(2,2,2-trifluoroethyl)alaninamide;
N²-(3,4-dicyanophenyl)-N¹-ethyl-N²-(2,2,2-trifluoroethyl)alaninamide;
1,1-dimethylethyl 2-[(3,4-dicyanophenyl)(2,2,2-trifluoroethyl)amino]butanoate;
2-[(3,4-dicyanophenyl)(2,2,2-trifluoroethyl)amino]butanoic acid;
2-[(3,4-dicyanophenyl)(2,2,2-trifluoroethyl)amino]butanamide;
2-[(3,4-dicyanophenyl)(2,2,2-trifluoroethyl)amino]-N-methylbutanamide;
2-[(3,4-dicyanophenyl)(2,2,2-trifluoroethyl)amino]-N-ethylbutanamide;
1,1-dimethylethyl N-(cyclopropylmethyl)-N-(3,4-dicyanophenyl)glycinate;
N-(cyclopropylmethyl)-N-(3,4-dicyanophenyl)glycine;
N²-(cyclopropylmethyl)-N²-(3,4-dicyanophenyl)glycinamide;
N²-(cyclopropylmethyl)-N²-(3,4-dicyanophenyl)-N¹-methylglycinamide;
N²-(cyclopropylmethyl)-N²-(3,4-dicyanophenyl)-N¹-ethylglycinamide;
4-[(cyanomethyl)(cyclopropylmethyl)amino]-1,2-benzenedicarbonitrile;
1,1-dimethylethyl N-(cyclopropylmethyl)-N-(3,4-dicyanophenyl)alaninate;
N-(cyclopropylmethyl)-N-(3,4-dicyanophenyl)alanine;
N²-(cyclopropylmethyl)-N²-(3,4-dicyanophenyl)-N¹-methylalaninamide;
N²-(cyclopropylmethyl)-N²-(3,4-dicyanophenyl)-N¹-ethylalaninamide;
1,1-dimethylethyl 2-[(cyclopropylmethyl)(3,4-dicyanophenyl)amino]butanoate;
2-[(cyclopropylmethyl)(3,4-dicyanophenyl)amino]butanoic acid;
2-[(cyclopropylmethyl)(3,4-dicyanophenyl)amino]butanamide;
2-[(cyclopropylmethyl)(3,4-dicyanophenyl)amino]-N-methylbutanamide; and 2-[(cyclopropylmethyl)(3,4-dicyanophenyl)amino]-N-ethylbutanamide.

Abbreviations

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

g (grams);
L (liters);
μL (microliters);
M (molar);
Hz (Hertz);
mol (moles);
rt (room temperature);
h (hours);
TLC (thin layer chromatography);
$T_r$ (retention time);
TEA (triethylamine);
TFAA (trifluoroacetic anhydride);
$CDCl_3$ (deuterated chloroform);
$SiO_2$ (silica);
EtOAc (ethyl acetate);
HCl (hydrochloric acid);
DMF (N,N-dimethylformamide);
$Cs_2CO_3$ (cesium carbonate);
Et (ethyl);
MeOH (methanol);
IPA (isopropyl alcohol);
DIEA (diisopropyl ethylamine);
mg (milligrams);
mL (milliliters);
psi (pounds per square inch);
mM (millimolar);
MHz (megahertz);
mmol (millimoles);
min (minutes);
mp (melting point);
$CH_2Cl_2$ (methylene chloride);
RP (reverse phase);
TFA (trifluoroacetic acid);
THF (tetrahydrofuran);
$CD_3OD$ (deuterated methanol);
DMSO (dimethylsulfoxide);
atm (atmosphere);
$CHCl_3$ (chloroform);
Ac (acetyl);
Me (methyl);
EtOH (ethanol);
t-Bu (tert-butyl)
NMO (4-methylmorpholine N-oxide);
DCE (1,2-dichloroethane).

Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or b (broad).

Scheme 1

Method A

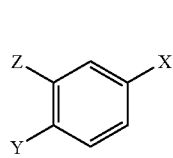 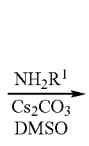 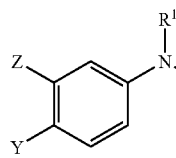

Method B

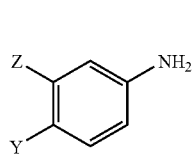 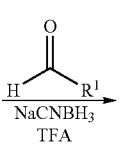 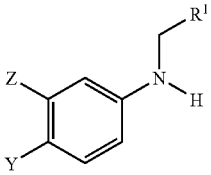

Method C

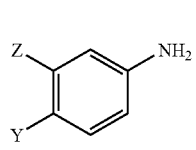 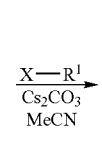 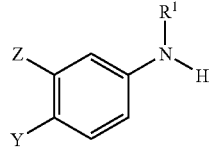

X = F, Cl, Br, OTf, etc.
Y = CN, NO$_2$
Z = CF$_3$, CN, halogen, etc.

The secondary anilines required for the synthesis of compounds of formula (I) can be prepared by three different methods (Scheme 1). As exemplified by method A, electron deficient arenes are treated with primary amines, a non-limiting example is 1-cyclopropylmethanamine, in the presence of a base, a non-limiting example of which is potassium carbonate, to afford the corresponding aniline. A second method of synthesizing the requisite secondary anilines is by reductive alkylation of primary anilines using aldehydes or hydrates, a non-limiting example of which is trifluoroacetaldehyde hydrate, and reducing agents, a non-limiting example of which is sodium cyanoborohydride, in the presence of acid such as TFA (method B). The third method of secondary aniline synthesis, method C, involves alkylation of primary anilines with alkyl halides, a non-limiting example of which is 1-bromo-2-fluoroethane, in the presence of base, a non-limiting example of which is cesium carbonate.

Scheme 2

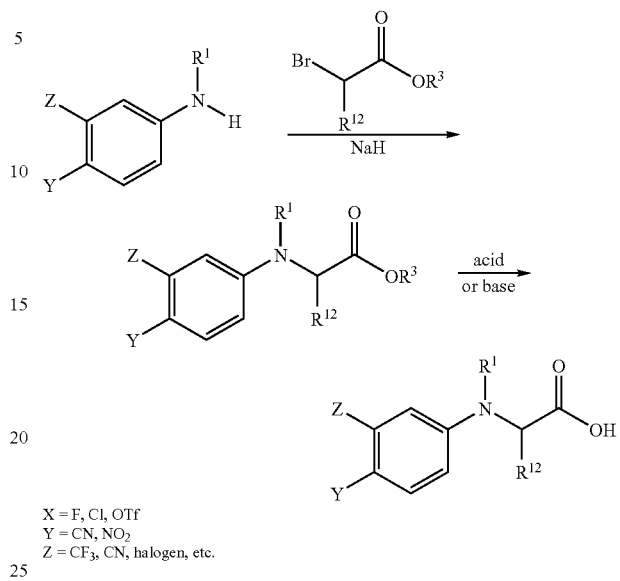

X = F, Cl, OTf
Y = CN, NO$_2$
Z = CF$_3$, CN, halogen, etc.

The next step in the synthesis of compounds of formula (I) is accomplished by alkylation of secondary anilines with α-haloesters, a non-limiting example of which is t-butyl-bromo acetate (Scheme 2). Deprotection with acid or saponification with base affords the corresponding carboxylic acid, which is then coupled with amines by three methods. When alkyl substituted amines are used, a non-limiting example of which is methylamine, then coupling is accomplished with coupling agents, a non-limiting example of which is DCC (Scheme 3, method A). Primary amides are afforded by activation of the corresponding carboxylic acids with di-tert-butylcarbonate followed by treatment with ammonium bicarbonate (Scheme 3, method B). Another method used to generate amides is through synthesis of acid chlorides followed by treatment with amines (Scheme 3, method C).

Scheme 3

Method A

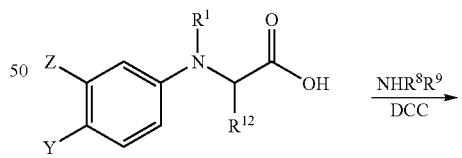

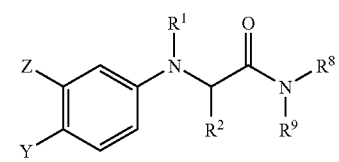

Method B

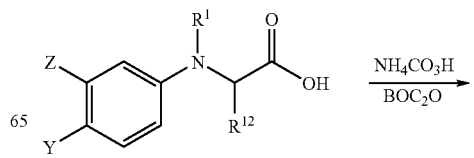

-continued

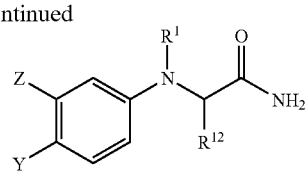

Method C

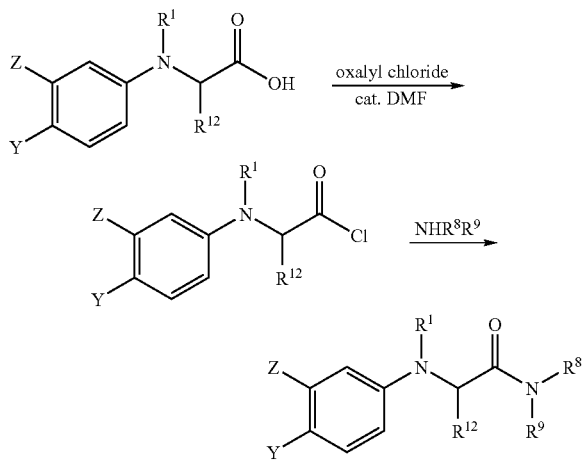

Y = CN, NO$_2$
Z = CF$_3$, CN, halogen, etc.

EXAMPLES

Representative Procedure for Secondary Aniline Synthesis
Method A

Example 1

1,1-Dimethylethyl N-[4-cyano-3-(trifluoromethyl)phenyl]-N-(cyclopropylmethyl)glycinate

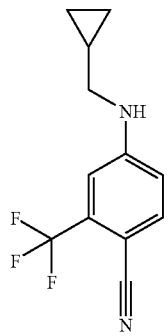

A. 4-[(Cyclopropylmethyl)amino]-2-(trifluoromethyl)benzonitrile

A mixture of 4-fluoro-2-(trifluoromethyl)benzonitrile (9.45 g, 50 mmol), 1-cyclopropylmethanamine (5.0 g, 70 mmol), and potassium carbonate (10 g) was stirred for 12 hours in acetonitrile (50 mL) at 55° C. The mixture was cooled to 20° C., filtered, and the filter-cake was washed with acetonitrile (3×25 mL). The filtrate was concentrated under vacuum to obtain 11.9 g (99%) of the title compound as a white solid: $^1$H NMR (400 MHz, CDCl$_3$) δ 7.53 (d, J=8.6 Hz, 1H), 6.83 (d, J=2.4 Hz, 1H), 6.65 (dd, J=8.6, 2.4 Hz, 1H), 4.62 (bs, 1H), 3.02 (d, J=7.1 Hz, 2H), 1.09 (m, 1H), 0.61 (m, 2H), 0.27 (m, 2H).

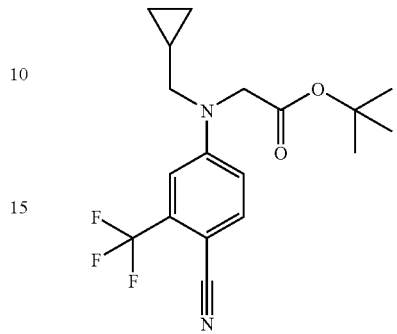

B. 1,1-Dimethylethyl N-[4-cyano-3-(trifluoromethyl)phenyl]-N-(cyclopropylmethyl)glycinate Sodium hydride (60%, 2.0 g, 50 mmol) was added to a stirred solution of 4-[(cyclopropylmethyl)amino]-2-(trifluoromethyl)benzonitrile (6.0 g, 25 mmol), and tert-butyl bromoacetate (6.82 g, 35 mmol) in 20 mL of DMF at 0° C. over 20 minutes. The mixture was then stirred at 5-10° C. for 30 minutes. Diethyl ether (200 mL) was added to the mixture and the resulting slurry was extracted with water (3×50 mL). The organic phase was dried (MgSO$_4$), filtered, and then concentrated under reduced pressure. The residue was purified with silica gel chromatography (eluent: hexane-EtOAc; 3:1) to obtain 6.55 g (74%) of the title compound as a white solid: $^1$H NMR (400 MHz, CDCl$_3$) δ 7.59 (d, J=8.8 Hz, 1H), 6.92 (d, J=2.6 Hz, 1H), 6.77 (dd, J=8.8, 2.7 Hz, 1H), 4.10 (s, 2H), 3.33 (d, J=6.6 Hz, 2H), 1.43 (s, 9H), 1.05 (m, 1H), 0.62 (m, 2H), 0.26 (m, 2H).

Example 2

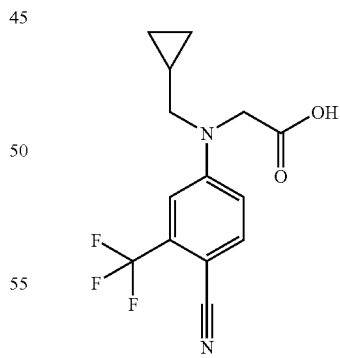

N-[4-Cyano-3-(trifluoromethyl)phenyl]-N-(cyclopropylmethyl)glycine

A mixture of 1,1-dimethylethyl N-[4-cyano-3-(trifluoromethyl)phenyl]-N-(cyclopropylmethyl)glycinate (5.01 g, 14.1 mmol), TFA (50 mL), and triethylsilane (5 mL) in CH$_2$Cl$_2$ (50 mL) was stirred at ambient temperature for 3 h. When the TLC indicated no remaining starting material, the solvents were removed under reduced pressure, and the residue was stirred in hexane (50 mL) for 12 hours. The solid precipitate was filtered and dried to obtain 2.9 g (71%) of the title compound as a white solid: $^1$H NMR (400 MHz, CDCl$_3$) δ 7.61 (d, J=8.8 Hz, 1H), 6.97 (d, J=2.8 Hz, 1H), 6.78 (dd, J=8.8, 2.8 Hz, 1H), 4.29 (s, 2H), 3.34 (d, J=6.4 Hz, 2H), 1.37 (m, 1H), 0.64 (m, 2H), 0.27 (m, 2H).

Representative Procedure for Coupling Method A

Example 3

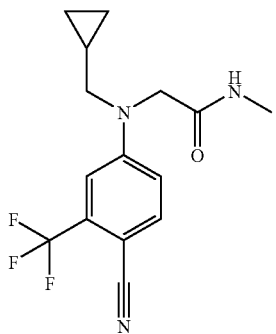

N$^2$-[4-Cyano-3-(trifluoromethyl)phenyl]-N$^2$-(cyclopropyl methyl)-N$^1$-methylglycinamide A mixture of N-[4-cyano-3-(trifluoromethyl)phenyl]-N-(cyclopropyl-methyl)glycine (0.148 g, 0.5 mmol), and resin bounded carbodiimide (PS-Carbodiimide) (1.0 g, 1.26 mmol/g) was shaken in CH$_2$Cl$_2$ (15 mL) for 30 min, then methylamine (33% solution in water, 0.1 mL, 1 mmol) was added, and the mixture was shaken for another 12 h. The resin was filtered and washed with CH$_2$Cl$_2$ (2×10 mL). The resulting filtrate was concentrated under vacuum. The residue was purified via preparative HPLC to obtain 0.036 g (23%) of the title compound as a white foam: $^1$H NMR (400 MHz, CDCl$_3$) δ 7.54 (d, J=8.5 Hz, 1H), 6.99 (bs, 1H), 6.89 (dd, J=8.8, 2.6 Hz, 1H), 6.28 (bs, 1H), 4.08 (s, 2H), 3.34 (d, J=6.6 Hz, 2H), 2.80 (d, J=4.7 Hz, 3H), 1.06 (m, 1H), 0.65 (m, 2H), 0.31 (m, 2H).

Representative Procedure for Coupling Method B

Example 4

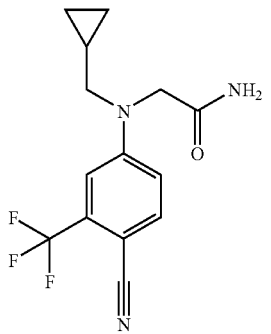

N$^2$-[4-Cyano-3-(trifluoromethyl)phenyl]-N$^2$-(cyclopropyl methyl)glycinamide

A mixture of N-[4-cyano-3-(trifluoromethyl)phenyl]-N-(cyclopropylmethyl)glycine (0.298 g, 1 mmol), di-tert-butyl dicarbonate (0.436 g, 2 mmol), pyridine (0.100 g, 1.25 mmol), and ammonium hydrocarbonate (0.160 g, 2.25 mmol) was stirred for 24 h in acetonitrile (8 mL). The solvent was removed under reduced pressure, then water (10 mL) was added to the residue. The resulting solid was filtered, washed with water (3×5 mL), and then dried. After drying, the solid was suspended in diethyl ether (10 mL) and stirred for 12 h. The mixture was filtered, washed with diethyl ether (5 mL), and dried to obtain 0.118 g (40%) of the title compound as a white solid: $^1$H NMR (400 MHz, CDCl$_3$) δ 7.63 (d, J=8.6 Hz, 1H), 7.03 (d, J=2.3 Hz, 1H), 6.84 (dd, J=8.8, 2.5 Hz, 1H), 6.02 (bs, 1H), 5.57 (bs, 1H), 4.10 (s, 2H), 3.38 (d, J=6.6 Hz, 2H), 1.08 (m, 1H), 0.67 (m, 2H), 0.33 (m, 2H).

Example 5

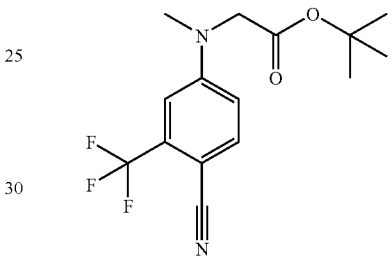

1,1-Dimethylethyl N-[4-cyano-3-(trifluoromethyl)phenyl]-N-methylglycinate

Synthesized as described in step B of example 1 using 4-(methylamino)-2-(trifluoromethyl)benzonitrile: $^1$H NMR (400 MHz, CDCl$_3$) δ 7.60 (d, J=8.8 Hz, 1H), 6.88 (d, J=2.6 Hz, 1H), 6.74 (dd, J=8.8, 2.7 Hz, 1H), 4.02 (s, 2H), 3.15 (s, 3H), 1.44 (s, 9H).

Example 6

1,1-Dimethylethyl N-[4-cyano-3-(trifluoromethyl)phenyl]-N-ethylglycinate

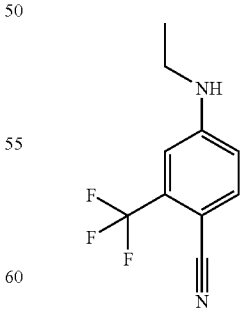

A. 4-(Ethylamino)-2-(trifluoromethyl)benzonitrile

Synthesized as described in step A of example 1 using ethylamine: $^1$H NMR (400 MHz, CDCl$_3$) δ 7.53 (d, J=8.4 Hz, 1H), 6.82 (d, J=2.2 Hz, 1H), 6.65 (dd, J=8.6, 2.4 Hz, 1H), 4.42 (bs, 1H), 3.23 (q, J=7.2 Hz, 2H), 1.29 (t, J=7.2 Hz, 3H).

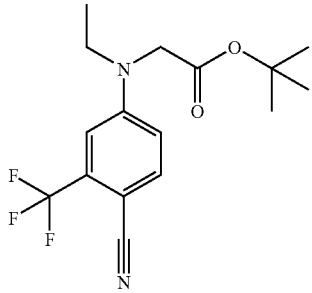

B. 1,1-Dimethylethyl N-[4-cyano-3-(trifluoromethyl)phenyl]-N-ethylglycinate

Synthesized as described in example 1 using 4-(ethylamino)-2-(trifluoromethyl)benzonitrile: $^1$H NMR (400 MHz, CDCl$_3$) δ 7.58 (d, J=8.8 Hz, 1H), 6.83 (s, 1H), 6.70 (dd, J=9.0, 2.4 Hz, 1H), 3.98 (s, 2H), 3.52 (q, J=7.2 Hz, 2H), 1.44 (s, 9H), 1.24 (t, J=7.2 Hz, 3H).

Example 7

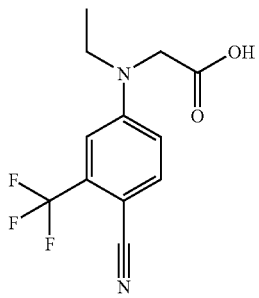

N-[4-Cyano-3-(trifluoromethyl)phenyl]-N-ethylglycine

Synthesized as described in example 2 using 1,1-dimethylethyl N-[4-cyano-3-(trifluoromethyl)phenyl]-N-ethylglycinate: $^1$H NMR (400 MHz, CDCl$_3$) δ 7.60 (d, J=8.7 Hz, 1H), 6.89 (d, J=2.6 Hz, 1H), 6.72 (dd, J=8.7, 2.7 Hz, 1H), 4.16 (s, 2H), 3.53 (q, J=7.1 Hz, 2H), 1.24 (t, J=7.0 Hz, 3H).

Example 8

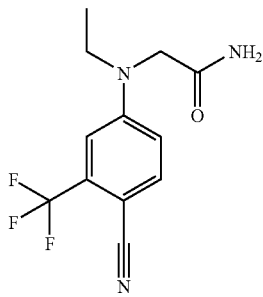

$N^2$-[4-Cyano-3-(trifluoromethyl)phenyl]-$N^2$-ethylglycinamide

Synthesized as described in example 4 using N-[4-cyano-3-(trifluoromethyl)phenyl]-N-ethylglycine: $^1$H NMR (400 MHz, DMSO-d$_6$) δ 7.76 (d, J=8.6 Hz, 1H), 7.49 (bs, 1H), 7.18 (bs, 1H), 6.88 (s, 1H), 6.87 (d, J=9.3 Hz, 1H), 4.01 (s, 2H), 3.49 (q, J=6.9 Hz, 2H), 1.08 (t, J=6.9 Hz, 3H).

Example 9

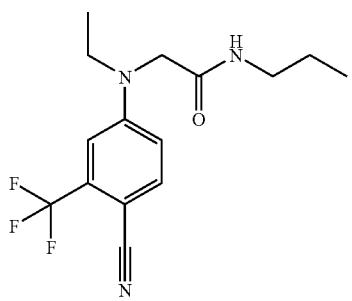

$N^2$-[4-Cyano-3-(trifluoromethyl)phenyl]-$N^2$-ethyl-$N^1$-propylglycinamide

Synthesized as described in example 3 using N-[4-cyano-3-(trifluoromethyl)phenyl]-N-ethylglycine and propylamine: $^1$H NMR (400 MHz, CDCl$_3$) δ 7.63 (d, J=8.8 Hz, 1H), 6.95 (d, J=2.3 Hz, 1H), 6.77 (dd, J=8.8, 2.4 Hz, 1H), 5.99 (bs, 1H), 3.96 (s, 2H), 3.54 (q, J=7.1 Hz, 2H), 3.47 (q, J=7.0 Hz, 2H), 1.46 (m, 2H), 1.25 (t, J=7.1 Hz, 3H), 0.83 (t, J=7.3 Hz, 3H).

Example 10

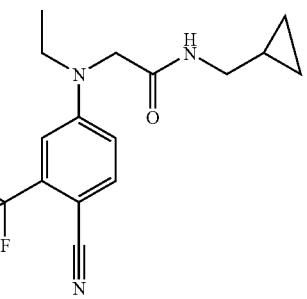

$N^2$-[4-Cyano-3-(trifluoromethyl)phenyl]-$N^1$-(cyclopropyl methyl)-$N^2$-ethylglycinamide Synthesized as described in example 3 using N-[4-cyano-3-(trifluoromethyl)phenyl]-N-ethylglycine and 1-cyclopropylmethanamine: $^1$H NMR (400 MHz, CDCl$_3$) δ 7.63 (d, J=8.8 Hz, 1H), 6.96 (d, J=2.6 Hz, 1H), 6.79 (dd, J=8.8, 2.8 Hz, 1H), 6.06 (bs, 1H), 3.97 (s, 2H), 3.56 (q, J=7.1 Hz, 2H), 3.13

(t, J=6.3 Hz, 2H), 1.26 (t, J=7.1 Hz, 3H), 0.87 (m, 1H), 0.45 (m, 2H), 0.14 (m, 2H).

Example 11

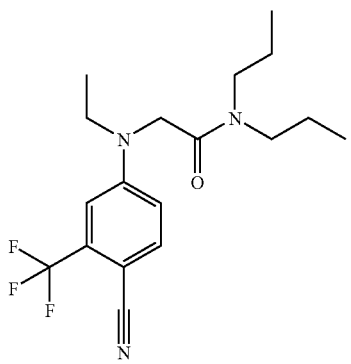

N²-[4-Cyano-3-(trifluoromethyl)phenyl]-N²-ethyl-N¹,N¹-dipropylglycinamide

Synthesized as described in example 3 using N-[4-cyano-3-(trifluoromethyl)phenyl]-N-ethylglycine and dipropylamine: ¹H NMR (400 MHz, CDCl₃) δ 7.55 (d, J=9.0 Hz, 1H), 6.76 (d, J=2.5 Hz, 1H), 6.65 (dd, J=8.8, 2.5 Hz, 1H), 4.14 (s, 2H), 3.51 (m, 2H), 3.31 (t, J=7.5 Hz, 2H), 3.25 (t, J=6.7 Hz, 2H), 1.63 (m, 4H), 1.25 (t, J=7.1 Hz, 3H), 1.00 (t, J=7.3 Hz, 3H), 0.88 (t, J=7.4 Hz, 3H).

Representative Procedure for Secondary Aniline Synthesis Method B

Example 12

1,1-Dimethylethyl N-[4-cyano-3-(trifluoromethyl)phenyl]-N-(2,2,2-trifluoroethyl)glycinate

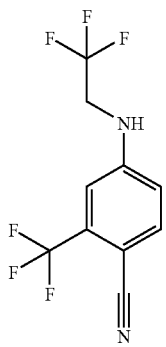

A. 4-[(2,2,2-Trifluoroethyl)amino]-2-(trifluoromethyl)benzonitrile

To a slurry of 4-amino-2-(trifluoromethyl)benzonitrile (30.09 g, 162 mmol) and NaBH₃CN (21.35 g, 340 mmol) in CH₂Cl₂ (160 mL) at ice bath temperature was added neat TFA (160 mL, 2.08 mol), dropwise at a rate such that the internal temperature remained below 5° C. (CAUTION: exothermic reaction with hydrogen gas evolution). Trifluoroacetaldehyde hydrate (52.2 g; 405 mmol) was then added over 5 minutes (CAUTION: slightly exothermic reaction, with gas evolution). After 41 h, the mixture was slowly poured into satd NaHCO₃ (1 L) at 0° C. The mixture was then completely neutralized by portionwise addition of solid NaHCO₃. The mixture was stirred 30 min and precipitated solids were collected by filtration. Organic and aqueous phases of the filtrate were separated, and the aqueous layer was extracted with CH₂Cl₂ (3×150 mL). Combined organic extracts were concentrated to dryness, combined with the solids collected previously, dissolved in EtOAc, washed (H₂O, brine), dried over Na₂SO₄, filtered through a short pad of Celite and concentrated to dryness. Recrystallization from EtOAc/hexanes yielded 32.61 g (95%) of the title compound as slightly tan crystalline plates: ¹H NMR (300 MHz, CD₃OD) δ 7.59 (d, J=8.8 Hz, 1H), 7.05 (d, J=2.2 Hz, 1H), 6.92 (dd, J=8.7, 2.4 Hz, 1H), 3.92 (q, J=9.2 Hz, 2H).

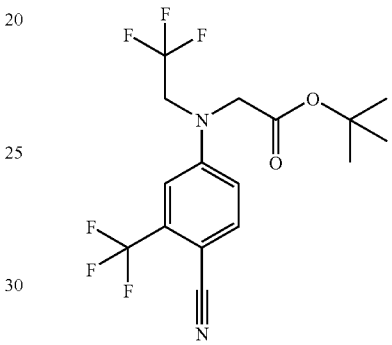

B. 1,1-Dimethylethyl N-[4-cyano-3-(trifluoromethyl)phenyl]-N-(2,2,2-trifluoroethyl)glycinate Synthesized according to step B of example 1 using 4-[(2,2,2-trifluoroethyl)amino]-2-(trifluoromethyl)benzonitrile: ¹H NMR (300 MHz, CD₃OD) δ 7.70 (d, J=8.8 Hz, 1H), 7.01-7.09 (m, 2H), 4.26 (q, J=8.9 Hz, 2H), 4.23 (s, 2H, overlapped with 4.26), 1.44 (s, 9H).

Example 13

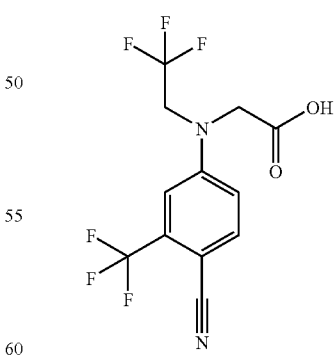

N-[4-Cyano-3-(trifluoromethyl)phenyl]-N-(2,2,2-trifluoroethyl)glycine

Synthesized in a manner similar to example 2 using 1,1-dimethylethyl N-[4-cyano-3-(trifluoromethyl)phenyl]-N-(2, 2,2-trifluoroethyl)glycinate: ¹H NMR (300 MHz, CD₃OD) δ 7.67 (d, J=8.6 Hz, 1H), 7.07 (d, J=2.8 Hz, 1H), 7.03 (dd, J=8.6, 2.8 Hz, 1H), 4.28 (s, overlapped with 4.24, 2H), 4.24 (q, J=8.8 Hz, 2H).

CDCl₃) δ 7.69 (d, J=8.8 Hz, 1H), 7.01 (d, J=2.4 Hz, 1H), 6.88 (dd, J=8.8, 2.6 Hz, 1H), 4.24 (s, 2H), 4.06 (q, J=8.5 Hz, 2H), 3.81 (s, 3H).

Example 14

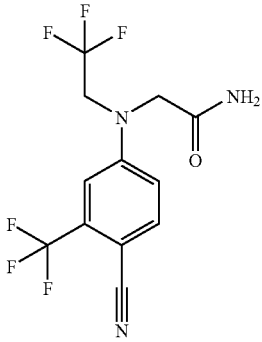

N²-[4-Cyano-3-(trifluoromethyl)phenyl]-N²-(2,2,2-trifluoroethyl)glycinamide

Synthesized in a manner similar to example 4 N-[4-cyano-3-(trifluoromethyl)phenyl]-N-(2,2,2-trifluoroethyl)glycine: ¹H NMR (300 MHz, CD₃OD) δ 7.72 (d, J=8.6 Hz, 1H), 7.15 (d, J=2.5 Hz, 1H), 7.11 (dd, J=8.8, 2.5 Hz, 1H), 4.34 (q, J=8.9 Hz, 2H), 4.27 (s, 2H).

Example 16

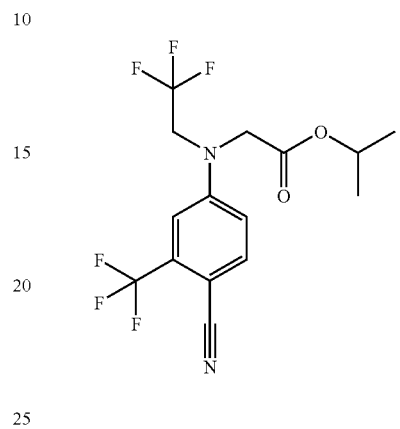

1-Methylethyl N-[4-cyano-3-(trifluoromethyl)phenyl]-N-(2,2,2-trifluoroethyl)glycinate Synthesized according to example 3 N-[4-cyano-3-(trifluoromethyl)phenyl]-N-(2,2,2-trifluoroethyl)glycine and isopropanol: ¹H NMR (300 MHz, CD₃OD) δ 7.81-7.73 (m, 1H), 7.17-7.09 (m, 2H), 5.04 (sept, J=6.3 Hz, 1H), 4.38 (s, 2H, overlapped with 4.35), 4.35 (q, J=9.0 Hz, overlapped with 4.38, 2H), 1.23 (d, J=6.1 Hz, 6H).

Example 15

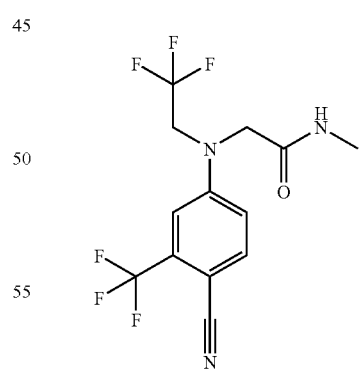

Methyl N-[4-cyano-3-(trifluoromethyl)phenyl]-N-(2,2,2-trifluoroethyl)glycinate

Synthesized in a manner similar to step B of example 1 using 4-[(2,2,2-trifluoroethyl)amino]-2-(trifluoromethyl)benzonitrile and methyl bromoacetate: ¹H NMR (400 MHz,

Example 17

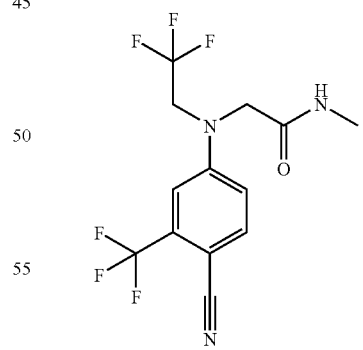

N²-[4-Cyano-3-(trifluoromethyl)phenyl]-N¹-methyl-N²-(2,2,2-trifluoroethyl)glycinamide Synthesized as described in example 3 using N-[4-cyano-3-(trifluoromethyl)phenyl]-N-(2,2,2-trifluoroethyl)glycine: ¹H NMR (400 MHz, CDCl₃) δ 7.68 (d, J=8.8 Hz, 1H), 7.04 (d, J=2.5 Hz, 1H), 6.90 (dd, J=8.8, 2.8 Hz, 1H), 5.80 (bs, 1H), 4.13 (s, 2H), 4.08 (q, J=8.6 Hz, 2H), 2.85 (d, J=4.8 Hz, 3H).

1H), 5.81 (d, J=8.0 Hz, 1H), 4.12 (s, 2H), 4.10 (q, J=8.6 Hz, 2H), 3.80 (m, 1H), 1.83 (m, 2H), 1.63 (m, 3H), 1.32 (m, 2H), 1.08 (m, 3H).

Example 18

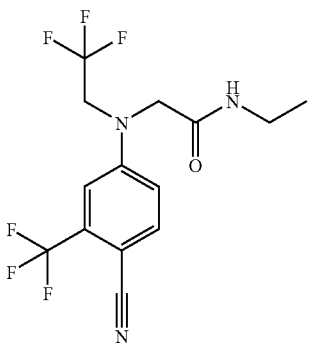

$N^2$-[4-Cyano-3-(trifluoromethyl)phenyl]-$N^1$-ethyl-$N^2$-(2,2,2-trifluoroethyl)glycinamide Synthesized as described in example 3 using N-[4-cyano-3-(trifluoromethyl)phenyl]-N-(2,2,2-trifluoroethyl)glycine and ethylamine: $^1$H NMR (400 MHz, CDCl$_3$) δ 7.68 (d, J=8.6 Hz, 1H), 7.03 (d, J=2.7 Hz, 1H), 6.91 (dd, J=8.8, 2.7 Hz, 1H), 5.78 (bs, 1H), 4.10 (s, 2H), 4.08 (q, J=8.6 Hz, 2H), 3.32 (m, 2H), 1.11 (t, J=7.3 Hz, 3H).

Example 19

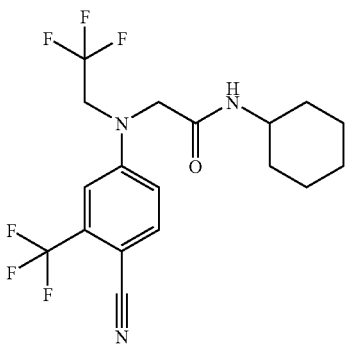

$N^2$-[4-Cyano-3-(trifluoromethyl)phenyl]-$N^1$-cyclohexyl-$N^2$-(2,2,2-trifluoroethyl)glycinamide Synthesized as described in example 3 using N-[4-cyano-3-(trifluoromethyl)phenyl]-N-(2,2,2-trifluoroethyl)glycine and cyclohexylamine: $^1$H NMR (400 MHz, CDCl$_3$) δ 7.68 (d, J=8.8 Hz, 1H), 7.03 (d, J=2.6 Hz, 1H), 6.92 (dd, J=8.8, 2.7 Hz, Example 20

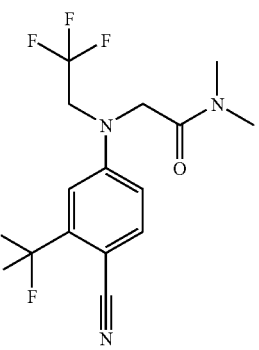

$N^2$-[4-Cyano-3-(trifluoromethyl)phenyl]-$N^1$,$N^1$-dimethyl-$N^2$-(2,2,2-trifluoroethyl)glycinamide Synthesized as described in example 3 using N-[4-cyano-3-(trifluoromethyl)phenyl]-N-(2,2,2-trifluoroethyl)glycine and dimethylamine: $^1$H NMR (400 MHz, CDCl$_3$) δ 7.63 (d, J=8.7 Hz, 1H), 6.94 (d, J=2.8 Hz, 1H), 6.80 (dd, J=8.8, 2.8 Hz, 1H), 4.27 (s, 2H), 4.01 (q, J=8.8 Hz, 2H), 3.10 (s, 3H), 3.01 (s, 3H).

Example 21

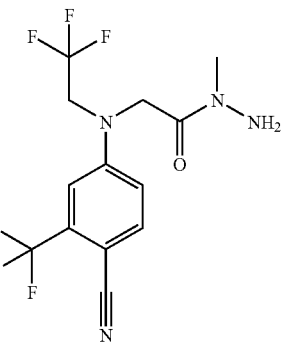

2-[4-Cyano(2,2,2-trifluoroethyl)-3-(trifluoromethyl) anilino]-N-methylacetohydrazide Synthesized as described in example 3 using N-[4-cyano-3-(trifluoromethyl)phenyl]-N-(2,2,2-trifluoroethyl)glycine and methylhydrazine: $^1$H NMR (400 MHz, CDCl$_3$) δ 7.62 (d, J=8.8 Hz, 1H), 6.97 (d, J=2.6 Hz, 1H), 6.83 (dd, J=8.8, 2.8 Hz, 1H), 4.62 (s, 2H), 4.25 (bs, 2H), 4.02 (q, J=8.6 Hz, 2H), 3.24 (s, 3H).

(dd, J=8.8, 2.7 Hz, 1H), 4.5 (q, J=7.3 Hz, 1H), 4.02-4.13 (m, 2H), 3.74 (s, 3H), 1.64 (d, J=7.1 Hz, 3H).

Example 22

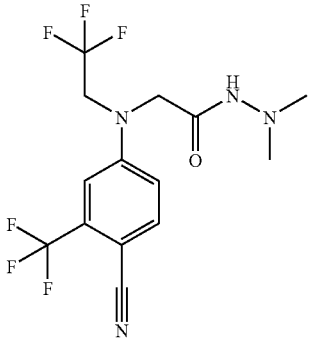

2-[4-Cyano(2,2,2-trifluoroethyl)-3-(trifluoromethyl) anilino]-N',N'-dimethylacetohydrazide Synthesized as described in example 3 using N-[4-cyano-3-(trifluoromethyl)phenyl]-N-(2,2,2-trifluoroethyl)glycine and 1,1-dimethylhydrazine: $^1$H NMR (400 MHz, CD$_3$OD) δ 7.77 (d, J=9.6 Hz, 1H), 7.14 (bs, 2H), 7.08 (s, 1H), 4.36 (q, J=9.0 Hz, 2H), 4.26 (s, 2H), 2.69 (s, 3H), 2.61 (s, 3H).

Example 23

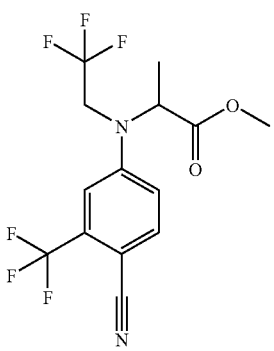

Methyl N-[4-cyano-3-(trifluoromethyl)phenyl]-N-(2,2,2-trifluoroethyl)alaninate

Synthesized according to step B of example 1 using 4-[(2,2,2-trifluoroethyl)amino]-2-(trifluoromethyl)benzonitrile and methyl 2-bromopropanoate: $^1$H NMR (400 MHz, CDCl$_3$) δ 7.66 (d, J=8.8 Hz, 1H), 7.1 (d, J=2.7 Hz, 1H), 6.95

Example 24

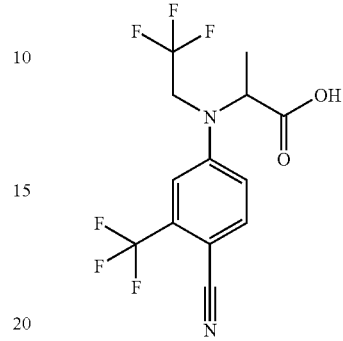

(N-[4-Cyano-3-(trifluoromethyl)phenyl]-N-(2,2,2-trifluoroethyl)alanine

To a solution of methyl N-[4-cyano-3-(trifluoromethyl)phenyl]-N-(2,2,2-trifluoroethyl)alaninate (0.034 g, 0.11 mmol) in THF:methanol (1:1; 3 mL) was added 1N NaOH (1.1 ml, 1.1 mmol). The solution was heated at 60° C. for 30 min. Upon cooling, the solution was treated with 1N HCl (5 mL) and partitioned between ethyl acetate and saturated brine. The organic phase was washed with brine, dried (Na$_2$SO$_4$), and concentrated in vacuo to give 0.031 g (100% yield) of the desired product as a white solid: $^1$H NMR (400 MHz, CDCl$_3$) δ 7.69 (d, J=8.8 Hz, 1H), 7.13 (d, J=2.7 Hz, 1H), 6.98 (dd, J=8.8, 2.7 Hz, 1H), 4.55 (q, J=7.2 Hz, 1H), 4.17-4.01 (m, 2H), 1.69 (d, J=7.2 Hz, 3H).

Example 25

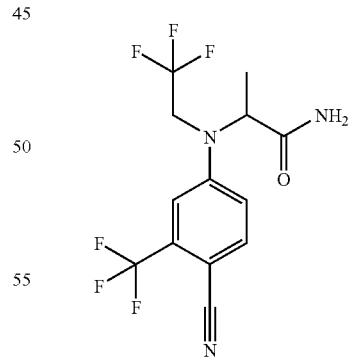

$N^2$-[4-Cyano-3-(trifluoromethyl)phenyl]-$N^2$-(2,2,2-trifluoroethyl)alaninamide Synthesized according to example 4 using N-[4-cyano-3-(trifluoromethyl)phenyl]-N-(2,2,2-trifluoroethyl)alanine: $^1$H NMR (400 MHz, CDCl$_3$) δ 7.66 (d, J=8.8 Hz, 1H), 7.13 (d, J=2.6 Hz, 1H), 6.99 (dd, J=8.8, 2.6 Hz, 1H), 6.0 (bs, 1H), 5.76 (bs, 1H), 4.34 (q, J=7.1 Hz, 1H), 4.16-4.03 (m, 2H), 1.61 (d, J=7.1 Hz, 3H).

Example 26

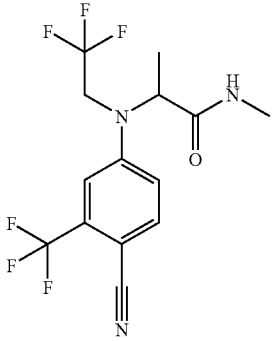

N²-[4-Cyano-3-(trifluoromethyl)phenyl]-N¹-methyl-N²-(2,2,2-trifluoroethyl)alaninamide Synthesized in a manner similar to example 3 using N-[4-cyano-3-(trifluoromethyl)phenyl]-N-(2,2,2-trifluoroethyl)alanine: ¹H NMR (400 MHz, CDCl₃) δ 7.65 (d, J=8.8 Hz, 1H), 7.1 (d, J=2.6 Hz, 1H), 6.95 (dd, J=8.8, 2.8 Hz, 1H), 5.95 (bq, 1H), 4.28 (q, J=7.1 Hz, 1H), 4.17-4.02 (m, 2H), 2.81 (d, J=4.8 Hz, 3H), 1.59 (d, J=7.1 Hz, 3H).

Example 27

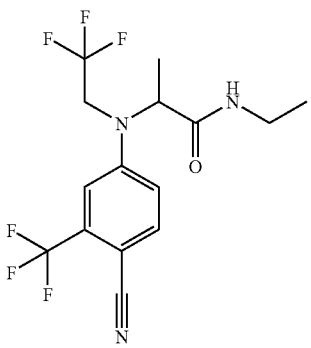

N²-[4-Cyano-3-(trifluoromethyl)phenyl]-N¹-ethyl-N²-(2,2,2-trifluoroethyl)alaninamide Synthesized as described in example 3 using N-[4-cyano-3-(trifluoromethyl)phenyl]-N-(2,2,2-trifluoroethyl)alanine and ethylamine: ¹H NMR (400 MHz, CDCl₃) δ 7.65 (d, J=8.8 Hz, 1H), 7.10 (d, J=2.7 Hz, 1H), 6.96 (dd, J=8.8, 2.8 Hz, 1H), 5.95 (bs, 1H), 4.26 (q, J=7.1 Hz, 1H), 4.10 (m, 2H), 3.28 (m, 2H), 1.58 (d, J=7.1 Hz, 3H), 1.06 (t, J=7.4 Hz, 3H).

Example 28

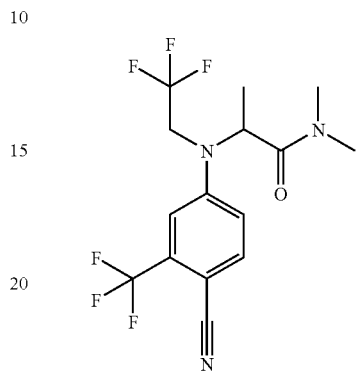

N²-[4-Cyano-3-(trifluoromethyl)phenyl]-N¹,N¹-dimethyl-N²-(2,2,2-trifluoroethyl)alaninamide Synthesized as described in example 3 using N-[4-cyano-3-(trifluoromethyl)phenyl]-N-(2,2,2-trifluoroethyl)alanine and dimethylamine: ¹H NMR (400 MHz, CDCl₃) δ 7.69 (d, J=8.8 Hz, 1H), 7.10 (d, J=2.7 Hz, 1H), 7.01 (dd, J=9.0, 2.7 Hz, 1H), 4.80 (q, J=7.0 Hz, 1H), 4.30 (m, 2H), 3.07 (s, 3H), 2.96 (s, 3H), 1.48 (d, J=7.0 Hz, 3H).

Example 29

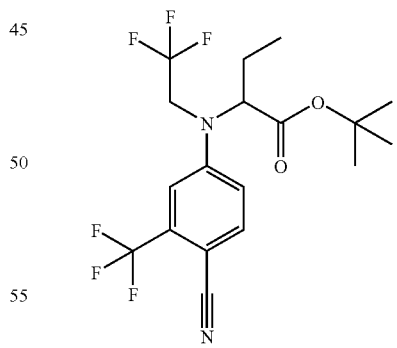

1,1-Dimethylethyl 2-[[4-cyano-3-(trifluoromethyl)phenyl](2,2,2-trifluoroethyl)amino]butanoate Synthesized as described in step B of example 1 using 4-[(2,2,2-trifluoroethyl)amino]-2-(trifluoromethyl)benzonitrile and tert-butyl 2-bromobutanoate: ¹H NMR (400 MHz, CDCl₃) δ 7.66 (d, J=8.8 Hz, 1H), 7.14 (d, J=2.7 Hz, 1H), 7.00

(dd, J=8.8, 2.8 Hz, 1H), 4.05 (m, 3H), 2.12 (m, 1H), 1.93 (m, 1H), 1.41 (s, 9H), 1.02 (t, J=7.5 Hz, 3H).

Example 30

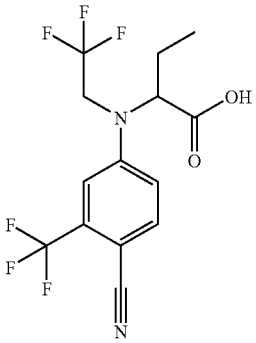

2-[[4-Cyano-3-(trifluoromethyl)phenyl](2,2,2-trifluoroethyl)amino]butanoic acid

Synthesized as described in example 2 using 1,1-dimethylethyl 2-[[4-cyano-3-(trifluoromethyl)phenyl](2,2,2-trifluoroethyl)amino]butanoate: $^1$H NMR (400 MHz, CDCl$_3$) δ 7.68 (d, J=8.8 Hz, 1H), 7.17 (d, J=2.8 Hz, 1H), 7.02 (dd, J=8.8, 2.8 Hz, 1H), 4.22 (dd, J=8.8, 6.3 Hz, 1H), 4.05 (m, 2H), 2.20 (m, 1H), 1.98 (m, 1H), 1.56 (t, J=7.3 Hz, 3H).

Example 31

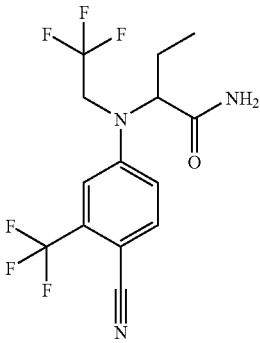

2-[[4-Cyano-3-(trifluoromethyl)phenyl](2,2,2-trifluoroethyl)amino]butanamide

Synthesized as described in example 3 using 2-[[4-cyano-3-(trifluoromethyl)phenyl](2,2,2-trifluoroethyl)amino]butanoic acid and ammonia: $^1$H NMR (400 MHz, CDCl$_3$) δ 7.60 (d, J=9.0 Hz, 1H), 7.17 (d, J=2.6 Hz, 1H), 7.03 (dd, J=9.0, 2.8 Hz, 1H), 6.38 (bs, 1H), 6.27 (bs, 1H), 4.25-4.04 (m, 3H), 2.15 (m, 1H), 1.91 (m, 1H), 0.99 (t, J=7.4 Hz, 3H).

Example 32

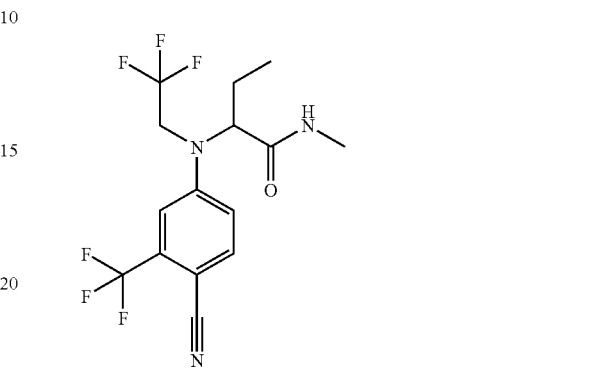

2-[[4-Cyano-3-(trifluoromethyl)phenyl](2,2,2-trifluoroethyl)amino]-N-methylbutanamide Synthesized as described in example 3 using 2-[[4-cyano-3-(trifluoromethyl)phenyl](2,2,2-trifluoroethyl)amino]butanoic acid: $^1$H NMR (400 MHz, CDCl$_3$) δ 7.62 (d, J=8.8 Hz, 1H), 7.14 (d, J=2.4 Hz, 1H), 7.01 (dd, J=8.8, 2.6 Hz, 1H), 6.18 (bs, 1H), 4.20 (m, 1H), 4.06 (q, J=7.5 Hz, 2H), 2.80 (d, J=4.7 Hz, 3H), 2.20 (m, 1H), 1.88 (m, 1H), 0.99 (t, J=7.4 Hz, 3H).

Example 33

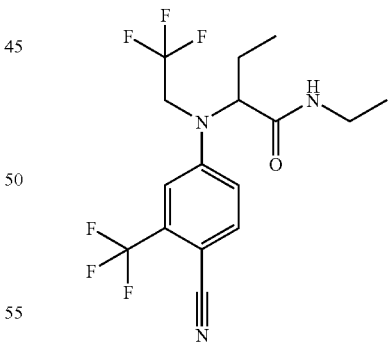

2-[[4-Cyano-3-(trifluoromethyl)phenyl](2,2,2-trifluoroethyl)amino]-N-ethylbutanamide Synthesized as described in example 3 using 2-[[4-cyano-3-(trifluoromethyl)phenyl](2,2,2-trifluoroethyl)amino]butanoic acid and ethylamine: $^1$H NMR (400 MHz, CDCl$_3$) δ 7.64 (d, J=8.8 Hz, 1H), 7.14 (d, J=2.6 Hz, 1H), 7.01 (dd, J=8.8, 2.8 Hz, 1H), 5.99 (bs, 1H), 4.22 (m, 1H), 4.09 (m, 1H), 4.00 (t, J=7.4 Hz, 1H), 3.28 (m, 2H), 2.21 (m, 1H), 1.90 (m, 1H), 1.07 (t, J=7.4 Hz, 3H), 0.99 (t, J=7.5 Hz, 3H).

Example 34

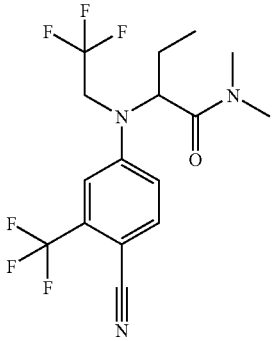

2-[[4-Cyano-3-(trifluoromethyl)phenyl](2,2,2-trifluoroethyl)amino]-N,N-dimethylbutanamide Synthesized as described in example 3 using 2-[[4-cyano-3-(trifluoromethyl)phenyl](2,2,2-trifluoroethyl)amino]butanoic acid and dimethylamine: $^1$H NMR (400 MHz, CDCl$_3$) δ 7.70 (d, J=8.8 Hz, 1H), 7.17 (d, J=2.6 Hz, 1H), 7.05 (dd, J=8.8, 2.8 Hz, 1H), 4.51 (dd, J=8.4, 5.5 Hz, 1H), 4.17 (m, 1H), 4.05 (m, 1H), 2.98 (s, 3H), 2.97 (s, 3H), 2.06 (m, 1H), 1.67 (m, 1H), 0.97 (t, J=7.4 Hz, 3H).

Example 35

1,1-Dimethylethyl N-[4-cyano-3-(trifluoromethyl)phenyl]-N-propylglycinate

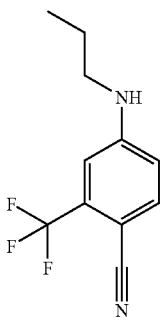

A. 4-(Propylamino)-2-(trifluoromethyl)benzonitrile

Synthesized as described in step A of example 1 using n-propylamine: $^1$H NMR (400 MHz, CDCl$_3$) δ 7.53 (d, J=8.6 Hz, 1H), 6.82 (d, J=2.4 Hz, 1H), 6.65 (dd, J=8.6, 2.4 Hz, 1H), 4.44 (bs, 1H), 3.15 (t, J=7.1 Hz, 2H), 1.67 (m, 2H), 1.01 (t, J=7.5 Hz, 3H).

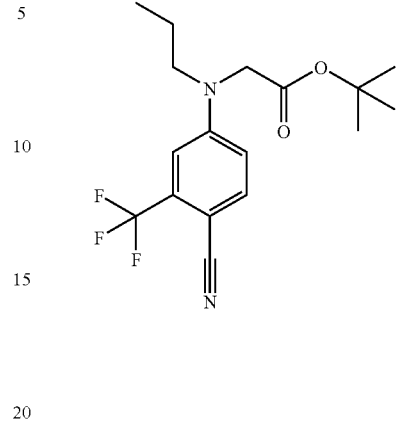

B. 1,1-Dimethylethyl N-[4-cyano-3-(trifluoromethyl)phenyl]-N-propylglycinate

Synthesized as described in step B of example 1 using 4-(propylamino)-2-(trifluoromethyl)benzonitrile: $^1$H NMR (400 MHz, CDCl$_3$) δ 7.57 (d, J=8.8 Hz, 1H), 6.82 (d, J=2.6 Hz, 1H), 6.70 (dd, J=9.0, 2.8 Hz, 1H), 3.98 (s, 2H), 3.93 (t, J=7.5 Hz, 2H), 1.67 (q, J=7.5 Hz, 2H), 1.44 (s, 9H), 0.97 (t, J=7.5 Hz, 3H).

Example 36

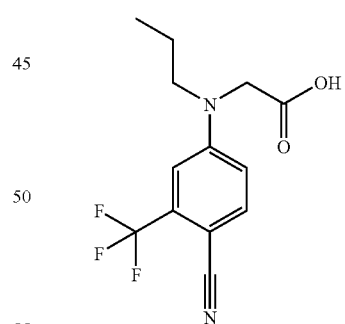

N-[4-Cyano-3-(trifluoromethyl)phenyl]-N-propylglycine

Synthesized as described in example 2 using 1,1-dimethylethyl N-[4-cyano-3-(trifluoromethyl)phenyl]-N-propylglycinate: $^1$H NMR (400 MHz, CDCl$_3$) δ 7.61 (d, J=8.7 Hz, 1H), 6.87 (d, J=2.6 Hz, 1H), 6.71 (dd, J=8.8, 2.6 Hz, 1H), 4.18 (s, 2H), 3.41 (t, J=7.7 Hz, 2H), 1.68 (m, 2H), 0.98 (t, J=7.5 Hz, 3H).

Example 37

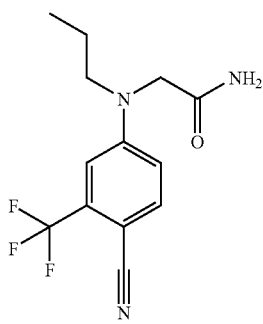

N²-[4-Cyano-3-(trifluoromethyl)phenyl]-N²-propylglycinamide

Synthesized as described in example 4 using N-[4-cyano-3-(trifluoromethyl)phenyl]-N-propylglycine: $^1$H NMR (400 MHz, DMSO-$d_6$) δ 7.75 (d, J=9.3 Hz, 1H), 7.49 (bs, 1H), 7.18 (bs, 1H), 6.87 (bs, 2H), 4.03 (s, 2H), 3.39 (t, J=7.6 Hz, 2H), 1.53 (q, J=7.4 Hz, 2H), 0.86 (t, J=7.3 Hz, 3H).

Example 38

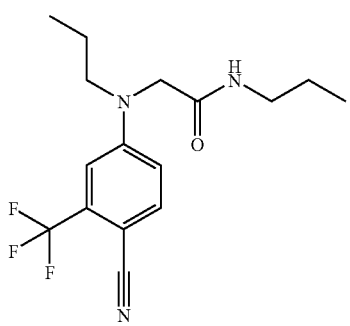

N²-[4-Cyano-3-(trifluoromethyl)phenyl]-N¹,N²-dipropylglycinamide

Synthesized as described in example 3 using N-[4-cyano-3-(trifluoromethyl)phenyl]-N-propylglycine and propylamine: $^1$H NMR (400 MHz, CDCl$_3$) δ 7.61 (d, J=8.6 Hz, 1H), 6.92 (d, J=2.5 Hz, 1H), 6.76 (dd, J=8.8, 2.5 Hz, 1H), 5.94 (bs, 1H), 3.98 (s, 2H), 3.41 (t, J=7.9 Hz, 2H), 3.22 (q, J=6.8 Hz, 2H), 1.68 (m, 2H), 1.45 (m, 2H), 0.99 (t, J=7.3 Hz, 3H), 0.82 (t, J=7.5 Hz, 3H).

Example 39

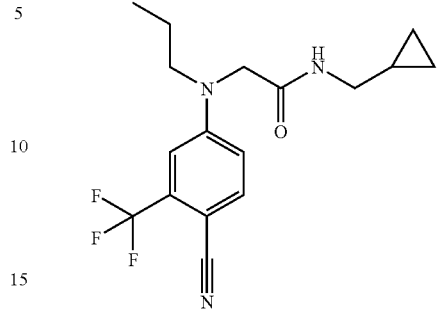

N²-[4-Cyano-3-(trifluoromethyl)phenyl]-N¹-(cyclopropyl methyl)-N²-propylglycinamide Synthesized as described in example 3 using N-[4-cyano-3-(trifluoromethyl)phenyl]-N-propylglycine and 1-cyclopropylmethane amine: $^1$H NMR (400 MHz, CDCl$_3$) δ 7.62 (d, J=8.8 Hz, 1H), 6.93 (d, J=2.6 Hz, 1H), 6.77 (dd, J=8.8, 2.8 Hz, 1H), 6.00 (bs, 1H), 3.99 (s, 2H), 3.43 (t, J=7.7 Hz, 2H), 3.12 (t, J=6.8 Hz, 2H), 1.70 (m, 2H), 0.99 (t, J=7.5 Hz, 3H), 0.87 (m, 1H), 0.44 (m, 2H), 0.13 (m, 2H).

Example 40

1,1-Dimethylethyl N-[4-cyano-3-(trifluoromethyl)phenyl]-N²-propen-1-ylglycinate

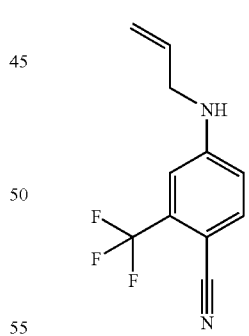

A. 4-(2-Propen-1-ylamino)-2-(trifluoromethyl)benzonitrile

Synthesized in a manner similar to step A of example 1 using allylamine: $^1$H NMR (300 MHz, CD$_3$OD) δ 7.58 (d, J=8.8 Hz, 1H), 6.95 (d, J=1.9 Hz, 1H), 6.79 (dd, J=8.6, 2.2 Hz, 1H), 5.89 (ddt, J=17.2, 10.3, 5.1 Hz, 1H), 5.24 (apparent dq, J=17.2, 1.7 Hz, 1H), 5.17 (apparent dq, J=10.4, 1.6 Hz, 1H), 3.84 (apparent d, J=5.1 Hz, 2H).

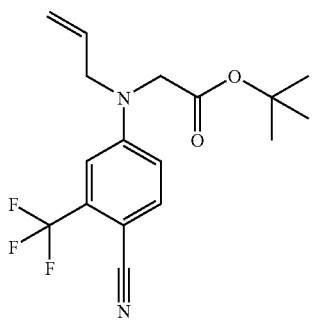

B. 1,1-Dimethylethyl N-[4-cyano-3-(trifluoromethyl) phenyl]-$N^2$-propen-1-ylglycinate Synthesized in a manner similar to step B of example 1: $^1$H NMR (300 MHz, CD$_3$OD) δ 7.68 (d, J=8.7 Hz, 1H), 6.96 (d, J=2.4 Hz, 1H), 6.92 (dd, J=8.7, 2.6 Hz, 1H), 5.90 (ddt, J=17.4, 10.7, 5.1 Hz, 1H), 5.18 (m, =CH$_2$, 2H), 4.18 (s, 2H), 4.09 (apparent d, J=4.8 Hz, 2H), 1.48 (s, 9H).

Secondary Aniline Synthesis Method C

Example 41

Methyl N-[4-cyano-3-(trifluoromethyl)phenyl]-N-(2-fluoroethyl)glycinate

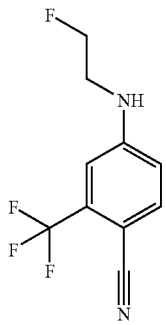

A. 4-[(2-Fluoroethyl)amino]-2-(trifluoromethyl)benzonitrile

To a solution of 4-amino-2-(trifluoromethyl)benzonitrile (0.100 g, 0.54 mmol) in acetonitrile (3 mL) was added cesium carbonate (0.438 g, 1.34 mmol) and 1-bromo-2-fluoroethane (0.340 g, 2.68 mmol). The mixture was heated in a microwave at 120° C. for 15 min. Upon cooling, additional 1-bromo-2-fluoroethane (0.340 g, 2.68 mmol) was added and the reaction was heated in the microwave at 140° C. for 20 min. Upon cooling, the solids were filtered off and washed with ethyl acetate. The filtrate was concentrated in vacuo and the residue was purified by radial chromatography (10-40% ethyl acetate-hexane gradient) to give 0.100 g of a mixture (6:1) of the title compound and 4-[bis(2-fluoroethyl)amino]-2-(trifluoromethyl)benzonitrile as a white solid, which was used as such in the next reaction.

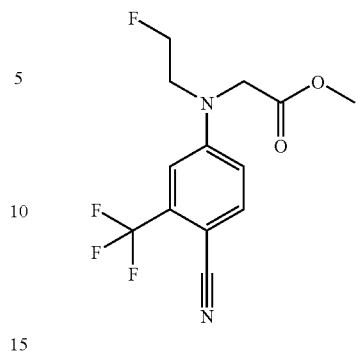

B. Methyl N-[4-cyano-3-(trifluoromethyl)phenyl]-N-(2-fluoroethyl)glycinate

To a solution of a 6:1 mixture of 4-[(2-fluoroethyl)amino]-2-(trifluoromethyl)benzonitrile and 4-[bis(2-fluoroethyl)amino]-2-(trifluoromethyl)benzonitrile (0.100 g) in acetonitrile (3 mL) was added Cs$_2$CO$_3$ (0.169 g, 0.52 mmol) and methyl bromoacetate (0.080 g, 0.52 mmol). The mixture was heated at 85° C. for 2 h. Upon cooling, additional methyl bromoacetate (0.080 g, 0.52 mmol) was added and heated at 85° C. for 8 h. Upon cooling, the mixture was partitioned between ethyl acetate and water. The organic phase was washed with brine, dried (Na$_2$SO$_4$), and concentrated in vacuo. The residue was purified by radial chromatography (10-80% EtOAc-hexanes gradient) to give 0.052 g (50% yield) of the desired product as a white solid: $^1$H NMR (400 MHz, CDCl$_3$) δ 7.62 (d, J=8.9 Hz, 1H), 6.92 (d, J=2.7 Hz, 1H), 6.76 (dd, J=8.9, 2.7 Hz, 1H), 4.68 (dt, J=47.0, 4.8 Hz, 2H), 4.21 (s, 2H), 3.81 (dt, J=25.6, 4.8 Hz, 2H), 3.78 (s, 3H).

Representative Procedure for Coupling Method C

Example 42

$N^2$-[4-Cyano-3-(trifluoromethyl)phenyl]-$N^2$-(2-fluoroethyl)glycinamide

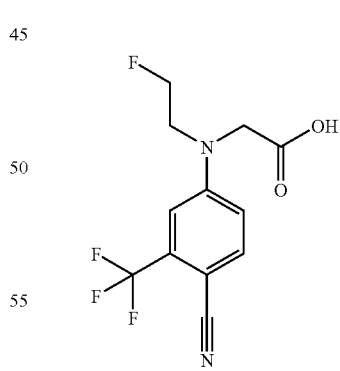

A. N-[4-Cyano-3-(trifluoromethyl)phenyl]-N-(2-fluoroethyl)glycine

Synthesized in a manner similar to example 24 using methyl N-[4-cyano-3-(trifluoromethyl)phenyl]-N-(2-fluoroethyl)glycinate to give the desired product as a white solid, which was used as such in the next reaction.

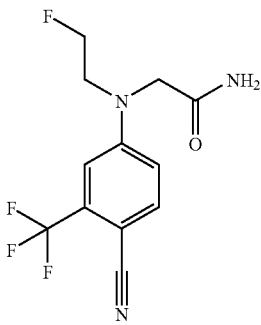

B. $N^2$-[4-Cyano-3-(trifluoromethyl)phenyl]-$N^2$-(2-fluoroethyl)glycinamide A suspension of N-[4-cyano-3-(trifluoromethyl)phenyl]-N-(2-fluoroethyl)glycine (0.031 g, 0.11 mmol) in anhydrous CH$_2$Cl$_2$ (2 mL), under nitrogen, was cooled in an ice bath and treated with oxalyl chloride (0.017 g, 0.13 mmol) and anhydrous DMF (~0.001 g). The mixture was heated at 50° C. for 20 min. Upon cooling, the mixture was added into an aqueous solution of ammonia (30%, 10 mL) and stirred heavily for 5 min. The mixture was partitioned between CH$_2$Cl$_2$ (20 mL), water (20 mL) and methanol (5 mL). The aqueous phase was extracted 3 times with CH$_2$Cl$_2$/MeOH (~10:1). The combined organic extracts were washed with brine, dried over sodium sulfate and concentrated in vacuo. The residue was crystallized from CH$_2$Cl$_2$/MeOH to give 0.012 g (40% yield) of the title compound as a white solid: $^1$H NMR (400 MHz, DMSO-d$_6$) δ 7.79 (d, J=8.8 Hz, 1H), 7.52 (bs, 1H), 7.21 (bs, 1H), 6.99 (d, J=2.4 Hz, 1H), 6.93 (dd, J=8.8, 2.4 Hz, 1H), 4.61 (dt, J=47.4, 4.9 Hz, 2H), 4.08 (s, 2H), 3.82 (dt, J=26.0, 4.9 Hz, 2H).

Example 43

1,1-Dimethylethyl N-[4-cyano-3-(trifluoromethyl)phenyl]-N-(2-methylpropyl)glycinate

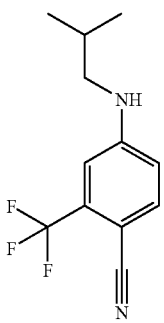

A. 4-(Isobutylamino)-2-(trifluoromethyl)benzonitrile

Synthesized as described in step A of example 1 using isobutylamine: $^1$H NMR (400 MHz, CDCl$_3$) δ 7.53 (d, J=8.6 Hz, 1H), 6.82 (d, J=2.4 Hz, 1H), 6.65 (dd, J=8.6, 2.4 Hz, 1H), 4.45 (bs, 1H), 3.00 (d, J=7.0 Hz, 2H), 1.90 (m, 1H), 1.00 (d, J=6.8 Hz, 6H).

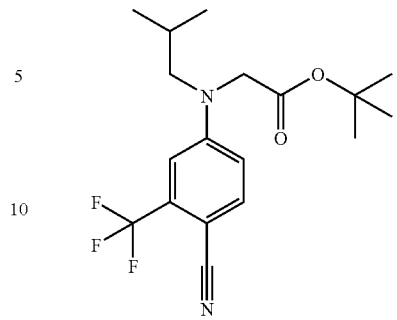

B. 1,1-Dimethylethyl N-[4-cyano-3-(trifluoromethyl)phenyl]-N-(2-methylpropyl)glycinate Synthesized as described in step B of example 1 using 4-(isobutylamino)-2-(trifluoromethyl)benzonitrile: $^1$H NMR (400 MHz, CDCl$_3$) δ 7.57 (d, J=8.8 Hz, 1H), 6.83 (d, J=2.5 Hz, 1H), 6.71 (dd, J=8.8, 2.8 Hz, 1H), 4.00 (s, 2H), 3.24 (d, J=7.5 Hz, 2H), 2.02. (m, 1H), 1.44 (s, 9H), 0.96 (d, J=6.6 Hz, 6H).

Example 44

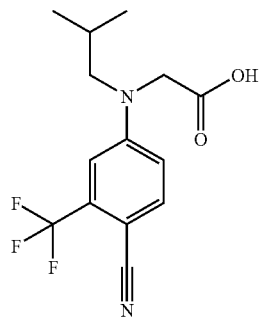

N-[4-Cyano-3-(trifluoromethyl)phenyl]-N-isobutylglycine

Synthesized as described in example 2 using 1,1-dimethylethyl N-[4-cyano-3-(trifluoromethyl)phenyl]-N-(2-methylpropyl)glycinate: $^1$H NMR (400 MHz, CDCl$_3$) δ 7.59 (d, J=9.0 Hz, 1H), 6.90 (d, J=2.6 Hz, 1H), 6.72 (dd, J=9.0, 2.7 Hz, 1H), 4.19 (s, 2H), 3.26 (d, J=7.5 Hz, 2H), 2.04 (m, 1H), 0.97 (d, J=6.6 Hz, 6H).

Example 45

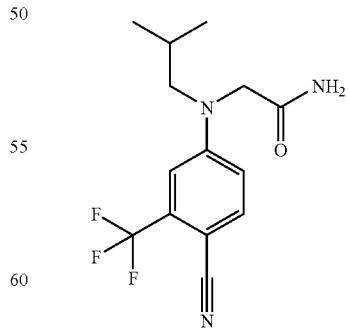

$N^2$-[4-Cyano-3-(trifluoromethyl)phenyl]-$N^2$-isobutylglycinamide

Synthesized as described in example 4 using N-[4-cyano-3-(trifluoromethyl)phenyl]-N-isobutylglycine: $^1$H NMR (400 MHz, DMSO-d$_6$) δ 7.74 (d, J=9.4 Hz, 1H), 7.48 (bs, 1H), 7.18 (bs, 1H), 6.89 (bs, 2H), 4.05 (s, 2H), 3.28 (d, J=7.3 Hz, 2H), 1.94 (m, 1H), 0.86 (d, J=6.6 Hz, 6H).

4.06 (s, 2H), 3.35 (d, J=6.8 Hz, 2H), 3.29 (m, 2H), 1.07 (t, J=7.1 Hz, 3H), 1.06 (m, 1H), 0.66 (m, 2H), 0.32 (m, 2H).

Example 46

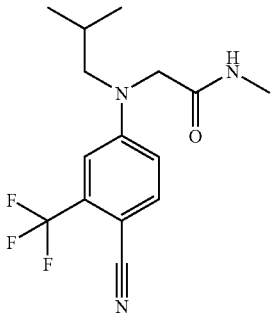

N²-[4-Cyano-3-(trifluoromethyl)phenyl]-N²-isobutyl-N¹-methylglycinamide

Synthesized as described in example 3 using N-[4-cyano-3-(trifluoromethyl)phenyl]-N-isobutylglycine: ¹H NMR (400 MHz, CDCl₃) δ 7.59 (d, J=8.8 Hz, 1H), 6.93 (d, J=2.7 Hz, 1H), 6.74 (dd, J=8.8, 2.8 Hz, 1H), 5.86 (d, J=4.0 Hz, 1H), 4.05 (s, 2H), 3.30 (d, J=7.4 Hz, 2H), 2.80 (d, J=4.9 Hz, 3H), 2.09 (m, 1H), 0.97 (d, J=6.8 Hz, 6H).

Example 47

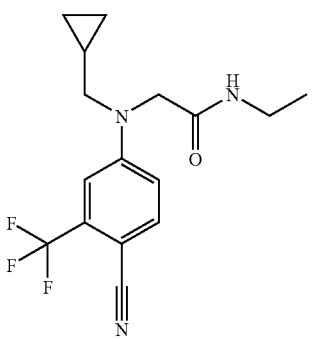

N²-[4-Cyano-3-(trifluoromethyl)phenyl]-N²-(cyclopropyl methyl)-N¹-ethylglycinamide Synthesized as described in example 3 using ethylamine: ¹H NMR (400 MHz, CDCl₃) δ 7.57 (d, J=8.8 Hz, 1H), 7.00 (d, J=2.5 Hz, 1H), 6.80 (dd, J=8.8, 2.6 Hz, 1H), 6.20 (bs, 1H),

Example 48

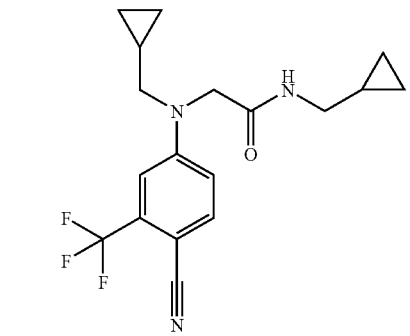

N²-[4-Cyano-3-(trifluoromethyl)phenyl]-N¹,N²-bis(cyclopropyl methyl)glycinamide

Synthesized in manner similar to example 3 using 1-cyclopropylmethyl amine: ¹H NMR (400 MHz, CDCl₃) δ 7.63 (d, J=8.8 Hz, 1H), 7.02 (d, J=2.5 Hz, 1H), 6.83 (dd, J=8.8, 2.7 Hz, 1H), 6.18 (bs, 1H), 4.08 (s, 2H), 3.37 (d, J=6.8 Hz, 2H), 3.12 (t, J=6.7 Hz, 2H), 1.09 (m, 1H), 0.86 (m, 1H), 0.67 (m, 2H), 0.45 (m, 2H), 0.34 (m, 2H), 0.13 (m, 2H).

Example 49

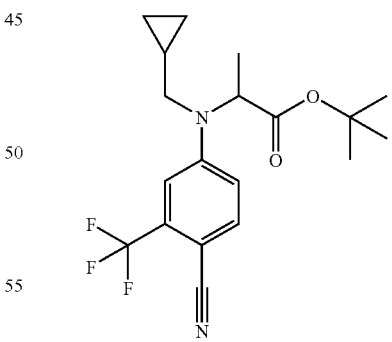

1,1-Dimethylethyl N-[4-cyano-3-(trifluoromethyl)phenyl]-N-(cyclopropylmethyl)alaninate Synthesized in manner similar to example 1 using 4-[(cyclopropylmethyl)amino]-2-(trifluoromethyl)benzonitrile and 1,1-dimethylethyl 2-bromopropanoate: ¹H NMR (400 MHz, CDCl₃) δ 7.58 (d, J=8.8 Hz, 1H), 7.04 (d, J=2.6 Hz, 1H), 6.86 (dd, J=8.9, 2.7 Hz, 1H), 4.33 (q, J=7.1 Hz, 1H), 3.30 (m, 2H), 1.54 (d, J=7.1 Hz, 3H), 1.39 (s, 9H), 0.99 (m, 1H), 0.63 (m, 2H), 0.29 (m, 2H).

5.8 Hz, 1H), 3.28 (dd, J=15.8, 9.4 Hz, 1H), 1.38 (d, J=7.0 Hz, 3H), 0.96 (m, 1H), 0.49 (m, 2H), 0.35 (m, 1H), 0.25 (m, 1H).

Example 50

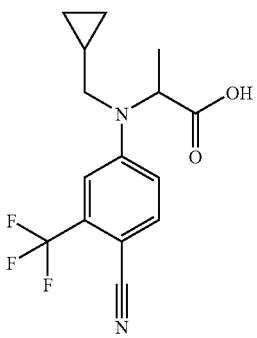

N-[4-Cyano-3-(trifluoromethyl)phenyl]-N-(cyclopropylmethyl)alanine

Synthesized as described in example 2 using 1,1-dimethylethyl N-[4-cyano-3-(trifluoromethyl)phenyl]-N-(cyclopropylmethyl)alaninate: $^1$H NMR (400 MHz, CDCl$_3$) δ 7.61 (d, J=8.9 Hz, 1H), 7.09 (d, J=2.6 Hz, 1H), 6.88 (dd, J=8.8, 2.6 Hz, 1H), 4.56 (q, J=7.1 Hz, 1H), 3.30 (d, J=5.8 Hz, 2H), 1.62 (d, J=7.1 Hz, 3H), 1.00 (m, 1H), 0.65 (m, 2H), 0.29 (m, 2H).

Example 51

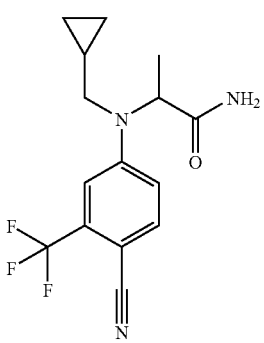

N$^2$-[4-Cyano-3-(trifluoromethyl)phenyl]-N$^2$-(cyclopropylmethyl)alaninamide

Synthesized as described in example 4 using N-[4-cyano-3-(trifluoromethyl)phenyl]-N-(cyclopropylmethyl)alanine: $^1$H NMR (400 MHz, DMSO-d$_6$) δ 7.79 (d, J=8.8 Hz, 1H), 7.40 (bs, 1H), 7.21 (bs, 1H), 7.06 (d, J=2.1 Hz, 1H), 7.00 (dd, J=8.8, 2.2 Hz, 1H), 4.47 (q, J=7.0 Hz, 1H), 3.42 (dd, J=15.5,

Example 52

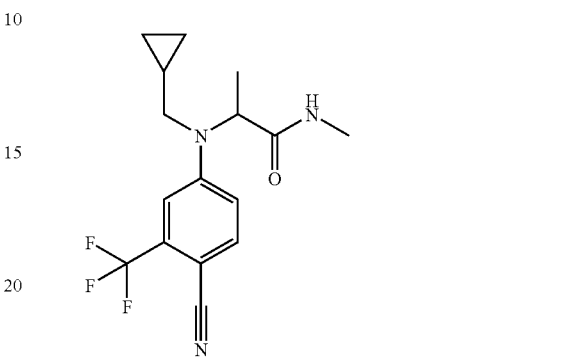

N$^2$-[4-Cyano-3-(trifluoromethyl)phenyl]-N$^2$-(cyclopropyl methyl)-N$^1$-methylalaninamide Synthesized as described in example 3 using N-[4-cyano-3-(trifluoromethyl)phenyl]-N-(cyclopropylmethyl)alanine: $^1$H NMR (400 MHz, CDCl$_3$) δ 7.52 (d, J=8.8 Hz, 1H), 7.05 (d, J=2.7 Hz, 1H), 6.83 (dd, J=8.7, 2.7 Hz, 1H), 6.43 (d, J=4.4 Hz, 1H), 4.33 (dd, J=14.1, 7.1 Hz, 1H), 3.38 (dd, J=15.5, 6.8 Hz, 1H), 3.23 (dd, J=15.4, 6.8 Hz, 1H), 2.79 (d, J=4.7 Hz, 3H), 1.53 (d, J=7.1 Hz, 3H), 1.04 (m, 1H), 0.68 (m, 2H), 0.33 (m, 2H).

Example 53

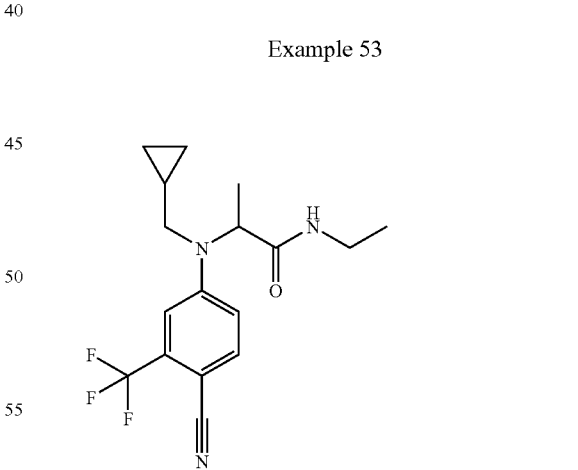

N$^2$-[4-Cyano-3-(trifluoromethyl)phenyl]-N$^2$-(cyclopropyl methyl)-N$^1$-ethylalaninamide Synthesized as described in example 3 using N-[4-cyano-3-(trifluoromethyl)phenyl]-N-(cyclopropylmethyl)alanine and ethylamine: $^1$H NMR (400 MHz, CDCl$_3$) δ 7.53 (d, J=8.8 Hz, 1H), 7.04 (d, J=2.4 Hz, 1H), 6.84 (dd, J=8.8, 2.7 Hz, 1H), 6.33 (bs, 1H), 4.27 (q, J=7.2 Hz, 1H), 3.40-3.20 (m, 4H), 1.51 (d, J=7.1 Hz, 3H), 1.05 (t, J=7.3 Hz, 3H), 1.04 (m, 1H), 0.68 (m, 2H), 0.34 (m, 2H).

Example 54

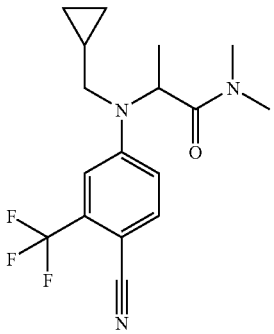

$N^2$-[4-Cyano-3-(trifluoromethyl)phenyl]-$N^2$-(cyclopropyl methyl)-$N^1$,$N^1$-dimethylalaninamide Synthesized as described in example 3 using N-[4-cyano-3-(trifluoromethyl)phenyl]-N-(cyclopropylmethyl)alanine and dimethylamine: $^1$H NMR (400 MHz, CDCl$_3$) δ 7.64 (d, J=8.8 Hz, 1H), 7.10 (d, J=2.5 Hz, 1H), 6.95 (dd, J=8.8, 2.6 Hz, 1H), 4.63 (q, J=6.6 Hz, 1H), 3.19 (m, 2H), 2.98 (s, 3H), 2.90 (s, 3H), 1.38 (d, J=6.8 Hz, 3H), 0.93 (m, 1H), 0.57 (m, 2H), 0.26 (m, 2H).

Example 55

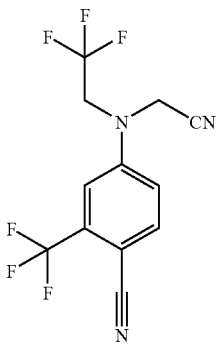

4-[(Cyanomethyl)(2,2,2-trifluoroethyl)amino]-2-(trifluoromethyl)benzonitrile

A mixture of $N^2$-[4-cyano-3-(trifluoromethyl)phenyl]-$N^2$-(2,2,2-trifluoroethyl)glycinamide (0.060 g, 0.18 mmol), CCl$_4$ (0.5 mL), DCE (4.5 mL) and polymer-supported triphenyl phosphine (3 mmol/g, 0.123 g, 0.36 mmol) was heated at 87° C. for 3 h. Upon cooling, the resin was filtered off, washed thoroughly with CHCl$_3$ and the filtrate concentrated in vacuo. The residue was purified by silica gel chromatography (5-40% EtOAc-hexane gradient) and the product was crystallized from CH$_2$Cl$_2$-hexanes to give the title compound as a white solid (0.030 g, 55% yield): $^1$HNMR (400 MHz, CDCl$_3$) δ 7.90 (d, J=8.6 Hz, 1H), 7.20 (d, J=2.6 Hz, 1H), 7.09 (dd, J=8.6, 2.6 Hz, 1H), 4.38 (s, 2H), 4.06 (q, J=8.2 Hz, 2H); MS (ES) m/z 308 (M+1).

Example 56

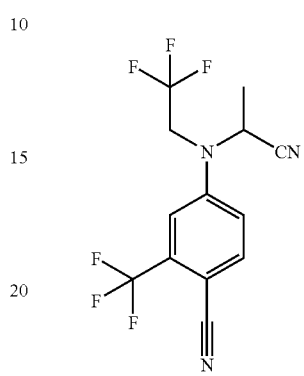

4-[(1-Cyanoethyl)(2,2,2-trifluoroethyl)amino]-2-(trifluoromethyl)benzonitrile

Synthesized as described in example 55 using $N^2$-[4-cyano-3-(trifluoromethyl)phenyl]-$N^2$-(2,2,2-trifluoroethyl)alaninamide: $^1$H NMR (400 MHz, CDCl$_3$) δ 7.80 (d, J=8.8 Hz, 1H), 7.32 (d, J=2.6 Hz, 1H), 7.24 (dd, J=8.8, 2.6 Hz, 1H), 4.72 (q, J=7.2 Hz, 1H), 4.04 (q, J=8.0 Hz, 2H), 1.75 (d, J=7.2 Hz, 3H); MS (ES) m/z 322 (M+1).

Example 57

Methyl 3-[[4-cyano-3-(trifluoromethyl)phenyl](2,2,2-trifluoroethyl)amino]-2-methylpropanoate

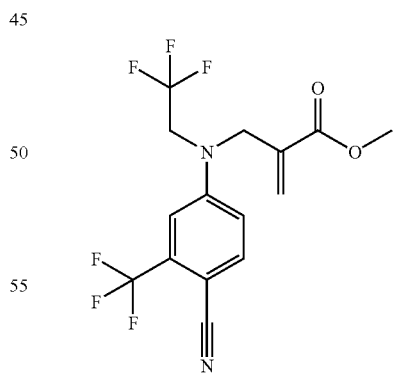

A. Methyl 2-{[[4-cyano-3-(trifluoromethyl)phenyl](2,2,2-trifluoroethyl)amino]methyl}acrylate Synthesized as described in example 2 from 4-[(2,2,2-trifluoroethyl)amino]-2-(trifluoromethyl)benzonitrile and methyl 2-(bromomethyl)acrylate: MS (ES) m/z 367 (M+1).

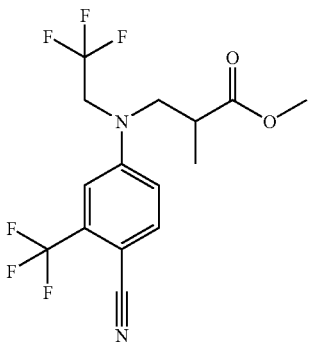

B. Methyl 3-[[4-cyano-3-(trifluoromethyl)phenyl](2,2,2-trifluoroethyl)amino]-2-methylpropanoate A suspension of 5% Pd/C (0.060 g) in EtOAc (3 mL) was stirred under an $H_2$ atmosphere (balloon pressure) for 15 min. A solution of methyl 2-{[[4-cyano-3-(trifluoromethyl)phenyl](2,2,2-trifluoroethyl)amino]methyl}acrylate (0.090 g, 0.245 mmol) in EtOAc (3 mL) was added and the mixture stirred for 1 hr. The catalyst was filtered off and washed with EtOAc. The filtrate was concentrated and purified by silica gel chromatography to afford 0.056 g (62% yield) of the title compound: MS (ES) m/z 369 (M+1).

Example 58

4-[(2-Cyanopropyl)(2,2,2-trifluoroethyl)amino]-2-(trifluoromethyl)benzonitrile

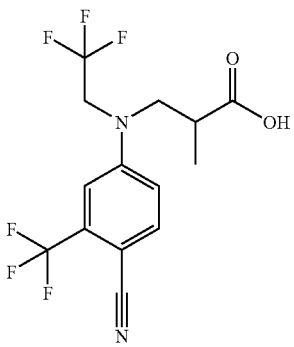

A. 3-[[4-Cyano-3-(trifluoromethyl)phenyl](2,2,2-trifluoroethyl)amino]-2-methylpropanoic acid A solution of methyl 3-[[4-cyano-3-(trifluoromethyl)phenyl](2,2,2-trifluoroethyl)amino]-2-methylpropanoate (0.056 g, 0.152 mmol) in 1:1 THF/MeOH (6 mL) was treated with NaOH (1N, 1 mL, 1.0 mmol) and heated at 75° C. for 30 min. Upon cooling, the mixture was partitioned between EtOAc and 0.1N HCl. The aqueous phase was extracted with EtOAc and the combined organic phases were washed with brine, dried ($Na_2SO_4$) and concentrated in vacuo to give the title compound (0.050 g, 94% yield): $^1H$ NMR (400 MHz, $CDCl_3$) δ 7.66 (d, J=8.8 Hz, 1H), 7.06 (d, J=2.6 Hz, 1H), 6.92 (dd, J=8.8, 2.6 Hz, 1H), 4.20-4.02 (m, 2H), 3.87 (dd, J=15.6, 9.0 Hz, 1H), 3.56 (dd, J=15.6, 5.0 Hz, 1H), 3.0-2.9 (m, 1H), 1.29 (d, J=7.1 Hz, 3H).

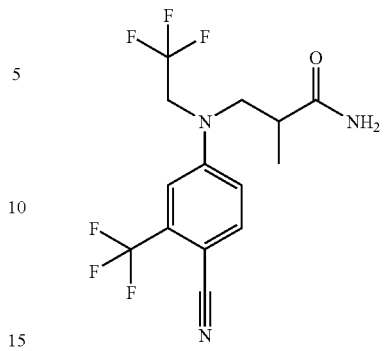

B. 3-[[4-Cyano-3-(trifluoromethyl)phenyl](2,2,2-trifluoroethyl)amino]-2-methylpropanamide To an ice-cold solution of 3-[[4-cyano-3-(trifluoromethyl)phenyl](2,2,2-trifluoroethyl)amino]-2-methylpropanoic acid (0.050 g, 0.14 mmol) in $CH_2Cl_2$ (3 mL), under nitrogen was added oxalyl chloride (0.023 g, 0.18 mmol) and DMF (cat) and the mixture was heated at 42° C. for 30 min. Upon cooling, additional oxalyl chloride (0.014 g, 0.11 mmol) and DMF (cat.) were added and heated for 30 min. Upon cooling, $NH_4OH$ (30% aqueous solution, 5 mL) was added and the mixture stirred at rt. After 1 h, the mixture was partitioned between $CH_2Cl_2$ and water. The organic phase was washed with 0.1N HCl and brine, dried ($Na_2SO_4$) and concentrated in vacuo. The residue was purified by silica gel chromatography (1-5% MeOH—$CH_2Cl_2$ gradient) to give the title compound (0.044 g, 88% yield): $^1H$ NMR (400 MHz, $CDCl_3$) δ 7.58 (d, J=8.6 Hz, 1H), 7.01 (d, J=2.6 Hz, 1H), 6.89 (dd, J=8.6, 2.6 Hz, 1H), 5.70 (bs, NH), 5.54 (bs, NH), 4.22-4.08 (m, 2H), 3.85 (dd, J=15.4, 10.3 Hz, 1H), 3.54 (dd, J=15.4, 3.7 Hz, 1H), 2.80-2.70 (m, 1H), 1.23 (d, J=7.0 Hz, 3H).

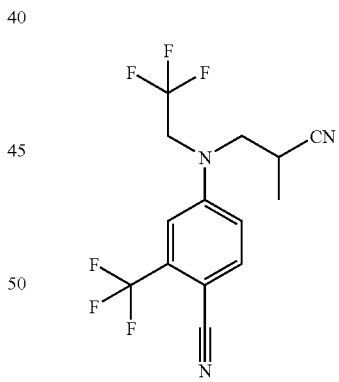

C. 4-[(2-Cyanopropyl)(2,2,2-trifluoroethyl)amino]-2-(trifluoromethyl)benzonitrile A mixture of 3-[[4-cyano-3-(trifluoromethyl)phenyl](2,2,2-trifluoroethyl)amino]-2-methylpropanamide (0.044 mg, 0.12 mmol), $CCl_4$ (1.5 mL), DCE (1.5 mL) and polymer-supported triphenyl phosphine (3 mmol/g, 0.089 g, 0.27 mmol) was heated at 87° C. for 2 h. Upon cooling, the resin was filtered off, washed thoroughly with $CHCl_3$ and the filtrate concentrated in vacuo. The residue was purified by silica gel chromatography (5-40% EtOAc-hexane gradient) and the product crystallized from CH$_2$Cl$_2$-hexanes to give the title compound as a white solid (0.021 g, 52% yield): $^1$H NMR (400 MHz, CDCl$_3$) δ 7.72 (d, J=8.8 Hz, 1H), 7.03 (d, J=2.6 Hz, 1H), 6.94 (dd, J=8.8, 2.6 Hz, 1H), 4.31-4.10 (m, 2H), 3.79-3.68 (m, 2H), 3.10-3.01 (m, 1H), 1.41 (d, J=7.2 Hz, 3H); MS (ES) m/z 336 (M+1).

Example 59

N-[4-Cyano-3-(trifluoromethyl)phenyl]-N-(2,2-dimethylpropyl)glycine

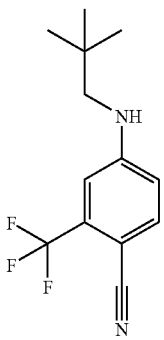

A. 4-[(2,2-Dimethylpropyl)amino]-2-(trifluoromethyl)benzonitrile

Synthesized as described in step A of example 1 using neopentylamine: $^1$H NMR (400 MHz, CDCl$_3$) δ 7.54 (d, J=8.6 Hz, 1H), 6.87 (d, J=2.2 Hz, 1H), 6.70 (dd, J=8.6, 2.3 Hz, 1H), 4.49 (bt, J=5.8 Hz, 1H), 2.98 (d, J=5.9 Hz, 2H), 1.01 (s, 9H).

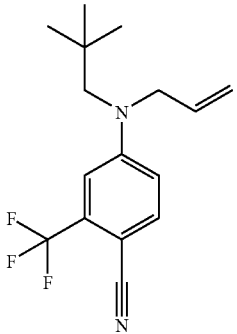

B. 4-[(2,2-Dimethylpropyl)(2-propen-1-yl)amino]-2-(trifluoromethyl)benzonitrile

To a slurry of hexanes-washed NaH (0.534 g of a 60% suspension in mineral oil, 13.4 mmol) in DMF (10 mL) at 0° C. was added a solution of 4-[(2,2-dimethylpropyl)amino]-2-(trifluoromethyl)benzonitrile (1.71 g, 6.68 mmol) in DMF (4 mL), dropwise over 10 min. The resulting solution was stirred 15 min and neat allyl bromide (1.16 mL, 13.4 mmol) was added dropwise over 3 min. The resulting solution was stirred 1 h, poured into water and the whole was extracted with Et$_2$O (×3). Combined organics were washed (water, brine), dried over Na$_2$SO$_4$, filtered and concentrated in vacuo. The residue was purified by flash chromatography (EtOAc/hexanes), affording 1.82 g of the title compound as a colorless syrup: $^1$H NMR (400 MHz, CDCl$_3$) δ 7.53 (d, J=8.9 Hz, 1H), 7.02 (d, J=2.7 Hz, 1H), 6.83 (dd, J=8.9, 2.5 Hz, 1H), 5.73 (ddt, J=17.2, 10.6, 4.6 Hz, 1H), 5.23 (app. d, J=10.6 Hz, 1H), 5.05 (app. d, J=17.5 Hz, 1H), 4.09 (overlapping ddd, 2H), 3.26 (s, 2H), 1.02 (s, 9H).

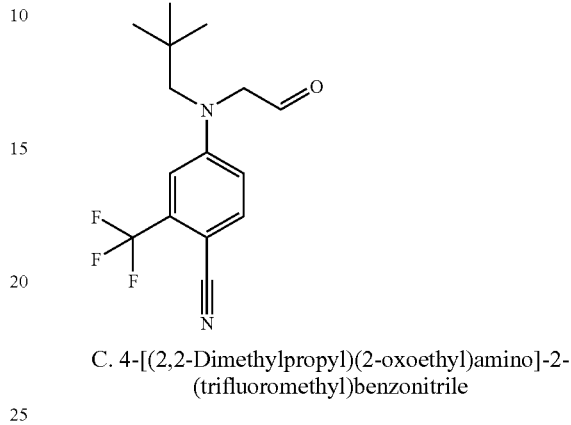

C. 4-[(2,2-Dimethylpropyl)(2-oxoethyl)amino]-2-(trifluoromethyl)benzonitrile

To a solution of 4-[(2,2-dimethylpropyl)(2-propen-1-yl)amino]-2-(trifluoromethyl)benzonitrile (1.46 g, 4.95 mmol) in THF/water (20:1, 45 mL) at rt was added a solution of OsO$_4$ (1.02 g of a 2.5 wt% solution in t-BuOH, 0.10 mmol) in THF/water (20:1, 5 mL), followed by NMO (1.22 g, 10.4 mmol) in one portion. The resulting mixture was stirred 22 hours at rt, cooled to 0° C. and sodium bisulfite (0.300 g) was added in one portion. The mixture was stirred 1 h, filtered through a pad of Celite (EtOAc wash) and the filtrate/washings were partitioned between EtOAc/water (required addition of NaCl to separated layers). The aqueous layer was extracted with EtOAc (×1), combined organics were washed with brine and concentrated in vacuo. The residue was dissolved in acetone (50 mL), a solution of NaIO$_4$ (2.22 g; 10.4 mmol) in water (20 mL) was added, the mixture was stirred two hours at rt and partially concentrated in vacuo to an aqueous residue. The residue was partitioned between EtOAc/water and the aqueous layer was further extracted with EtOAc (×1). Combined organics were washed (water, brine), dried over Na$_2$SO$_4$, filtered and concentrated in vacuo. The residue was purified by flash chromatography (EtOAc/hexanes), affording 1.20 g of the title compound as a colorless solid: $^1$H NMR (400 MHz, CDCl$_3$) δ 9.70 (s, 1H), 7.57 (d, J=8.8 Hz, 1H), 6.96 (d, J=2.5 Hz, 1H), 6.74 (dd, J=8.9, 2.7 Hz, 1H), 4.31 (s, 2H), 3.33 (s, 2H), 1.02 (s, 9H).

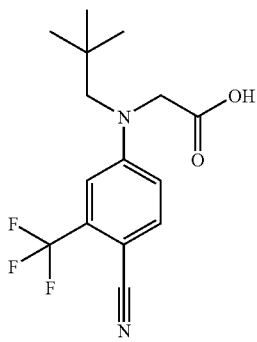

D. N-[4-Cyano-3-(trifluoromethyl)phenyl]-N-(2,2-dimethylpropyl)glycine

To a stirred slurry of 4-[(2,2-dimethylpropyl)(2-oxoethyl)amino]-2-(trifluoromethyl)benzonitrile (1.20 g, 4.03 mmol) and 2-methyl-2-butene (4.3 mL, 40 mmol) in t-BuOH (30 mL) at rt was added a solution of $NaClO_2$ (0.591 g of 80% tech. grade; 5.2 mmol) in $NaH_2PO_4$ buffer (6 mL, 1.5 M $NaH_2PO_4$, adjusted to pH 3.5 with 1 N HCl), dropwise over 5 min (slightly exothermic). After complete dissolution of slurried solids, the flask was stoppered with a rubber septum and placed under balloon pressure of nitrogen for 3 h. Water (100 mL) was added, the whole was adjusted to ca. pH 11 by addition of 15 wt % NaOH, and partially concentrated in vacuo. The aqueous residue was extracted with $Et_2O$ (×2), adjusted to ca. pH 1 by addition of 2 N HCl and extracted with EtOAc (×3). The combined EtOAc extracts were washed (brine), dried over $Na_2SO_4$, filtered and concentrated to dryness, affording 1.16 g of the title compound as a colorless foam: $^1H$ NMR (400 MHz, $CDCl_3$) δ 7.59 (d, J=8.9 Hz, 1H), 7.01 (d, J=2.2 Hz, 1H), 6.79 (dd, J=8.9, 2.5 Hz, 1H), 4.24 (s, 2H), 3.31 (s, 2H), 1.02 (s, 9H).

Example 60

$N^2$-[4-Cyano-3-(trifluoromethyl)phenyl]-$N^2$-(2,2-dimethylpropyl)glycinamide

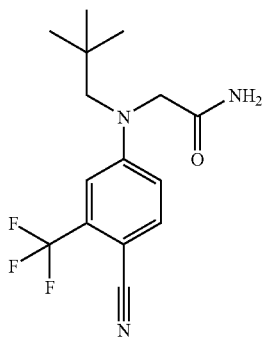

To a solution of N-[4-cyano-3-(trifluoromethyl)phenyl]-N-(2,2-dimethylpropyl)glycine (1.13 g, 3.58 mmol) in $CH_2Cl_2$ (10 mL) at 0° C. was added oxalyl chloride (0.33 mL, 3.76 mmol), followed by DMF (0.01 mL, 0.2 mmol). The resulting solution was stirred 5 min in the cooling bath, 20 min at rt and 1 h at reflux under $N_2$. After cooling to rt, the solution was slowly poured into $NH_4OH$ (10 mL of a 30 wt % solution) at 0° C., stirred 30 min, and the layers were separated. The aqueous layer was extracted with $CH_2Cl_2$ (×2), combined organics were washed (water, brine), dried over $Na_2SO_4$, filtered and concentrated in vacuo. The crude product was recrystallized from IPA/hexanes, affording 0.642 g of the title compound as a colorless, amorphous solid. The mother liquor was concentrated and purified by flash chromatography (EtOAc/hexanes), affording an additional 0.241 g of the title compound: $^1H$ NMR (400 MHz, $CDCl_3$) δ 7.61 (d, J=8.9 Hz, 1H), 7.07 (d, J=2.5 Hz, 1H), 6.85 (dd, J=8.9, 2.6 Hz, 1H), 5.70 (bs, 1H), 5.59 (bs, 1H), 4.12 (s, 2H), 3.38 (s, 2H), 1.03 (s, 9H).

Example 61

$N^2$-[4-Cyano-3-(trifluoromethyl)phenyl]-$N^2$-(2,2,2-trifluoro-1-methylethyl)glycinamide

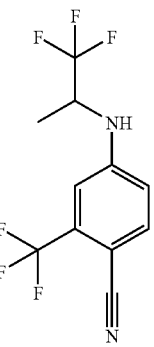

A. 2-(Trifluoromethyl)-4-[(2,2,2-trifluoro-1-methylethyl)amino]benzonitrile Synthesized as described in step A of example 12 using 1,1,1-trifluoroacetone: $^1H$ NMR (400 MHz, $CDCl_3$) δ 7.62 (d, J=8.6 Hz, 1H), 6.97 (d, J=2.2 Hz, 1H), 6.82 (dd, J=8.6, 2.2 Hz, 1H), 4.40 (bd, 8.8 Hz, 1H), 4.20-4.07 (m, 1H), 1.48 (d, J=6.7 Hz, 3H).

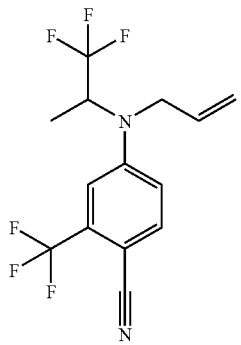

B. 4-[2-Propen-1-yl(2,2,2-trifluoro-1-methylethyl)amino]-2-(trifluoromethyl)benzonitrile Synthesized as described in step B of example 59 using 2-(trifluoromethyl)-4-[(2,2,2-trifluoro-1-methylethyl)amino]benzonitrile: $^1H$ NMR (400 MHz, $CDCl_3$) δ 7.63 (d, J=8.9 Hz, 1H), 7.10 (d, J=2.6 Hz, 1H), 6.96 (dd, J=9.0, 2.6 Hz, 1H), 5.79 (ddt, J=17.3, 10.6, 4.6 Hz, 1H), 5.28 (d, J=10.7 Hz, 1H), 5.18 (d, J=17.4 Hz, 1H), 4.55 (sept, J=7.0 Hz, 1H), 4.20-4.00 (m, 2H), 1.54 (J=6.9 Hz, 3H).

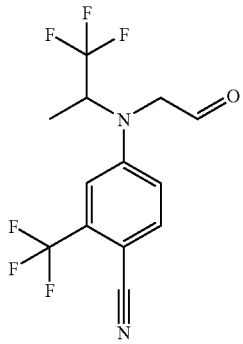

C. 4-[(2-Oxoethyl)(2,2,2-trifluoro-1-methylethyl)amino]-2-(trifluoromethyl)benzonitrile Synthesized as described in step C of example 59 using 4-[2-propen-1-yl(2,2,2-trifluoro-1-methylethyl)amino]-2-(trifluoromethyl)benzonitrile: $^1$H NMR (400 MHz, CDCl$_3$) δ 9.71 (s, 1H), 7.68 (d, J=8.8 Hz, 1H), 6.97 (d, J=2.2 Hz, 1H), 6.84 (dd, J=8.7, 2.5 Hz, 1H), 4.60 (sept, J=6.9 Hz, 1H), 4.34 (d, J=19.7 Hz, 1H), 4.26 (d, J=19.7 Hz, 1H), 1.50 (d, J=7.0 Hz, 3H).

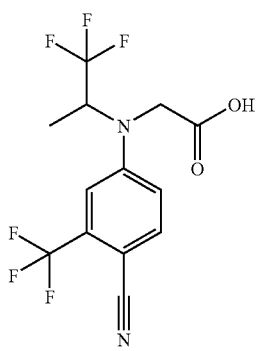

D. N-[4-Cyano-3-(trifluoromethyl)phenyl]-N-(2,2,2-trifluoro-1-methylethyl)glycine Synthesized as described in step D of example 59 using 4-[(2-oxoethyl)(2,2,2-trifluoro-1-methylethyl)amino]-2-(trifluoromethyl)benzonitrile: $^1$H NMR (400 MHz, CDCl$_3$) δ 7.69 (d, J=8.9 Hz, 1H), 7.04 (d, J=2.0 Hz, 1H), 6.91 (dd, J=8.9, 2.4 Hz, 1H), 4.58 (sept, J=6.9 Hz, 1H), 4.33 (d, J=19.2 Hz, 1H), 4.20 (d, J=19.2 Hz, 1H), 1.56 (d, J=6.9 Hz, 3H).

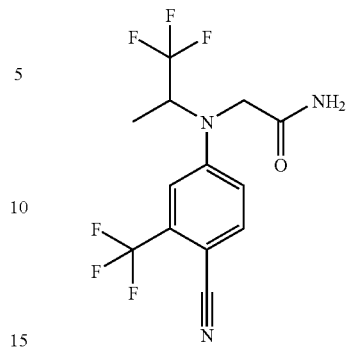

E. N$^2$-[4-Cyano-3-(trifluoromethyl)phenyl]-N$^2$-(2,2,2-trifluoro-1-methylethyl)glycinamide Synthesized as described in example 60 using N-[4-cyano-3-(trifluoromethyl)phenyl]-N-(2,2,2-trifluoro-1-methylethyl)glycine: $^1$H NMR (400 MHz, acetone-d$_6$) δ 7.83 (d, J=8.9 Hz, 1H), 7.33 (d, J=2.4 Hz, 1H), 7.24 (dd, J=9.0, 2.7 Hz, 1H), 7.17 (bs, 1H), 6.64 (bs, 1H), 5.20 (sept, J=7.1 Hz, 1H), 4.33 (d, J=18.3 Hz, 1H), 4.12 (d, J=18.3 Hz, 1H), 1.61 (d, J=6.9 Hz, 3H).

Example 62

N$^2$-[4-Cyano-3-(trifluoromethyl)phenyl]-N$^2$-[1-(trifluoromethyl)propyl]glycinamide

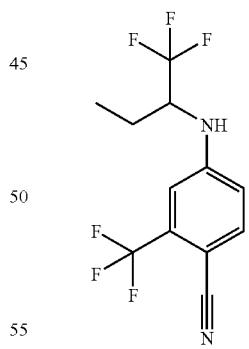

A. 2-(Trifluoromethyl)-4-{[1-(trifluoromethyl)propyl]amino}benzonitrile

Synthesized as described in step A of example 12 using 1,1,1-trifluorobutanone: $^1$H NMR (400 MHz, CDCl$_3$) δ 7.62 (d, J=8.6 Hz, 1H), 6.98 (d, J=2.3 Hz, 1H), 6.83 (dd, J=8.7, 2.3

Hz, 1H), 4.35 (bd, J=9.5 Hz, 1H), 3.94-3.82 (m, 1H), 2.09-1.97 (m, 1H), 1.72-1.58 (m, 1H), 1.08 (t, J=7.4 Hz, 3H).

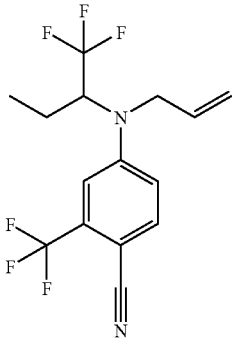

B. 4-{2-Propen-1-yl[1-(trifluoromethyl)propyl]amino}-2-(trifluoromethyl)benzonitrile Synthesized as described in step B of example 59 using 2-(trifluoromethyl)-4-{[1-(trifluoromethyl)propyl]amino}benzonitrile: $^1$H NMR (400 MHz, CDCl$_3$) δ 7.64 (d, J=8.9 Hz, 1H), 7.13 (d, J=2.6 Hz, 1H), 6.98 (dd, J=8.9, 2.7 Hz, 1H), 5.78-5.66 (m, 1H), 5.32-5.21 (m, 2H), 4.31-4.20 (m, 1H), 4.10-4.04 (m, 2H), 2.07-1.87 (m, 2H), 0.98 (t, J=7.4 Hz, 3H).

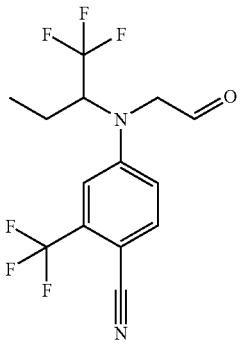

C. 4-{(2-Oxoethyl)[1-(trifluoromethyl)propyl]amino}-2-(trifluoromethyl)benzonitrile Synthesized as described in step C of example 59 using 4-{2-propen-1-yl[1-(trifluoromethyl)propyl]amino}-2-(trifluoromethyl)benzonitrile: $^1$H NMR (400 MHz, CDCl$_3$) δ 9.62 (s, 1H), 7.69 (d, J=8.8 Hz, 1H), 7.03 (d, J=2.4 Hz, 1H), 6.90 (dd, J=8.8, 2.6 Hz, 1H), 4.40-4.29 (m, 1H), 4.25 (d, J=19.5 Hz, 1H), 4.18 (d, J=19.4 Hz, 1H), 2.11-1.99 (m, 1H), 1.89-1.76 (m, 1H), 1.02 (t, J=7.4 Hz, 3H).

D. N-[4-Cyano-3-(trifluoromethyl)phenyl]-N-[1-(trifluoromethyl)propyl]glycine Synthesized as described in step D of example 59 using 4-{(2-oxoethyl)[1-(trifluoromethyl)propyl]amino}-2-(trifluoromethyl)benzonitrile: $^1$H NMR (400 MHz, CDCl$_3$) δ 7.69 (d, J=8.9 Hz, 1H), 7.07 (d, J=2.5 Hz, 1H), 6.95 (dd, J=8.8, 2.7 Hz, 1H), 4.36-4.26 (m, 1H, partially overlapping 4.27), 4.27 (d, J=18.9 Hz, 1H), 4.18 (d, J=19.0 Hz, 1H), 2.10-1.97 (m, 1H), 1.93-1.79 (m, 1H), 1.04 (t, J=7.4 Hz, 3H).

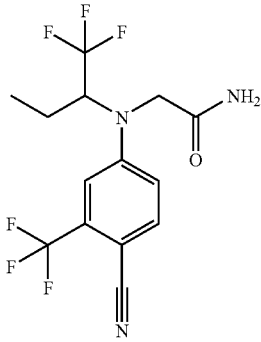

E. N$^2$-[4-Cyano-3-(trifluoromethyl)phenyl]-N$^2$-[1-(trifluoromethyl)propyl]glycinamide Synthesized as described in example 60 using N-[4-cyano-3-(trifluoromethyl)phenyl]-N-[1-(trifluoromethyl)propyl]glycine: $^1$H NMR (400 MHz, acetone-d$_6$) δ 7.83 (d, J=8.9 Hz, 1H), 7.40 (s, 1H), 7.32 (d, J=9.0 Hz, 1H), 7.04 (bs, 1H), 6.63 (bs, 1H), 5.04-4.92 (m, 1H), 4.32 (d, J=18.0 Hz, 1H), 4.23 (d, J=18.0 Hz, 1H), 2.12-1.93 (m, 2H, partially overlapping solvent), 1.08 (t, J=7.3 Hz, 3H).

Example 63

1,1-Dimethylethyl N-[4-cyano-3-(trifluoromethyl)phenyl]-N-(3,3,3-trifluoropropyl)glycinate

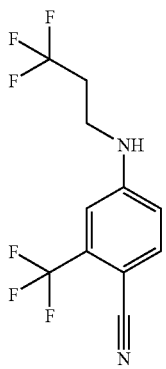

A. 2-(Trifluoromethyl)-4-[(3,3,3-trifluoropropyl)amino]benzonitrile

A mixture of 4-fluoro-2-(trifluoromethyl)benzonitrile (0.158 g, 0.84 mmol), (3,3,3-trifluoropropyl)amine hydrochloride (0.125 g, 0.84 mmol) and DIEA (0.326 g, 2.52 mmol) in 1.5 mL of DMSO was heated in a microwave at 200° C. for 20 min. Upon cooling, the mixture was partitioned between Et$_2$O and 0.1N HCl.

The organic phase was washed with 0.1N HCl (×2) and brine, dried over Na$_2$SO$_4$ and concentrated. The residue was purified by silica gel chromatography (10-80% EtOAc-hexanes gradient) and the product crystallized from Et$_2$O-hexanes to give 0.144 g (61% yield) of the title compound: $^1$H NMR (400 MHz, CDCl$_3$) δ 7.60 (d, J=8.6 Hz, 1H), 6.87 (d, J=2.4 Hz, 1H), 6.71 (dd, J=8.6, 2.4 Hz, 1H), 4.56 (bs, NH), 3.53 (q, J=6.5 Hz, 2H), 2.51-2.40 (m, 2H).

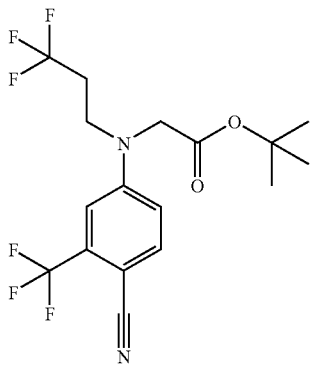

B. 1,1-Dimethylethyl N-[4-cyano-3-(trifluoromethyl)phenyl]-N-(3,3,3-trifluoropropyl)glycinate Synthesized as described in example 1B using 2-(trifluoromethyl)-4-[(3,3,3-trifluoropropyl)amino]benzonitrile and tert-butyl bromoacetate: $^1$H NMR (400 MHz, CDCl$_3$) δ 7.64 (d, J=8.8 Hz, 1H), 6.84 (d, J=2.6 Hz, 1H), 6.73 (dd, J=8.8, 2.6 Hz, 1H), 4.03 (s, 2H), 3.74 (t, J=7.5 Hz, 2H), 2.57-2.45 (m, 2H), 1.45 (s, 9H).

Example 64

N$^2$-[4-Cyano-3-(trifluoromethyl)phenyl]-N$^2$-(3,3,3-trifluoropropyl)glycinamide

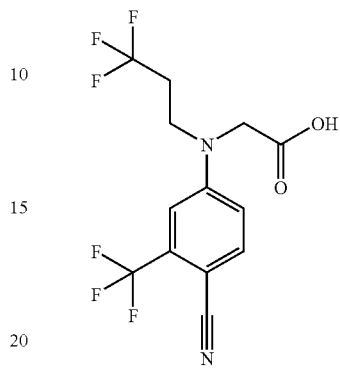

A. N-[4-Cyano-3-(trifluoromethyl)phenyl]-N-(3,3,3-trifluoropropyl)glycine

Synthesized as described in example 2 using 1,1-dimethylethyl N-[4-cyano-3-(trifluoromethyl)phenyl]-N-(3,3,3-trifluoropropyl)glycinate: $^1$H NMR (400 MHz, CD$_3$OD) δ 7.73 (d, J=8.8 Hz, 1H), 6.99 (d, J=2.2 Hz, 1H), 6.96 (dd, J=8.8, 2.2 Hz, 1H), 4.31 (s, 2H), 3.81 (t, J=7.4 Hz, 2H), 2.63-2.53 (m, 2H).

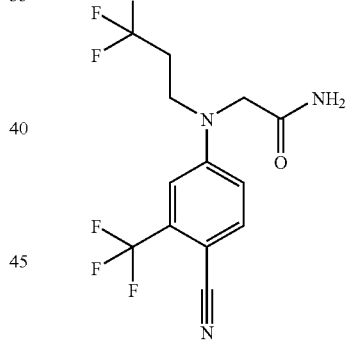

B. N$^2$-[4-Cyano-3-(trifluoromethyl)phenyl]-N$^2$-(3,3,3-trifluoropropyl)glycinamide To a suspension of N-[4-cyano-3-(trifluoromethyl)phenyl]-N-(3,3,3-trifluoropropyl)glycine (0.026 g, 0.076 mmol) in carbon tetrachloride/1,2-dichloroethane (1:3, 4 mL) was added polymer supported triphenylphosphine (0.051 g, 3 mmol/g, 0.153 mmol) and the mixture was heated at 75° C. After 3 h, additional phosphine resin (0.017 g, 0.051 mmol) was added and heating was continued at 90° C. for 30 min. Upon cooling, the resin was filtered off and washed with CHCl$_3$. The filtrate was concentrated and the residue was dissolved in THF (2 mL) and treated with NH$_4$OH (30% solution, 7 mL) for 15 min. The mixture was partitioned between EtOAc and water. The organic phase was washed with brine, dried over Na$_2$SO$_4$ and concentrated. The residue was purified by silica gel chromatography (0-12% MeOH—

CH$_2$Cl$_2$ gradient) and the product crystallized from CH$_2$Cl$_2$-hexanes to give 0.010 g (40% yield) of the title compound as a white solid: MS (ES) m/z 340 (M+1).

Example 65

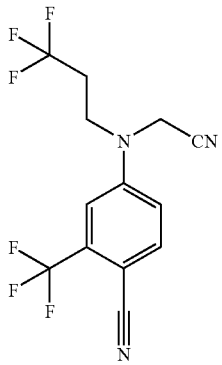

4-[(Cyanomethyl)(3,3,3-trifluoropropyl)amino]-2-(trifluoromethyl)benzonitrile

Synthesized from N$^2$-[4-cyano-3-(trifluoromethyl)phenyl]-N$^2$-(3,3,3-trifluoropropyl)glycinamide as described in example 55: MS (ES) m/z 322 (M+1).

Example 66

N$^2$-[4-Cyano-3-(trifluoromethyl)phenyl]-N$^2$-(3,3,3-trifluoropropyl)alaninamide

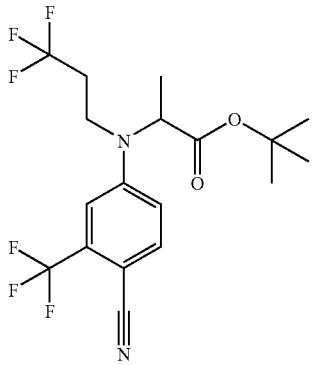

A. 1,1-Dimethylethyl N-[4-cyano-3-(trifluoromethyl)phenyl]-N-(3,3,3-trifluoropropyl)alaninate Synthesized as described in example 1B using 2-(trifluoromethyl)-4-[(3,3,3-trifluoropropyl)amino]benzonitrile and 1,1-dimethylethyl 2-bromopropanoate. $^1$H NMR (400 MHz, CDCl$_3$) δ 7.67 (d, J=8.8 Hz, 1H), 7.0 (d, J=2.6 Hz, 1H), 6.85 (dd, J=8.8, 2.6 Hz, 1H), 4.37 (q, J=7.3 Hz, 1H), 3.74 (t, J=8.1 Hz, 2H), 2.62-2.38 (m, 2H), 1.61 (d, J=7.3 Hz, 3H), 1.45 (s, 9H).

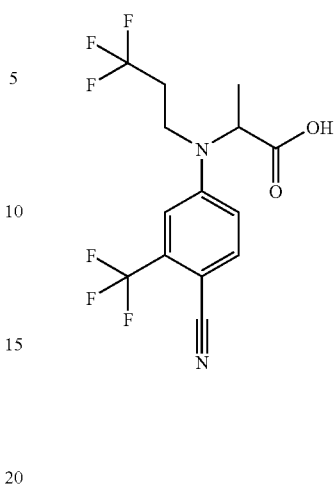

B. N-[4-Cyano-3-(trifluoromethyl)phenyl]-N-(3,3,3-trifluoropropyl)alanine

Synthesized as described in example 2 using 1,1-dimethylethyl N-[4-cyano-3-(trifluoromethyl)phenyl]-N-(3,3,3-trifluoropropyl)alaninate. $^1$H NMR (400 MHz, CDCl$_3$) δ 7.74 (d, J=8.8 Hz, 1H), 7.09 (d, J=2.4 Hz, 1H), 7.03 (dd, J=8.8, 2.4 Hz, 1H), 4.71 (q, J=7.1 Hz, 1H), 3.75 (t, J=8.0 Hz, 2H), 2.70-2.50 (m, 2H), 1.59 (d, J=7.1 Hz, 3H).

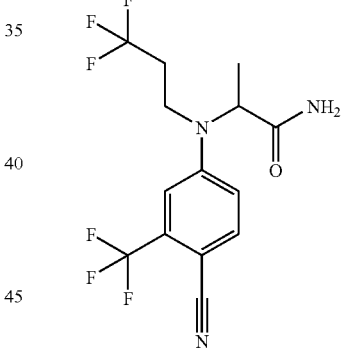

C. N$^2$-[4-Cyano-3-(trifluoromethyl)phenyl]-N$^2$-(3,3,3-trifluoropropyl)alaninamide To a suspension of N-[4-cyano-3-(trifluoromethyl)phenyl]-N-(3,3,3-trifluoropropyl)alanine (0.020 g, 0.56 mmol) in CH$_2$Cl$_2$ (2 mL) was added oxalyl chloride (0.009 g, 0.07 mmol) and a catalytic amount of DMF. The mixture was heated at 45° C. for 45 min, cooled to rt and added to NH$_4$OH (30% solution, 3 mL). The mixture was stirred for 30 min and then partitioned between EtOAc and 0.1N HCl. The organic phase was washed with brine, dried over Na$_2$SO$_4$ and concentrated. The residue was purified by silica gel chromatography (1-8% MeOH—CH$_2$Cl$_2$ gradient) and the product was crystallized from CH$_2$Cl$_2$-hexanes to give 0.014 g (70% yield) of the title compound as a white solid: MS (ES) m/z 354 (M+1).

Example 67

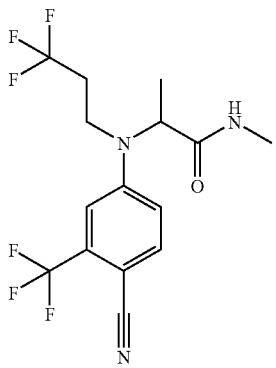

N$^2$-[4-Cyano-3-(trifluoromethyl)phenyl]-N$^1$-methyl-N$^2$-(3,3,3-trifluoropropyl)alaninamide Synthesized as described in example 3 using N -[4-cyano-3-(trifluoromethyl)phenyl]-N-(3,3,3-trifluoropropyl)alanine: MS (ES) m/z 368 (M+1).

Example 68

N$^2$-[4-Cyano-3-(trifluoromethyl)phenyl]-N$^2$-(1,1-dimethylethyl)glycinamide

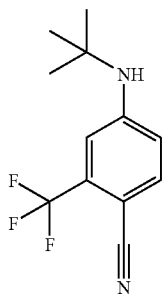

A. 4-[(1,1-Dimethylethyl)amino]-2-(trifluoromethyl)benzonitrile

Synthesized as described in step A of example 1 using t-butylamine: $^1$H NMR (400 MHz, CDCl$_3$) δ 7.52 (d, J=8.6 Hz, 1H), 6.90 (d, J=2.2 Hz, 1H), 6.77 (dd, J=8.7, 2.3 Hz, 1H), 4.49 (bs, 1H), 1.43 (s, 9H).

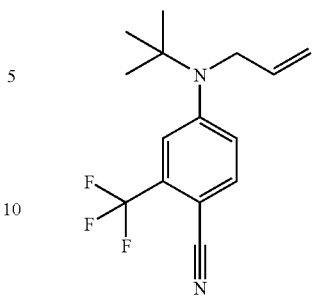

B. 4-[(1,1-Dimethylethyl)(2-propen-1-yl)amino]-2-(trifluoromethyl)benzonitrile

Synthesized as described in step B of example 59 using 4-[(1,1-dimethylethyl)amino]-2-(trifluoromethyl)benzonitrile: $^1$H NMR (400 MHz, CDCl$_3$) δ 7.55 (d, J=8.8 Hz, 1H), 7.28 (d, J=2.4 Hz, 1H), 7.11 (dd, J=8.8, 2.6 Hz, 1H), 5.87 (ddt, J=17.1, 10.5, 4.3 Hz, 1H), 5.24-5.13 (m, 2H), 4.00 (overlapping ddd, 2H), 1.46 (s, 9H).

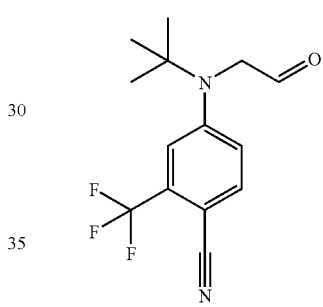

C. 4-[(1,1-Dimethylethyl)(2-oxoethyl)amino]-2-(trifluoromethyl)benzonitrile

Synthesized as described in step C of example 59 using 4-[(1,1-dimethylethyl)(2-propen-1-yl)amino]-2-(trifluoromethyl)benzonitrile: $^1$H NMR (400 MHz, CDCl$_3$) δ 9.72 (s, 1H), 7.65 (d, J=8.5 Hz, 1H), 7.31 (d, J=2.3 Hz, 1H), 7.14 (dd, J=8.6 Hz, 1H), 4.11 (s, 2H), 1.36 (s, 9H).

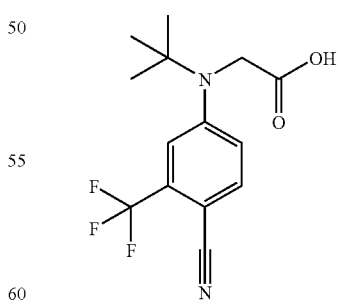

D. N-[4-Cyano-3-(trifluoromethyl)phenyl]-N-(1,1-dimethylethyl)glycine

Synthesized as described in step D of example 59 using 4-[(1,1-dimethylethyl)(2-oxoethyl)amino]-2-(trifluoromethyl)benzonitrile: ¹H NMR (400 MHz, CDCl₃) δ 7.66 (d, J=8.6 Hz, 1H), 7.36 (d, J=2.2 Hz, 1H), 7.18 (dd, J=8.7, 2.3 Hz, 1H), 4.13 (s, 2H), 1.42 (s, 9H).

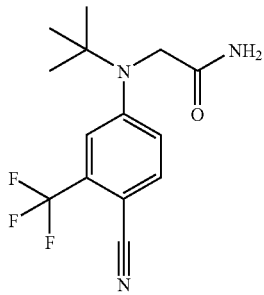

E. $N^2$-[4-Cyano-3-(trifluoromethyl)phenyl]-$N^2$-(1,1-dimethylethyl)glycinamide Synthesized as described in example 60 using N-[4-cyano-3-(trifluoromethyl)phenyl]-N-(1,1-dimethylethyl)glycine: ¹H NMR (400 MHz, CDCl₃) δ 7.72 (d, J=8.6 Hz, 1H), 7.45 (d, J=2.1 Hz, 1H), 7.33 (dd, J=8.5, 2.1 Hz, 1H), 6.51 (bs, 1H), 5.95 (bs, 1H), 3.90 (s, 2H), 1.33 (s, 9H).

Example 69

$N^2$-[4-Cyano-3-(trifluoromethyl)phenyl]-$N^2$-(1-methylethyl)glycinamide

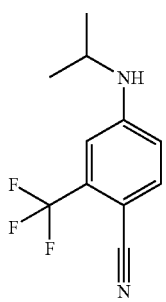

A. N 4-[(1-Methylethyl)amino]-2-(trifluoromethyl)benzonitrile

Synthesized as described in example 1A starting with 4-fluoro-2-(trifluoromethyl)benzonitrile and isopropyl amine: MS (ES) m/z 229 (M+1).

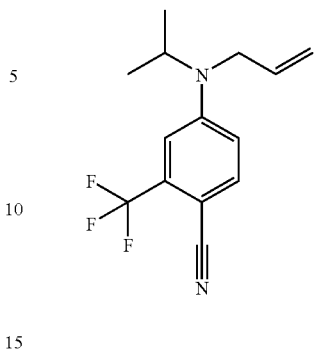

B. 4-[(1-Methylethyl)(2-propen-1-yl)amino]-2-(trifluoromethyl)benzonitrile

Synthesized as described in example 59B starting with N 4-[(1-methylethyl)amino]-2-(trifluoromethyl)benzonitrile: MS (ES) m/z 269 (M+1).

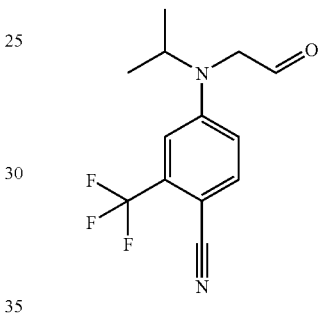

C. 4-[(1-Methylethyl)(2-oxoethyl)amino]-2-(trifluoromethyl)benzonitrile

Synthesized as described in example 59C starting 4-[(1-methylethyl)(2-propen-1-yl)amino]-2-(trifluoromethyl)benzonitrile: ¹H NMR (400 MHz, CDCl₃) δ 9.69 (s, 1H), 7.56 (d, J=8.8 Hz, 1H), 6.88 (d, J=2.6 Hz, 1H), 6.69 (dd, J=9.0, 2.8 Hz, 1H), 4.27 (sept, J=6.6 Hz, 1H), 4.09 (s, 2H), 1.22 (d, J=6.6 Hz, 6H).

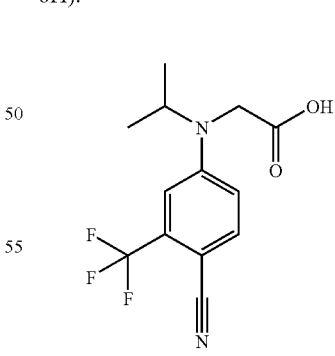

D. N-[4-Cyano-3-(trifluoromethyl)phenyl]-N-(1-methylethyl)glycine

Synthesized as described in example 59D starting with 4-[(1-methylethyl)(2-oxoethyl)amino]-2-(trifluoromethyl)benzonitrile: ¹H NMR (400 MHz, CDCl₃/CD₃OD) δ 7.54 (d, J=8.8 Hz, 1H), 6.90 (d, J=2.4 Hz, 1H), 6.72 (dd, J=8.8, 2.4 Hz, 1H), 4.18 (sept, J=6.6 Hz, 1H), 3.96 (s, 2H), 1.21 (d, J=6.6 Hz, 6H).

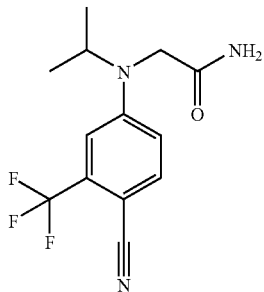

E. $N^2$-[4-Cyano-3-(trifluoromethyl)phenyl]-$N^2$-(1-methylethyl)glycinamide

Synthesized as described in example 4 using N-[4-cyano-3-(trifluoromethyl)phenyl]-N-(1-methylethyl)glycine: MS (ES) m/z 286 (M+1).

Example 70

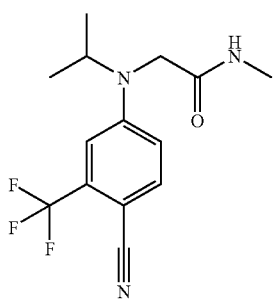

$N^2$-[4-Cyano-3-(trifluoromethyl)phenyl]-$N^1$-methyl-$N^2$-(1-methylethyl)glycinamide Synthesized as described in example 3 using N-[4-cyano-3-(trifluoromethyl)phenyl]-N-(1-methylethyl)glycine: MS (ES) m/z 300 (M+1).

Example 71

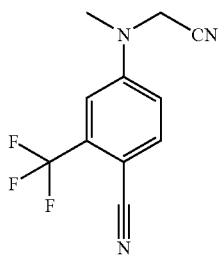

4-[(Cyanomethyl)(methyl)amino]-2-(trifluoromethyl)benzonitrile

Synthesized in a manner similar to example 1A using (methylamino)acetonitrile: MS (API) m/z 240 (M+1)

Example 72

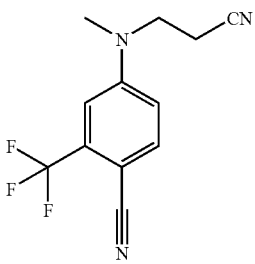

4-[(2-Cyanoethyl)(methyl)amino]-2-(trifluoromethyl)benzonitrile

Synthesized in a manner similar to example 1A using 3-(methylamino)propanenitrile: MS (API) m/z 254 (M+1).

Example 73

1,1-Dimethylethyl $N^2$-(3-chloro-4-cyanophenyl)-N-(2,2,2-trifluoroethyl)glycinate

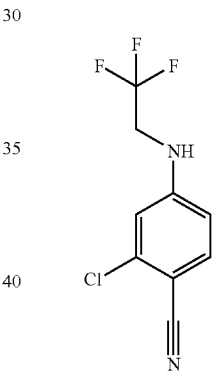

A. 2-Chloro-4-[(2,2,2-trifluoroethyl)amino]benzonitrile

Synthesized in a manner similar to example 12A using 4-amino-2-chlorobenzonitrile: MS (ES) m/z 235 (M+1).

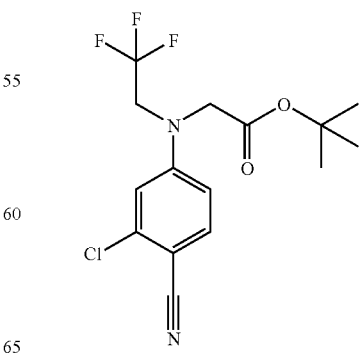

B. 1,1-Dimethylethyl $N^2$-(3-chloro-4-cyanophenyl)-N-(2,2,2-trifluoroethyl)glycinate Synthesized in a manner similar to example 1B using 2-chloro-4-[(2,2,2-trifluoroethyl)amino]benzonitrile: MS (ES) m/z 349 (M+1).

Example 74

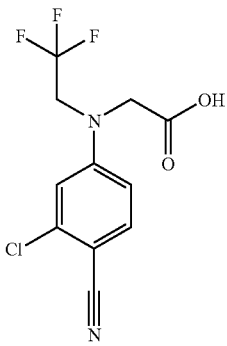

N-(3-Chloro-4-cyanophenyl)-N-(2,2,2-trifluoroethyl)glycine

Synthesized in a manner similar to example 2 using 1,1-dimethylethyl N-(3-chloro-4-cyanophenyl)-N-(2,2,2-trifluoroethyl)glycinate: MS (ES) m/z 293 (M+1).

Example 75

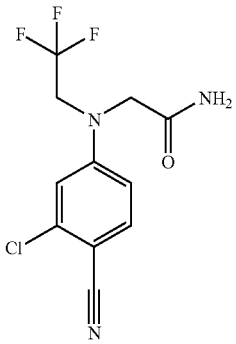

$N^2$-(3-Chloro-4-cyanophenyl)-$N^2$-(2,2,2-trifluoroethyl)glycinamide

Synthesized in a manner similar to example 4 using N-(3-chloro-4-cyanophenyl)-N-(2,2,2-trifluoroethyl)glycine: MS (ES) m/z 292 (M+1).

Example 76

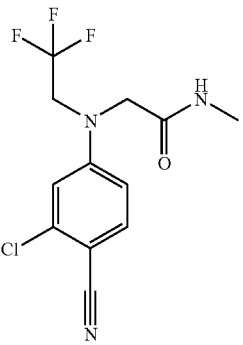

$N^2$-(3-Chloro-4-cyanophenyl)-$N^1$-methyl-$N^2$-(2,2,2-trifluoroethyl)glycinamide Synthesized in a manner similar to example 3 using N-(3-chloro-4-cyanophenyl)-N-(2,2,2-trifluoroethyl)glycine: MS (ES) m/z 306 (M+1).

Example 77

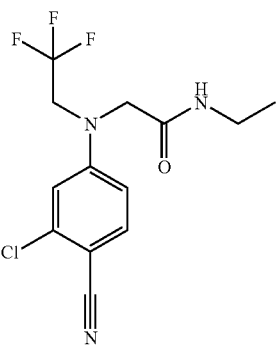

$N^2$-(3-Chloro-4-cyanophenyl)-$N^1$-ethyl-$N^2$-(2,2,2-trifluoroethyl)glycinamide Synthesized in a manner similar to example 3 using N-(3-chloro-4-cyanophenyl)-N-(2,2,2-trifluoroethyl)glycine and ethylamine: MS (ES) m/z 320 (M+1).

Example 78

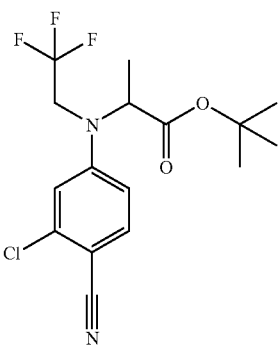

1,1-Dimethylethyl N-(3-chloro-4-cyanophenyl)-N-(2,2,2-trifluoroethyl)alaninate

Synthesized in a manner similar to example 1B using 2-chloro-4-[(2,2,2-trifluoroethyl)amino]benzonitrile and 1,1-dimethylethyl 2-bromopropanoate: MS (ES) m/z 363 (M+1).

Example 80

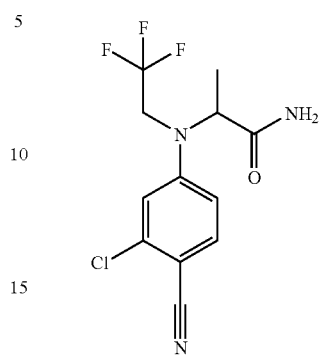

$N^2$-(3-Chloro-4-cyanophenyl)-$N^2$-(2,2,2-trifluoroethyl)alaninamide

Synthesized in a manner similar to example 4 using N-(3-chloro-4-cyanophenyl)-N-(2,2,2-trifluoroethyl)alanine: MS (ES) m/z 305 ($M^+$).

Example 79

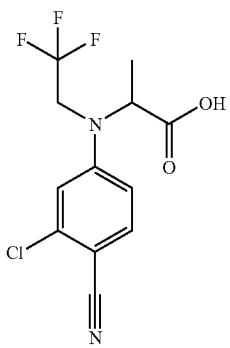

N-(3-Chloro-4-cyanophenyl)-N-(2,2,2-trifluoroethyl)alanine

Synthesized in a manner similar to example 2 using 1,1-dimethylethyl N-(3-chloro-4-cyanophenyl)-N-(2,2,2-trifluoroethyl)alaninate: MS (ES) m/z 307 (M+1)

Example 81

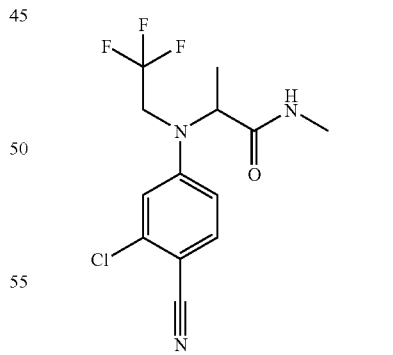

$N^2$-(3-Chloro-4-cyanophenyl)-$N^1$-methyl-$N^2$-(2,2,2-trifluoroethyl)alaninamide Synthesized in a manner similar to example 3 using N-(3-chloro-4-cyanophenyl)-N-(2,2,2-trifluoroethyl)alanine: MS (ES) m/z 320 (M+1).

Example 82

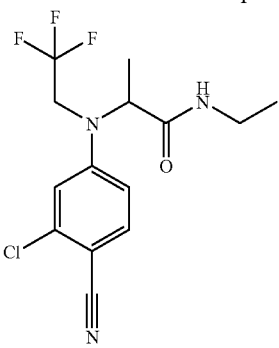

N²-(3-Chloro-4-cyanophenyl)-N¹-ethyl-N²-(2,2,2-trifluoroethyl)alaninamide

Synthesized in a manner similar to example 3 using N-(3-chloro-4-cyanophenyl)-N-(2,2,2-trifluoroethyl)alanine and ethylamine: MS (ES) m/z 334 (M+1).

Example 83

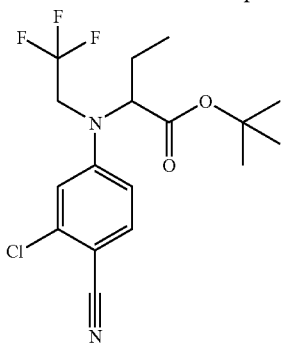

1,1-Dimethylethyl 2-[(3-chloro-4-cyanophenyl)(2,2,2-trifluoroethyl)amino]butanoate Synthesized in a manner similar to example 1B using 2-chloro-4-[(2,2,2-trifluoroethyl)amino]benzonitrile and tert-butyl 2-bromobutanoate: MS (ES) m/z 377 (M+1).

Example 84

2-[(3-Chloro-4-cyanophenyl)(2,2,2-trifluoroethyl)amino]butanamide

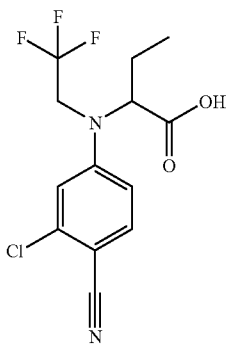

A. 2-[(3-Chloro-4-cyanophenyl)(2,2,2-trifluoroethyl)amino]butanoic acid

Synthesized in a manner similar to example 2 using 1,1-dimethylethyl 2-[(3-chloro-4-cyanophenyl)(2,2,2-trifluoroethyl)amino]butanoate: MS (ES) m/z 321 (M+1).

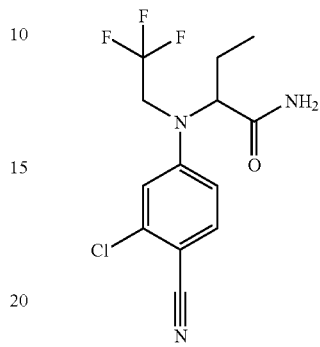

B. 2-[(3-Chloro-4-cyanophenyl)(2,2,2-trifluoroethyl)amino]butanamide

Synthesized in a manner similar to example 4 using 2-[(3-chloro-4-cyanophenyl)(2,2,2-trifluoroethyl)amino]butanoic acid: MS (ES) m/z 320 (M+1).

Example 85

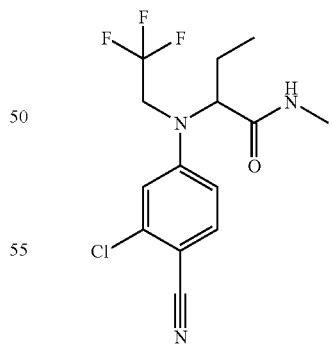

2-[(3-Chloro-4-cyanophenyl)(2,2,2-trifluoroethyl)amino]-N-methylbutanamide

Synthesized in a manner similar to example 3 using 2-[(3-chloro-4-cyanophenyl)(2,2,2-trifluoroethyl)amino]butanoic acid: MS (ES) m/z 334 (M+1).

Example 86

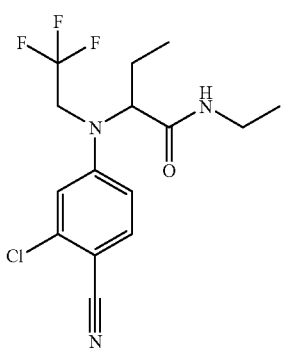

2-[(3-Chloro-4-cyanophenyl)(2,2,2-trifluoroethyl)amino]-N-ethylbutanamide

Synthesized in a manner similar to example 3 using 2-[(3-chloro-4-cyanophenyl)(2,2,2-trifluoroethyl)amino]butanoic acid and ethylamine: MS (ES) m/z 348 (M+1).

Example 87

1,1-Dimethylethyl N$^2$-(3-chloro-4-cyanophenyl)-N-(cyclopropyl methyl)glycinate

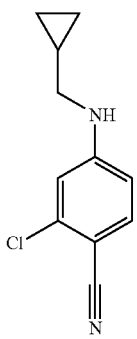

A. 2-Chloro-4-[(cyclopropylmethyl)amino]benzonitrile

Synthesized in a manner similar to example 1A using 2-chloro-4-fluorobenzonitrile: MS (ES) m/z 207 (M+1).

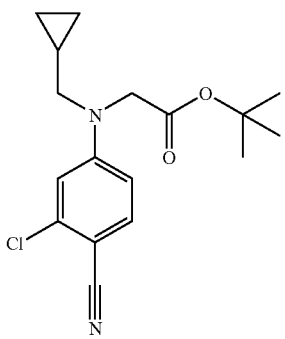

B. 1,1-Dimethylethyl N$^2$-(3-chloro-4-cyanophenyl)-N-(cyclopropyl methyl)glycinate Synthesized in a manner similar to example 1B using 2-chloro-4-[(cyclopropylmethyl)amino]benzonitrile: MS (ES) m/z 321 (M+1).

Example 88

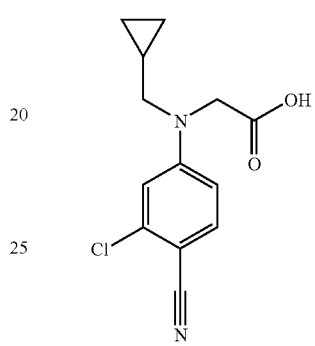

N-(3-Chloro-4-cyanophenyl)-N-(cyclopropylmethyl)glycine

Synthesized in a manner similar to example 2 using 1,1-dimethylethyl N-(3-chloro-4-cyanophenyl)-N-(cyclopropylmethyl)glycinate: MS (ES) m/z 265 (M+1).

Example 89

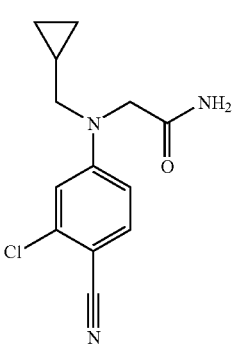

N$^2$-(3-Chloro-4-cyanophenyl)-N$^2$-(cyclopropylmethyl)glycinamide

Synthesized in a manner similar to example 4 using N-(3-chloro-4-cyanophenyl)-N-(cyclopropylmethyl)glycine: MS (ES) m/z 264 (M+1).

Example 90

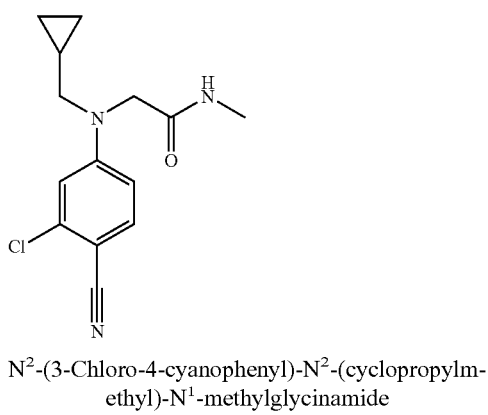

N²-(3-Chloro-4-cyanophenyl)-N²-(cyclopropylmethyl)-N¹-methylglycinamide

Synthesized in a manner similar to example 3 using N-(3-chloro-4-cyanophenyl)-N-(cyclopropylmethyl)glycine: MS (ES) m/z 278 (M+1).

Example 91

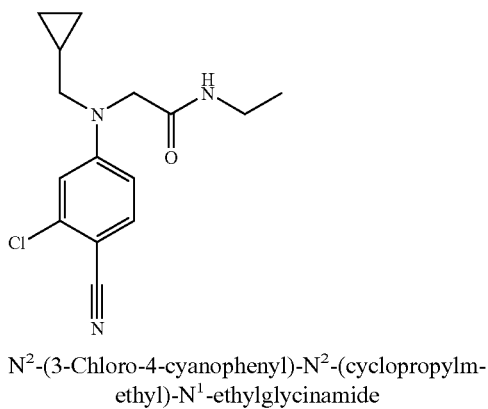

N²-(3-Chloro-4-cyanophenyl)-N²-(cyclopropylmethyl)-N¹-ethylglycinamide

Synthesized in a manner similar to example 3 using N-(3-chloro-4-cyanophenyl)-N-(cyclopropylmethyl)glycine and ethylamine: MS (ES) m/z 292 (M+1).

Example 92

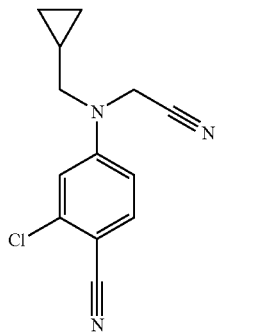

2-Chloro-4-[(cyanomethyl)(cyclopropylmethyl)amino]benzonitrile

Synthesized in a manner similar to example 55 using N²-(3-chloro-4-cyanophenyl)-N²-(cyclopropylmethyl)glycinamide: MS (ES) m/z 246 (M+1).

Example 93

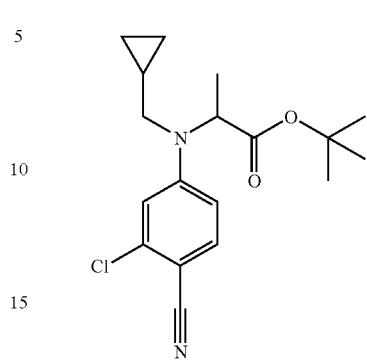

1,1-Dimethylethyl N-(3-chloro-4-cyanophenyl)-N-(cyclopropylmethyl)alaninate

Synthesized in a manner similar to example 1B using 2-chloro-4-[(cyclopropylmethyl)amino]benzonitrile and 1,1-dimethylethyl 2-bromopropanoate: MS (ES) m/z 335 (M+1).

Example 94

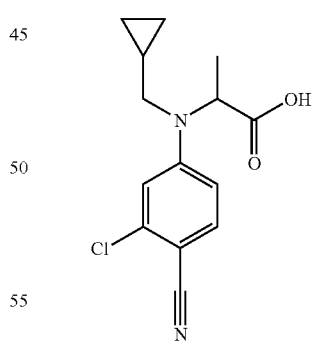

N-(3-Chloro-4-cyanophenyl)-N-(cyclopropylmethyl)alanine

Synthesized in a manner similar to example 2 using 1,1-dimethylethyl N-(3-chloro-4-cyanophenyl)-N-(cyclopropylmethyl)alaninate: MS (ES) m/z 279 (M+1).

Example 95

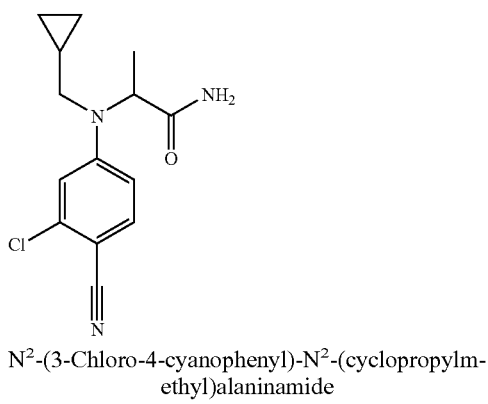

$N^2$-(3-Chloro-4-cyanophenyl)-$N^2$-(cyclopropylmethyl)alaninamide

Synthesized in a manner similar to example 4 using N-(3-chloro-4-cyanophenyl)-N-(cyclopropylmethyl)alanine: MS (ES) m/z 278 (M+1).

Example 96

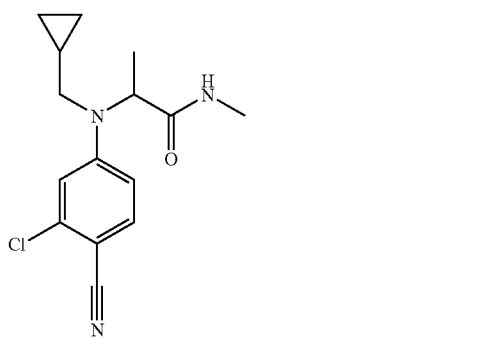

$N^2$-(3-Chloro-4-cyanophenyl)-$N^2$-(cyclopropylmethyl)-$N^1$-methylalaninamide Synthesized in a manner similar to example 3 using N-(3-chloro-4-cyanophenyl)-N-(cyclopropylmethyl)alanine: MS (ES) m/z 292 (M+1).

Example 97

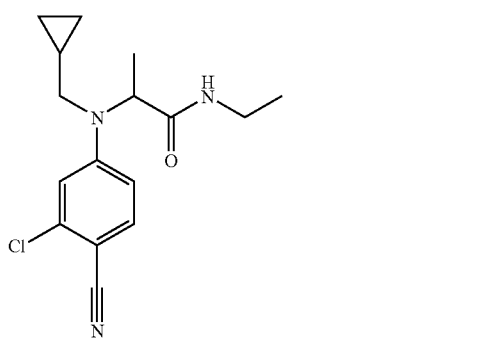

$N^2$-(3-Chloro-4-cyanophenyl)-$N^2$-(cyclopropylmethyl)-$N^1$-ethylalaninamide

Synthesized in a manner similar to example 3 using N-(3-chloro-4-cyanophenyl)-N-(cyclopropylmethyl)alanine and ethylamine: MS (ES) m/z 306 (M+1).

Example 98

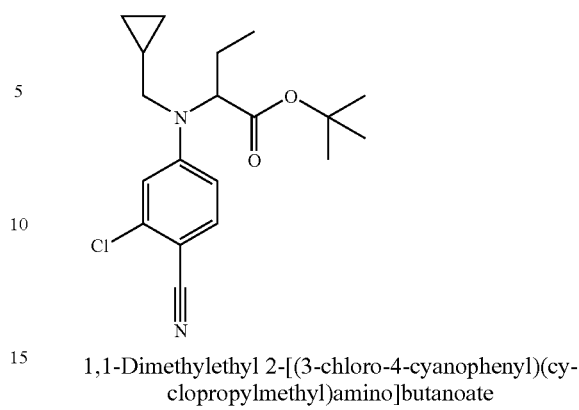

1,1-Dimethylethyl 2-[(3-chloro-4-cyanophenyl)(cyclopropylmethyl)amino]butanoate

Synthesized in a manner similar to example 1B using 2-chloro-4-[(cyclopropylmethyl)amino]benzonitrile and tert-butyl 2-bromobutanoate: MS (ES) m/z 349 (M+1).

Example 99

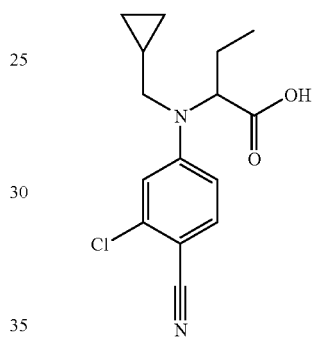

2-[(3-Chloro-4-cyanophenyl)(cyclopropylmethyl)amino]butanoic acid

Synthesized in a manner similar to example 2 using 1,1-dimethylethyl 2-[(3-chloro-4-cyanophenyl)(cyclopropylmethyl)amino]butanoate: MS (ES) m/z 293 (M+1).

Example 100

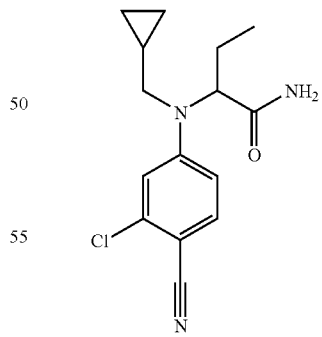

2-[(3-Chloro-4-cyanophenyl)(cyclopropylmethyl)amino]butanamide

Synthesized in a manner similar to example 4 using 2-[(3-chloro-4-cyanophenyl)(cyclopropylmethyl)amino]butanoic acid: MS (ES) m/z 292 (M+1).

Example 101

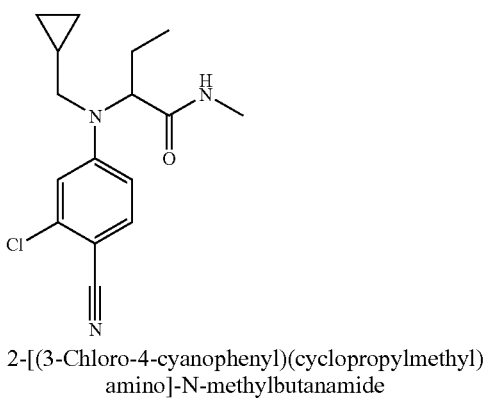

2-[(3-Chloro-4-cyanophenyl)(cyclopropylmethyl)amino]-N-methylbutanamide

Synthesized in a manner similar to example 3 using 2-[(3-chloro-4-cyanophenyl)(cyclopropylmethyl)amino]butanoic acid: MS (ES) m/z 306 (M+1).

Example 102

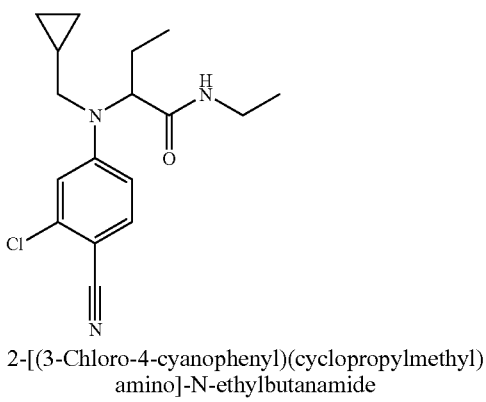

2-[(3-Chloro-4-cyanophenyl)(cyclopropylmethyl)amino]-N-ethylbutanamide

Synthesized in a manner similar to example 3 using 2-[(3-chloro-4-cyanophenyl)(cyclopropylmethyl)amino]butanoic acid and ethylamine: MS (ES) m/z 320 (M+1).

Example 103

Methyl N-(3,4-dicyanophenyl)-N-(2,2,2-trifluoroethyl)glycinate

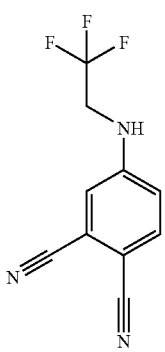

A. 4-[(2,2,2-Trifluoroethyl)amino]-1,2-benzenedicarbonitrile

Synthesized in a manner similar to example 12 using 4-amino-1,2-benzenedicarbonitrile:: $^1$H NMR (400 MHz, CDCl$_3$) δ 7.59 (d, J=8.6 Hz, 1H), 6.99 (d, J=2.6 Hz, 1H), 6.90 (dd, J=8.6, 2.6 Hz, 1H), 4.73 (broad t, NH), 3.86 (q, J=8.6 Hz, 2H).

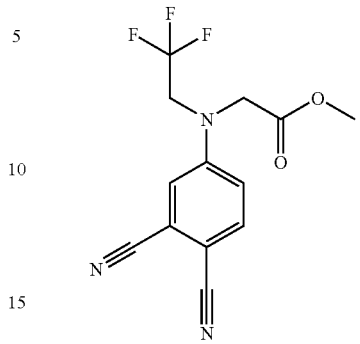

B. Methyl N-(3,4-dicyanophenyl)-N-(2,2,2-trifluoroethyl)glycinate

A solution of 4-[(2,2,2-trifluoroethyl)amino]-1,2-benzenedicarbonitrile (0.020 g, 0.089 mmol) in MeCN (3 mL) was treated with Cs$_2$CO$_3$ (0.078 g, 0.24 mmol) and methyl bromoacetate (0.037 g, 0.24 mmol) and heated at 85° C. under nitrogen for 8 h. Upon cooling, the mixture was partitioned between EtOAc and water. The organic phase was washed with brine, dried over Na$_2$SO$_4$ and concentrated. The residue was purified by silica gel chromatography (20-100% CH$_2$Cl$_2$-hexanes gradient) and the product crystallized from CH$_2$Cl$_2$-hexanes to give 0.015 g (58% yield) of the title compound as a white solid: MS (ES) m/z 296 (M−1).

Example 104

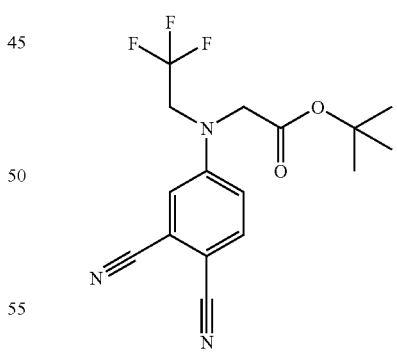

1,1-Dimethylethyl N-(3,4-dicyanophenyl)-N-(2,2,2-trifluoroethyl)glycinate

Synthesized in a manner similar to example 1B using 4-[(2,2,2-trifluoroethyl)amino]-1,2-benzenedicarbonitrile: MS (ES) m/z 340 (M+1).

Example 105
$N^2$-(3,4-Dicyanophenyl)-$N^2$-(2,2,2-trifluoroethyl) glycinamide

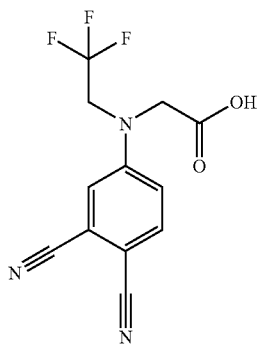

A. N-(3,4-Dicyanophenyl)-N-(2,2,2-trifluoroethyl) glycine

Synthesized in a manner similar to example 2 using 1,1-dimethylethyl N-(3,4-dicyanophenyl)-N-(2,2,2-trifluoroethyl)glycinate: MS (ESI) m/z 284 (M+1).

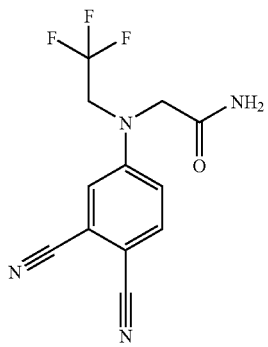

B. $N^2$-(3,4-Dicyanophenyl)-$N^2$-(2,2,2-trifluoroethyl) glycinamide

Synthesized in a manner similar to example 4 using N-(3,4-dicyanophenyl)-N-(2,2,2-trifluoroethyl)glycine: MS (ES) m/z 281 (M−1).

Example 106

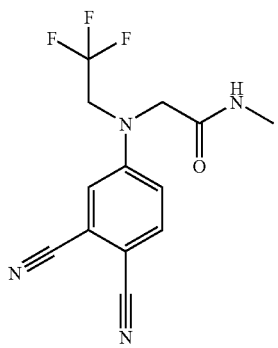

$N^2$-(3,4-Dicyanophenyl)-$N^1$-methyl-$N^2$-(2,2,2-trifluoroethyl)glycinamide

Synthesized in a manner similar to example 3 using N-(3,4-dicyanophenyl)-N-(2,2,2-trifluoroethyl)glycine: MS (ES) m/z 297 (M+1).

Example 107

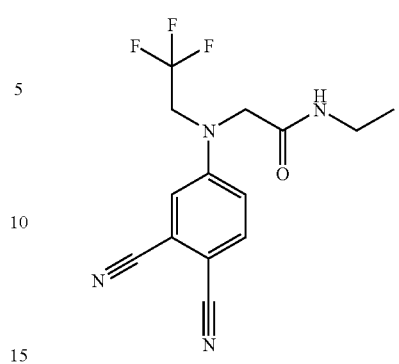

$N^2$-(3,4-Dicyanophenyl)-$N^1$-ethyl-$N^2$-(2,2,2-trifluoroethyl)glycinamide

Synthesized in a manner similar to example 3 using N-(3,4-dicyanophenyl)-N-(2,2,2-trifluoroethyl)glycine and ethylamine: MS (ES) m/z 311 (M+1).

Example 108

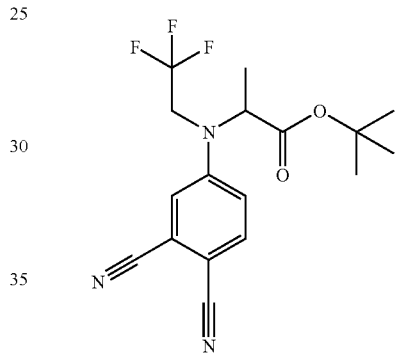

1,1-Dimethylethyl N-(3,4-dicyanophenyl)-N-(2,2,2-trifluoroethyl)alaninate

Synthesized in a manner similar to example 1B using 4-[(2,2,2-trifluoroethyl)amino]-1,2-benzenedicarbonitrile and 1,1-dimethylethyl 2-bromopropanoate: MS (ES) m/z 354 (M+1).

Example 109

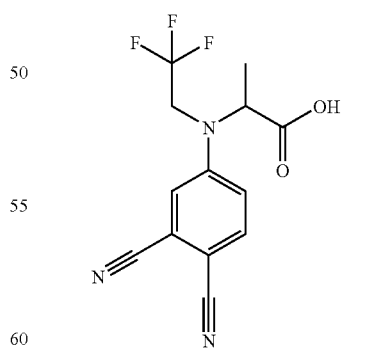

N-(3,4-Dicyanophenyl)-N-(2,2,2-trifluoroethyl)alanine

Synthesized in a manner similar to example 2 using 1,1-dimethylethyl N-(3,4-dicyanophenyl)-N-(2,2,2-trifluoroethyl)alaninate: MS (ES) m/z 298 (M+1).

Example 110

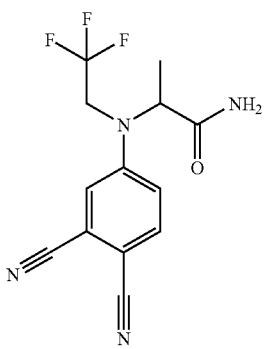

$N^2$-(3,4-Dicyanophenyl)-$N^2$-(2,2,2-trifluoroethyl) alaninamide

Synthesized in a manner similar to example 4 using N-(3,4-dicyanophenyl)-N-(2,2,2-trifluoroethyl)alanine: MS (ES) m/z 297 (M+1).

Example 111

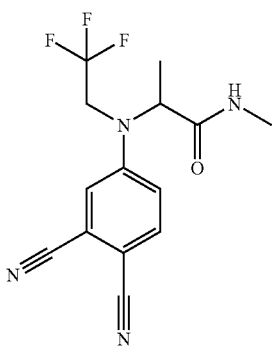

$N^2$-(3,4-Dicyanophenyl)-$N^1$-methyl-$N^2$-(2,2,2-trifluoroethyl)alaninamide

Synthesized in a manner similar to example 3 using N-(3,4-dicyanophenyl)-N-(2,2,2-trifluoroethyl)alanine: MS (ES) m/z 311 (M+1).

Example 112

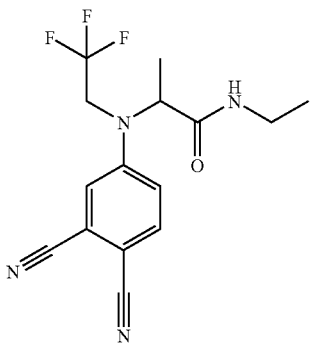

$N^2$-(3,4-Dicyanophenyl)-$N^1$-ethyl-$N^2$-(2,2,2-trifluoroethyl)alaninamide

Synthesized in a manner similar to example 3 using N-(3,4-dicyanophenyl)-N-(2,2,2-trifluoroethyl)glycine and ethylamine: MS (ES) m/z 323 (M−1).

Example 113

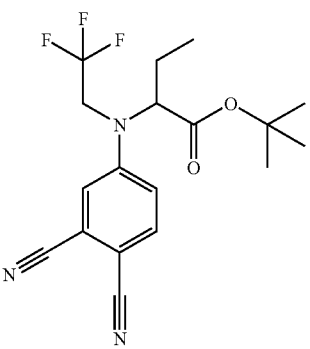

1,1-Dimethylethyl 2-[(3,4-dicyanophenyl)(2,2,2-trifluoroethyl)amino]butanoate

Synthesized in a manner similar to example 1B using 4-[(2,2,2-trifluoroethyl)amino]-1,2-benzenedicarbonitrile and tert-butyl 2-bromobutanoate: MS (ES) m/z 368 (M+1).

Example 114

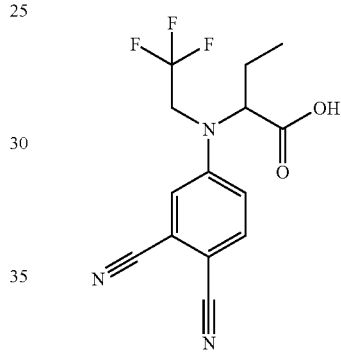

2-[(3,4-Dicyanophenyl)(2,2,2-trifluoroethyl)amino] butanoic acid

Synthesized in a manner similar to example 2 using 1,1-dimethylethyl 2-[(3,4-dicyanophenyl)(2,2,2-trifluoroethyl)amino]butanoate: MS (ES) m/z 312 (M+1).

Example 115

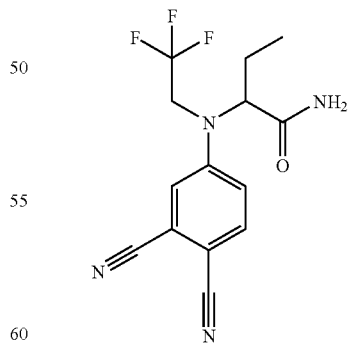

2-[(3,4-Dicyanophenyl)(2,2,2-trifluoroethyl)amino] butanamide

Synthesized in a manner similar to example 4 using 2-[(3,4-dicyanophenyl)(2,2,2-trifluoroethyl)amino]butanoic acid: MS (ES) m/z 311 (M+1).

Example 116

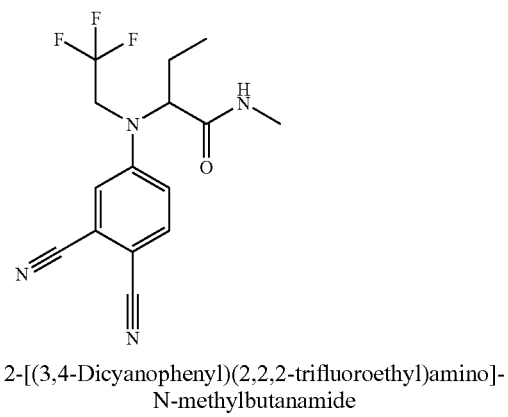

2-[(3,4-Dicyanophenyl)(2,2,2-trifluoroethyl)amino]-N-methylbutanamide

Synthesized in a manner similar to example 3 using 2-[(3,4-dicyanophenyl)(2,2,2-trifluoroethyl)amino]butanoic acid: MS (ES) m/z 325 (M+1).

Example 117

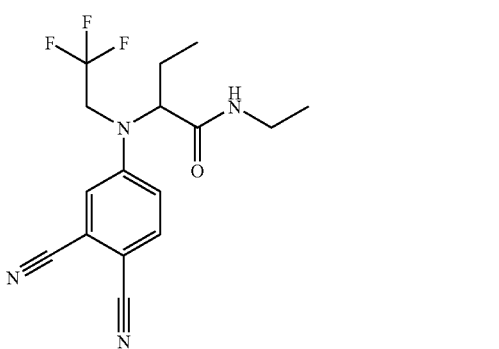

2-[(3,4-Dicyanophenyl)(2,2,2-trifluoroethyl)amino]-N-ethylbutanamide

Synthesized in a manner similar to example 3 using 2-[(3,4-dicyanophenyl)(2,2,2-trifluoroethyl)amino]butanoic acid and ethylamine: MS (ES) m/z 339 (M+1).

Example 118

1,1-Dimethylethyl N-(cyclopropylmethyl)-N-(3,4-dicyanophenyl)glycinate

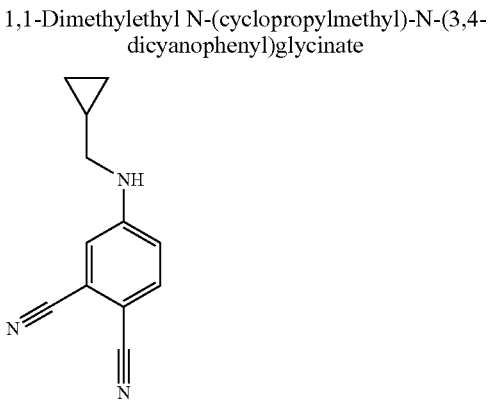

A. 4-[(Cyclopropylmethyl)amino]-1,2-benzenedicarbonitrile

Synthesized in a manner similar to example 1A using 4-fluoro-1,2-benzenedicarbonitrile: MS (ES) m/z 198 (M+1).

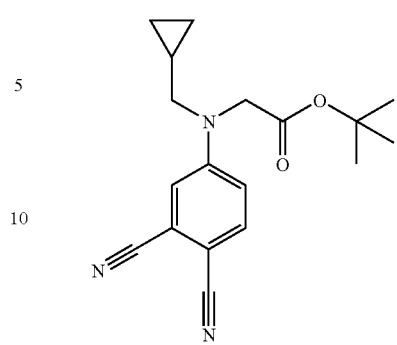

B. 1,1-Dimethylethyl N-(cyclopropylmethyl)-N-(3,4-dicyanophenyl)glycinate

Synthesized in a manner similar to example 1B using 4-[(cyclopropylmethyl)amino]-1,2-benzenedicarbonitrile: MS (ES) m/z 312 (M+1).

Example 119

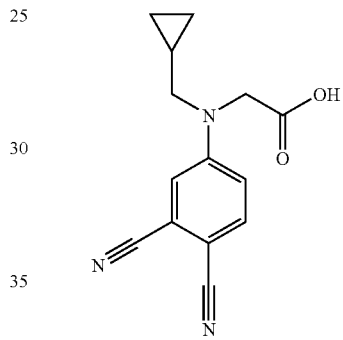

N-(Cyclopropylmethyl)-N-(3,4-dicyanophenyl)glycine

Synthesized in a manner similar to example 2 using 1,1-dimethylethyl N-(cyclopropylmethyl)-N-(3,4-dicyanophenyl)glycinate: MS (ES) m/z 256 (M+1).

Example 120

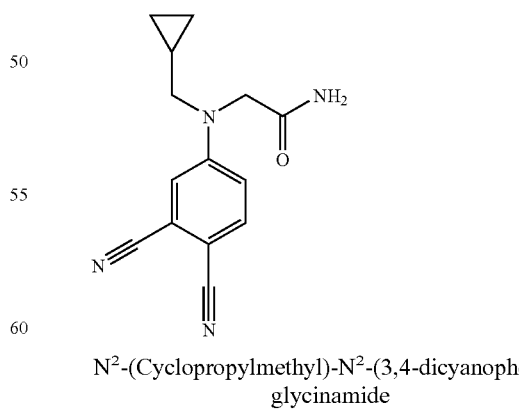

$N^2$-(Cyclopropylmethyl)-$N^2$-(3,4-dicyanophenyl)glycinamide

Synthesized in a manner similar to example 4 using N-(cyclopropylmethyl)-N-(3,4-dicyanophenyl)glycine: MS (ESI) m/z 255 (M+1).

Example 121

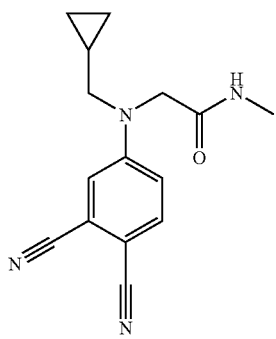

$N^2$-(Cyclopropylmethyl)-$N^2$-(3,4-dicyanophenyl)-
$N^1$-methylglycinamide

Synthesized in a manner similar to example 3 using N-(cyclopropylmethyl)-N-(3,4-dicyanophenyl)glycine: MS (ES) m/z 269 (M+1).

Example 122

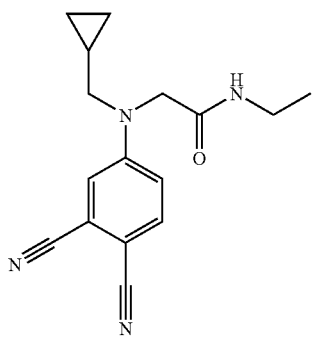

$N^2$-(Cyclopropylmethyl)-$N^2$-(3,4-dicyanophenyl)-
$N^1$-ethylglycinamide

Synthesized in a manner similar to example 3 using N-(cyclopropylmethyl)-N-(3,4-dicyanophenyl)glycine and ethylamine: MS (ES) m/z 283 (M+1).

Example 123

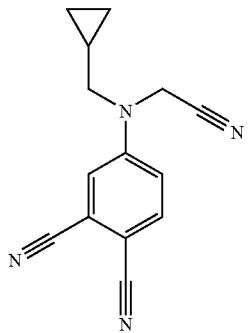

4-[(Cyanomethyl)(cyclopropylmethyl)amino]-1,2-
benzenedicarbonitrile

Synthesized in a manner similar to example 55 using $N^2$-(cyclopropylmethyl)-$N^2$-(3,4-dicyanophenyl)glycinamide: MS (ES) m/z 237 (M+1).

Example 124

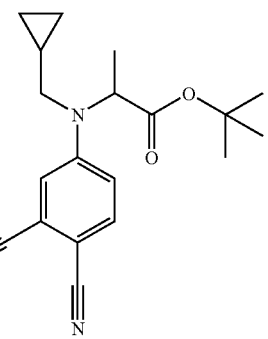

1,1-Dimethylethyl N-(cyclopropylmethyl)-N-(3,4-
dicyanophenyl)alaninate

Synthesized in a manner similar to example 1B using 4-[(cyclopropylmethyl)amino]-1,2-benzenedicarbonitrile and 1,1-dimethylethyl 2-bromopropanoate: MS (ES) m/z 326 (M+1).

Example 125

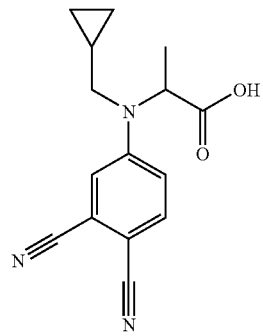

N-(Cyclopropylmethyl)-N-(3,4-dicyanophenyl)alanine

Synthesized in a manner similar to example 2 using 1,1-dimethylethyl N-(cyclopropylmethyl)-N-(3,4-dicyanophenyl)alaninate: MS (ES) m/z 270 (M+1).

Example 126

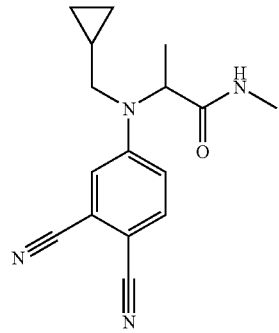

$N^2$-(Cyclopropylmethyl)-$N^2$-(3,4-dicyanophenyl)-
$N^1$-methylalaninamide

Synthesized in a manner similar to example 3 using N-(cyclopropylmethyl)-N-(3,4-dicyanophenyl)alanine: MS (ES) m/z 283 (M+1).

Example 127

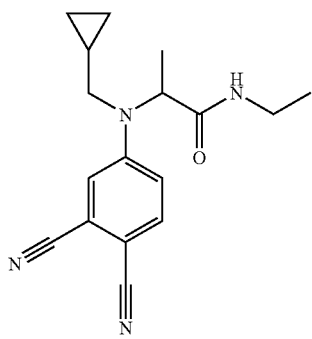

N²-(Cyclopropylmethyl)-N²-(3,4-dicyanophenyl)-
N¹-ethylalaninamide

Synthesized in a manner similar to example 3 using N-(cyclopropylmethyl)-N-(3,4-dicyanophenyl)alanine and ethylamine: MS (ES) m/z 297 (M+1).

Example 128

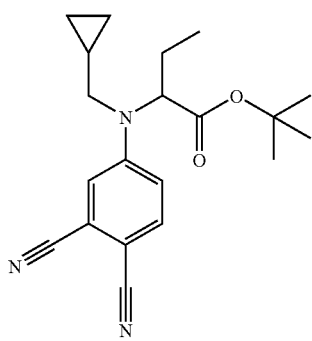

1,1-Dimethylethyl 2-[(cyclopropylmethyl)(3,4-dicyanophenyl)amino]butanoate

Synthesized in a manner similar to example 1B using 4-[(cyclopropylmethyl)amino]-1,2-benzenedicarbonitrile and tert-butyl 2-bromobutanoate: MS (ES) m/z 340 (M+1).

Example 129

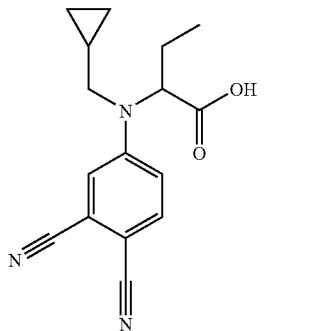

2-[(Cyclopropylmethyl)(3,4-dicyanophenyl)amino]
butanoic Acid

Synthesized in a manner similar to example 2 using 1,1-dimethylethyl 2-[(cyclopropylmethyl)(3,4-dicyanophenyl)amino]butanoate: MS (ES) m/z 284 (M+1).

Example 130

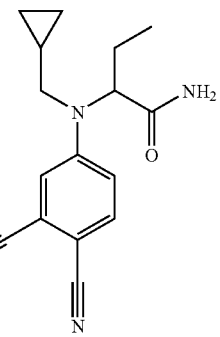

2-[(Cyclopropylmethyl)(3,4-dicyanophenyl)amino]
butanamide

Synthesized in a manner similar to example 4 using 2-[(cyclopropylmethyl)(3,4-dicyanophenyl)amino]butanoic acid: MS (ES) m/z 283 (M+1).

Example 131

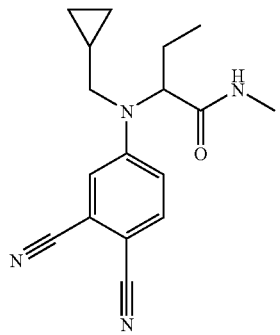

2-[(Cyclopropylmethyl)(3,4-dicyanophenyl)amino]-
N-methylbutanamide

Synthesized in a manner similar to example 3 using 2-[(cyclopropylmethyl)(3,4-dicyanophenyl)amino]butanoic acid: MS (ES) m/z 297 (M+1).

Example 132

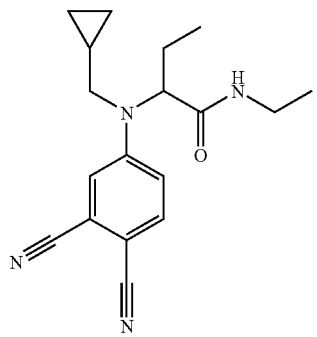

2-[(Cyclopropylmethyl)(3,4-dicyanophenyl)amino]-
N-ethylbutanamide

Synthesized in a manner similar to example 3 using 2-[(cyclopropylmethyl)(3,4-dicyanophenyl)amino]butanoic acid and ethylamine: MS (ES) m/z 311 (M+1).

Biological Section

Compounds of the current invention are modulators of the androgen receptor. Certain compounds of the present invention also modulate the glucocorticoid receptor, the mineralocorticoid receptor, and/or the progesterone receptor. Activity mediated through these oxosteroid nuclear receptors was determined using the following in vitro and in vivo assays.

In Vitro Assays:

The following abbreviations and sources of materials are used
Fluormone PL Red—a commercially available PR fluoroprobe (PanVera Corp, Product No P2965)
Fluormone GS Red—a commercially available GR fluoroprobe (PanVera Corp, Product No P2894)
Fluormone AL Green—a commercially available AR fluoroprobe (PanVera Corp, Product No P3010)
PR-LBD—Purified human progesterone ligand binding domain tagged with Glutathione Transferase (PanVera Corp, Product No P2900)
GR—purified human glucocorticoid receptor (PanVera Corp, Product No P2812)
AR-LBD—Purified rat androgen ligand binding domain tagged with Glutathione Transferase (PanVera Corp, Product No P3009)
PR Screening Buffer—100 mM potassium phosphate (pH 7.4), 100 µG/ml bovine gamma globulin, 15% ethylene glycol, 0.02% $NaN_3$, 10% glycerol (PanVera Corp Product No P2967) with 0.1% w/v CHAPS
AR Screening Buffer—pH 7.5 containing protein stabilizing agents and glycerol (PanVera Corp Product No P3011)
GR Screening Buffer—100 mM potassium phosphate (pH 7.4), 200 mM $Na_2MoO_2$, 1 mM EDTA, 20% DMSO (PanVera Corp Product No P2814) with GR stabilizing peptide (100 µM) (PanVera Corp Product No P2815)
DTT—dithiothreitol (PanVera Corp Product No P2325)
Discovery Analyst—is an FP reader
DMSO—dimethylsulphoxide Progesterone Receptor Fluorescence Polarization Assay:

The progesterone receptor fluorescence polarization assay is used to investigate the interaction of the compounds with the progesterone receptor.

Compounds are added to the 384 well black plates to a final volume of 0.5 µl. Sufficient Fluormone PL Red and PR-LBD are defrosted on ice to give a final concentration of 2 nM and 40 nM, respectively. PR screening buffer is chilled to 4° C. prior to addition of DTT to give a final concentration of 1 mM. The Fluormone PL Red and PR-LBD in PR Screening Buffer are added to compound plates to give a final volume of 10 µL. The assay is allowed to incubate at 20-22° C. for 2 hours. The plates are counted in a Discovery Analyst with suitable 535 nM excitation and 590 nM emission interference filters. Compounds that interact with the PR receptor result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $IC_{50}$ and d is the maximum. Maximum and minimum values are compared to adhesion in the absence of compound and in the presence of $10^{-5}$ M progesterone. Data is presented as the mean $pIC_{50}$ with the standard error of the mean of n experiments. Compounds with $pIC_{50}$ greater than 5.0 and a % max greater than 50 are considered desirable.

Androgen Receptor Fluorescence Polarization Assay:

The androgen receptor fluorescence polarization assay is used to investigate the interaction of the compounds with the androgen receptor.

Compounds are added to the 384 well black plates to a final volume of 0.5 µl. Sufficient Fluormone AL Green and AR-LBD are defrosted on ice to give a final concentration of 1 nM and 25 nM, respectively. AR screening buffer is chilled to 4° C. prior to addition of DTT to give a final concentration of 1 mM. The Fluormone AL Green and AR-LBD in AR Screening Buffer are added to compound plates to give a final volume of 10 µL. The assay is allowed to incubate at 20° C. for 5 hours. The plates are counted in a Discovery Analyst with suitable 485 nM excitation and 535 nM emission interference filters. Compounds that interact with the AR receptor result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $IC_{50}$ and d is the maximum. Maximum and minimum values are compared to adhesion in the absence of compound and in the presence of $10^{-5}$ M dihydrotestosterone. Data is presented as the mean $pIC_{50}$ with the standard error of the mean of n experiments. Compounds with $pIC_{50}$ greater than 5.0 and a % max greater than 50 are considered desirable.

Glucocorticoid Receptor Fluorescence Polarization Assay

The glucocorticoid receptor fluorescence polarization assay is used to investigate the interaction of the compounds with the glucocorticoid receptor.

Compounds are added to the 384 well black plates to a final volume of 0.5 µl. Sufficient Fluormone GS Red and GR are defrosted on ice to give a final concentration of 1 nM and 4 nM, respectively. GR screening buffer is chilled to 4° C. prior to addition of DTT to give a final concentration of 1 mM. The Fluormone GS Red and GR in GR Screening Buffer are added to compound plates to give a final volume of 10 µL. The assay is allowed to incubate at 4° C. for 12 hours. The plates are counted in a Discovery Analyst with suitable 535 nM excitation and 590 nM emission interference filters. Compounds that interact with the GR receptor result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $EC_{50}$ and d is the maximum. Maximum and minimum values are compared to adhesion in the absence of compound and in the presence of $10^{-5}$ M dexamethasone. Data is presented as the mean $pIC_{50}$ with the standard error of the mean of n experiments. Compounds with $pIC_{50}$ greater than 5.0 and a % max greater than 50 are considered desirable.

Transient Transfection Assay:

Cotransfection assays using full-length hAR were performed in CV-1 cells (monkey kidney fibroblasts). The cells were seeded in charcoal-stripped medium in 96-well plates (24,000 cells/well) and incubated overnight. Transient transfections were carried out using the following plasmids: pSG5-AR, MMTV LUC reporter, β-actin SPAP, and pBluescript (filler DNA). The cell plates were then incubated for 6-20 hours. The transfection mixture was washed away and then the cells were drugged with doses ranging from $10^{-10}$ to $10^{-5}$. Two replicates were used for each sample. Incubation with drug was continued for 14 hours. A spectrophotometer was used for SPAP measurements, while a topcounter was used to read the results from the luciferase assay. The ratio of luciferase activity to SPAP activity was calculated to normalize the variance in cell number and transfection efficiency.

Data Analysis:

Data were reduced using RoboFit99. The results were expressed as percent of maximum as calculated by the following formulas:

$$\text{fold activation} = \frac{\left(\frac{(Luc)}{(SPAP - SPAP_{substrate\ blank\ avg.})}\right) - \text{basal activation}}{\text{basal activation*}}$$

$$\text{*basal activation per plate} = \frac{(Luc\ \text{vehicle})}{\left(\frac{SPAP\ \text{vehicle} -}{\text{substrate blank average}}\right)}$$

$$\%\ \text{max.} = \left(\frac{\text{fold activation of unknown}}{\text{positive control fold activation } avg.}\right) \times 100$$

Curves were fit from these data using RoboFit to determine $EC_{50}$'s for agonists and $IC_{50}$'s for antagonists using the following equation:

$$Y=((V\max*x)/(K+x))+Y2$$

These values were converted to $pEC_{50}$'s and $pIC_{50}$'s for posting by using the following equations:

$$pEC_{50}=-\log(EC_{50})$$

$$pIC_{50}=-\log(IC_{50})$$

For antagonist assays, the percent maximum response antagonist was calculated by the following formula in which $Y_{min}$ and $Y_{max}$ are curve asymptotes at the maximum or minimum concentration tested:

$$\%\ \text{max.resp.ant.}=100*(1-Y_{min}/Y_{max})$$

For antagonist assays, pKb's were calculated using the following formula:

$$pKb=IC_{50}\ \text{of unknown}/((1+*conc.*)/DHT\ EC_{50}\ \text{average})$$

where *conc.*=concentration of DHT used as the agonist in the medium for the antagonist experiment, expressed in nM. This concentration was set at twice $pEC_{50}$. This would be 0.2 for AR.

Compounds with an $pXC_{50}$ greater than 5.0 are considered desirable.

Castrated Male Rat Model (ORX Rat)

The activity of the compounds of the present invention as modulators of the androgen receptor was investigated using a castrated male rat model (ORX) as described in C.D. Kockakian, *Pharmac. Therap. B* 1(2), 149-177 (1975); C. Tobin and Y. Joubert, *Developmental Biology* 146, 131-138 (1991); J. Antonio, J. D. Wilson and F. W. George, *J. Appl. Physiol.* 87(6) 2016-2019 (1999)) the disclosures of which herein are included by reference.

It has been well defined that androgens play important roles in the maintenance and growth of many tissues in both animals and humans. Muscles, like the levator ani and bulbocavernosus, and sexual accessory organs, such as the prostate glands and seminal vesicles have high expression levels of the androgen receptor and are known to respond quickly to exogenous androgen addition or androgen deprivation through testicular ablation. Castration produces dramatic atrophy of muscle and sexual accessory organs; whereas the administration of exogenous androgens to the castrated animal results in effective hypertrophy of these muscles and sexual accessory organs. Although the levator ani muscle, also known as the dorsal bulbocavernosus, is not 'true skeletal muscle' and definitely sex-linked, it is reasonable to use this muscle to screen muscle anabolic activities of test compounds because of its androgen responsiveness and simplicity of removal.

Male Sprague-Dawley rats weighing 160-180 grams were used in the assay. The rats were singly caged upon receiving and throughout the study. Bilateral orchidectomies were performed in sterilized surgical conditions under isoflurane anesthesia. An anteroposterior incision was made in the scrotum. The testicles were exteriorized and the spermatic artery and vas deferens were ligated with 4.0 silk 0.5 cm proximal to the ligation site. The testicles then were removed by a surgical scissors distal to the ligation sites. The tissue stumps were returned to the scrotum, the scrotum and overlying skin were closed by a surgical stapler. The Sham-ORX rats underwent all procedures except ligation and scissors cutting. The rats were assigned randomly into study groups 7-10 days post surgery based on the body weight.

Dihydrotestosterone (DHT) was used as a positive control (1-10 mg/kg s.c.). Compounds of the current invention were administered subcutaneously or orally for 4-28 days. The rats were weighed daily and doses were adjusted accordingly. The general well being of the animal was monitored throughout the course of the study.

At the end of the study, the rats were euthanized in a $CO_2$ chamber. The ventral prostate glands (VP), seminal vesicles (SV), levator ani muscle (LA) and bulbocavernosus (BC) were carefully dissected. The tissues were blotted dry, the weights were recorded, and then saved for histological and molecular analysis. The VP and SV weights serve as androgenic indicators and LA and BC are anabolic indicators. The ratio of anabolic to androgenic activities was used to evaluate the test compounds. Serum luteinizing hormone (LH), follicle stimulating hormone (FSH) and other potential serum markers of anabolic activities were also analyzed.

In general, desirable compounds show levator ani hypertrophy and very little prostate stimulation Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included within the scope of the appended claims.

What is claimed is:

1. A compound of formula (I)

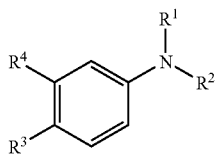

or a salt thereof, wherein
$R^1$ is $-(Q^1)_x-R^5$;
$Q^1$ is $C_1-C_6$ alkylene;
x is 0 or 1;
$R^5$ is H or $C_1-C_6$ alkyl;
$R^2$ is $-(Q^3)-(Q^4)-R^6$, or $-(Q^3)-CN$;
$Q^3$ is $C_1-C_6$ alkylene;
$Q^4$ is -C(O)-, -C(S)-, or -C(NR$^7$)-,
$R^7$ is H or alkyl;
$R^6$ is $C_1-C_6$ alkyl, $C_2-C_6$ alkenyl, $C_2-C_6$ alkynyl, hydroxy, $C_1-C_6$ alkoxy, phenoxy, benzyloxy, or -N(R$^8$)(R$^9$)
$R^8$ and $R^9$ each independently are H, hydroxy, $C_1-C_6$ alkyl, $C_2-C_6$ alkenyl, $C_2-C_6$ alkynyl, $-(Q^5)_y-C_3-C_6$cycloalkyl, -N(R$^{10}$)(R$^{11}$);
$Q^5$ is $C_1-C_6$ alkylene;
y is 0 or 1;
$R^{10}$ and $R^{11}$ each independently are H or $C_1-C_6$ alkyl;
$R^3$ is -CN; and
$R^4$ is $C_1-C_6$ haloalkyl.

2. The compound of claim 1 wherein $Q^1$ is methylene.
3. The compound of claim 1 wherein $Q^3$ is methylene.
4. A compound selected from:
1,1-dimethylethyl N-[4-cyano-3-(trifluoromethyl)phenyl]-N-methylglycinate;
1,1-dimethylethyl N-[4-cyano-3-(trifluoromethyl)phenyl]-N-ethylglycinate;
N-[4-cyano-3-(trifluoromethyl)phenyl]-N-ethylglycine;
$N^2$-[4-cyano-3-(trifluoromethyl)phenyl]-$N^2$-ethylglycinamide;
$N^2$-[4-cyano-3-(trifluoromethyl)phenyl]-$N^2$-ethyl-$N^1$-propylglycinamide;
$N^2$-[4-cyano-3-(trifluoromethyl)phenyl]-$N^1$-(cyclopropylmethyl)-$N^2$-ethylglycinamide;
$N^2$-[4-cyano-3-(trifluoromethyl)phenyl]-$N^2$-ethyl-$N^1$,$N^1$-dipropylglycinamide;
1,1-dimethylethyl N-[4-cyano-3-(trifluoromethyl)phenyl]-N-propylglycinate;
N-[4-cyano-3-(trifluoromethyl)phenyl]-N-propylglycine;
$N^2$-[4-cyano-3-(trifluoromethyl)phenyl]-$N^2$-propylglycinamide;
$N^2$-[4-cyano-3-(trifluoromethyl)phenyl]-$N^1$,$N^2$-dipropylglycinamide;
$N^2$-[4-cyano-3-(trifluoromethyl)phenyl]-$N^1$-(cyclopropylmethyl)-$N^2$-propylglycinamide;
1,1-dimethylethyl N-[4-cyano-3-(trifluoromethyl)phenyl]-N2-propen-1-ylglycinate;
methyl N-[4-cyano-3-(trifluoromethyl)phenyl]-N-(2-fluoroethyl)glycinate;
$N^2$-[4-cyano-3-(trifluoromethyl)phenyl]-$N^2$-(2-fluoroethyl)glycinamide;
1,1-dimethylethyl N-[4-cyano-3-(trifluoromethyl)phenyl]-N-(2-methylpropyl)glycinate;
N-[4-cyano-3-(trifluoromethyl)phenyl]-N-isobutylglycine;
$N^2$-[4-cyano-3-(trifluoromethyl)phenyl]-$N^2$-isobutylglycinamide;
$N^2$-[4-cyano-3-(trifluoromethyl)phenyl]-$N^2$-isobutyl-$N^1$-methylglycinamide;
N-[4-cyano-3-(trifluoromethyl)phenyl]-N-(2,2-dimethylpropyl)glycine;
$N^2$-[4-cyano-3-(trifluoromethyl)phenyl]-$N^2$-(2,2-dimethylpropyl)glycinamide;
$N^2$-[4-cyano-3-(trifluoromethyl)phenyl]-$N^2$-(1,1-dimethylethyl)glycinamide;
$N^2$-[4-cyano-3-(trifluoromethyl)phenyl]-$N^2$-(1-methylethyl) glycinamide;
$N^2$-[4-cyano-3-(trifluoromethyl)phenyl]-$N^1$-methyl-$N^2$-(1-methylethyl)glycinamide;
4-[(cyanomethyl)(methyl)amino]-2-(trifluoromethyl)benzonitrile; and
4-[(2-cyanoethyl)(methyl)amino]-2-(trifluoromethyl)benzonitrile.

5. A pharmaceutical composition comprising a compound according to claim 1, and a pharmaceutically acceptable carrier.

* * * * *